(12) United States Patent
Baldwin et al.

(10) Patent No.: US 8,198,453 B2
(45) Date of Patent: *Jun. 12, 2012

(54) PIPERIDINE RENIN INHIBITORS

(75) Inventors: John J. Baldwin, Gwynedd Valley, PA (US); David A. Claremon, Maple Glen, PA (US); Colin M. Tice, Ambler, PA (US); Salvacion Cacatian, Blue Bell, PA (US); Lawrence W. Dillard, Yardley, PA (US); Alexey V. Ishchenko, Somerville, MA (US); Jing Yuan, Lansdale, PA (US); Zhenrong Xu, Horsham, PA (US); Gerard McGeehan, Garnet Valley, PA (US); Wei Zhao, Eagleville, PA (US); Robert D. Simpson, Wilmington, DE (US); Suresh B. Singh, Kendall Park, NJ (US); Lanqi Jia, Horsham, PA (US); Patrick T. Flaherty, Pittsburgh, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 314 days.

This patent is subject to a terminal disclaimer.

(21) Appl. No.: 12/311,012

(22) PCT Filed: Sep. 18, 2007

(86) PCT No.: PCT/US2007/020164
§ 371 (c)(1),
(2), (4) Date: Jul. 14, 2009

(87) PCT Pub. No.: WO2008/036247
PCT Pub. Date: Mar. 27, 2008

(65) Prior Publication Data
US 2009/0312369 A1 Dec. 17, 2009

Related U.S. Application Data

(60) Provisional application No. 60/845,291, filed on Sep. 18, 2006.

(51) Int. Cl.
*C07D 405/12* (2006.01)
*A61K 31/453* (2006.01)

(52) U.S. Cl. ........................ 546/209; 514/326
(58) Field of Classification Search .................. 546/209; 514/326
See application file for complete search history.

(56) References Cited

U.S. PATENT DOCUMENTS

| | | | |
|---|---|---|---|
| 3,071,618 A | 1/1963 | Pinson et al. |
| 4,136,163 A | 1/1979 | Watson et al. |
| 4,908,372 A | 3/1990 | Carr et al. |
| 4,923,865 A | 5/1990 | Cossement et al. |
| 5,218,002 A | 6/1993 | Stroech et al. |
| 5,371,093 A | 12/1994 | Carr et al. |
| 5,380,731 A | 1/1995 | Carr et al. |
| 5,635,523 A | 6/1997 | Kempf et al. |
| 5,767,144 A | 6/1998 | Winn et al. |
| 6,162,927 A | 12/2000 | Winn et al. |
| 6,323,368 B1 * | 11/2001 | Evans ........................ 564/307 |
| 6,900,329 B2 | 5/2005 | Clader et al. |
| 6,946,481 B1 | 9/2005 | Winn et al. |
| 7,176,242 B2 | 2/2007 | John et al. |
| 7,754,737 B2 | 7/2010 | Baldwin et al. |
| 7,872,028 B2 | 1/2011 | Baldwin et al. |
| 2004/0044201 A1 | 3/2004 | Cummings et al. |
| 2007/0093492 A1 | 4/2007 | Jiaang et al. |
| 2007/0265331 A1 | 11/2007 | Decicco et al. |
| 2009/0018103 A1 | 1/2009 | Baldwin et al. |
| 2009/0186884 A1 | 7/2009 | Baldwin et al. |
| 2009/0318501 A1 | 12/2009 | Baldwin et al. |
| 2010/0160424 A1 | 6/2010 | Baldwin et al. |
| 2010/0317697 A1 | 12/2010 | Baldwin et al. |

FOREIGN PATENT DOCUMENTS

EP 0178947 A2 4/1986

(Continued)

OTHER PUBLICATIONS

Written Opinion of the International Searching Authority, International Application No. PCT/US08/67650 (Jun. 22, 2009).
International Search Report, International Application No. PCT/US08/67650 (Jun. 22, 2009).
Notification Concerning Transmittal of International Preliminary Report on Patentability, and International Preliminary Report on Patentability, International Application No. PCT/US2005/036230, mail date Apr. 19, 2007.

(Continued)

*Primary Examiner* — David K O Dell
(74) *Attorney, Agent, or Firm* — Hamilton, Brook, Smith & Reynolds, P.C.

(57) ABSTRACT

The present invention is directed to aspartic protease inhibitors represented by the following structural formula (I), or a pharmaceutically acceptable salt thereof. The present invention is also directed to pharmaceutical compositions comprising the aspartic protease inhibitors of Structural Formula (I). Methods of antagonizing one or more aspartic proteases in a subject in need thereof, and methods for treating an aspartic protease mediated disorder in a subject using these aspartic protease inhibitors are also disclosed.

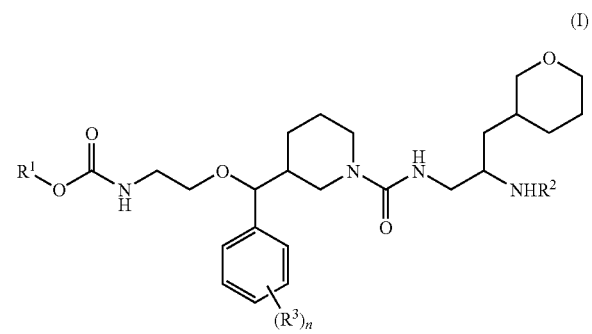

3 Claims, 2 Drawing Sheets

FOREIGN PATENT DOCUMENTS

| | | |
|---|---|---|
| EP | 1 882 684 A1 | 1/2008 |
| GB | 1351761 A | 5/1974 |
| JP | 51015098 A | 5/1976 |
| JP | 61100563 A | 5/1986 |
| JP | 01313467 | 12/1989 |
| JP | 2002/525361 A | 8/2002 |
| WO | WO 96/04232 A1 | 2/1996 |
| WO | WO 98/54179 A1 | 12/1998 |
| WO | WO 99/54321 | 10/1999 |
| WO | WO 00/18744 A1 | 4/2000 |
| WO | WO 00/40558 | 7/2000 |
| WO | WO 00/63172 | 10/2000 |
| WO | WO 03/006423 A1 | 1/2003 |
| WO | WO 03/090690 | 11/2003 |
| WO | WO 2004/002483 | 1/2004 |
| WO | WO 2004/013098 | 2/2004 |
| WO | WO 2004/024675 | 3/2004 |
| WO | WO 2005/049027 | 6/2005 |
| WO | WO 2006/023844 | 3/2006 |
| WO | WO 2006/042150 A1 | 4/2006 |
| WO | WO 2007/070201 A1 | 6/2007 |
| WO | WO 2007/117557 | 10/2007 |
| WO | WO 2008/036216 A1 | 3/2008 |
| WO | WO 2008/156817 | 12/2008 |
| WO | WO 2009/096996 | 8/2009 |
| WO | WO 2009/154766 | 12/2009 |
| WO | WO 2009/158377 | 12/2009 |
| WO | WO 2011/017533 | 2/2011 |

OTHER PUBLICATIONS

Notification Concerning Transmittal of International Preliminary Report on Patentability, and International Preliminary Report on Patentability, International Application No. PCT/US2006/043920, mail date May 22, 2008.
International Search Report, International Application No. PCT/US07/020164 (Dec. 28, 2007).
Written Opinion of the International Searching Authority, International Application No. PCT/US07/020164 (Dec. 28, 2007).
Office Action from European Patent Office, European Application No. 07 838 381.7, Dated Oct. 16, 2009.
Database Casreact, AN 90:168416.
Dec. 28, 2007, International Search Report, PCT/US2007/020164.
Dec. 28, 2007, Written Opinion of the International Searching Authority, PCT/US2007/020164.
Maibaum, J., et al., "Renin Inhibitors as Novel Treatments for Cardiovascular Disease," *Expert Opinion on Therapeutic Patents*, vol. 13, No. 5, pp. 589-603 (2003).
Moffett, R.B., "New Compounds with Possible Pharmacological Activity," *Journal of Chemical and Engineering Data*, vol. 25, No. 2, pp. 176-183 (1980).
Whitehead, C.W., "The Synthesis of 5-Carbethoxyuracils," *Journal of the American Chemical Society*, vol. 74, pp. 4267-4271 (1952).
Garrigues, B., et al., "Synthèse de 2-tert-butylthiophènes substitués en position 5," *Bulletin De La Societe Chimique De France*, vol. 130, No. 1, pp. 58-63 (1993).
Schultz O.E., et al., "Pyridine and quinoline analogues of procaine and procainamide," *Arzneimittel-Forschung*, vol. 22, No. 7, pp. 1117-1120 (1972).
Praly-Deprez, I., et al., "Synthesis of 11-amino-substituted-5,6-dimethyl-5H-pyrido[3',4':4,5]pyrrolo-[2,3-g]isoquinolines as New Ellipticine Analogues," *Journal of the Chemical Society*, Perkin Transactions 1., No. 12, pp. 3173-3175 (1991).
Database Beilstein XP002366304, Database Accession No. 7588231, 4-(2,2-dimethoxypropyl)-N-(2-hydroxyethyl) benzamide, vol. 108, No. 22, pp. 2800-2802 (1996).
International Search Report, International Application No. PCT/US2006/043920 (Mar. 20, 2007).
Written Opinion of the International Searching Authority, International Application No. PCT/US2006/043920 (Mar. 20, 2007).
International Search Report, International Application No. PCT/US2005/036230 (Feb. 20, 2006).
Written Opinion of the International Searching Authority, International Application No. PCT/US2005/036230 (Feb. 20, 2006).
International Search Report, International Application No. PCT/US2007/020086 (Feb. 5, 2008).
Written Opinion of the International Searching Authority, International Application No. PCT/US2007/020086 (Feb. 5, 2008).
Notification Concerning Transmittal of International Preliminary Report on Patentability, and International Preliminary Report on Patentability, International Application No. PCT/US2007/020164, mail date Apr. 2, 2009.
Notification Concerning Transmittal of International Preliminary Report on Patentability, and International Preliminary Report on Patentability, International Application No. PCT/US2007/020086, mail date Apr. 2, 2009.
Bhanuprakash K., et al., "Computational Design of New Cyclic Urea Inhibitors for Improved Binding of HIV-1 Aspartic Protease," *Biochemical and Biophysical Research Communications*, 268(2): 384-389 (2000).
Restriction Requirement from U.S. Patent Office, U.S. Appl. No. 12/311,020, Dated: Jun. 3, 2011.
Restriction Requirement Office Action from U.S. Patent Office, U.S. Appl. No. 12/665,213, Dated: Jun. 24, 2011.
Office Action from U.S. Patent Office, U.S. Appl. No. 12/311,020, Dated: Aug. 23, 2011.
Tice, Colin M., et al., "Design and optimization of renin inhibitors: Orally bioavailable alkyl amines", *Bioorganic & Medicinal Chemistry Letters*, 19(13): 3541-3545 (2009).
Xu, Zhenrong, et al., "Optimization of orally bioavailable alkyl amine renin inhibitors", *Bioorganic & Medicinal Chemistry Letters*, 20(2): 694-699 (2010).
Jia, Lanqu, et al., "Discovery of VTP-27999, an Alkyl Amine Renin Inhibitor with Potential for Clinical Utility", *ACS Medicinal Chemistry Letters*, 2 (10): 747-751 (Aug. 9, 2011).
Wood, J.N., et al., "Voltage-Gated Sodium Channels and Pain Pathways," *J. Neurobiol.*, 61:55-71 (2004).
Written Opinion of the International Searching Authority, International Application No. PCT/US2007/008518 (Oct. 10, 2007).
International Search Report, International Application No. PCT/US2007/008518 (Oct. 10, 2007).
Notification Concerning Transmittal of International Preliminary Report on Patentability, and International Preliminary Report on Patentability, International Application No. PCT/US2007/008518, mail date Oct. 16, 2008.
International Search Report, International Application No. PCT/US2008/007662 (Apr. 21, 2009).
Written Opinion of the International Searching Authority, International Application No. PCT/US2008/007662 (Apr. 21, 2009).
Notification Concerning Transmittal of International Preliminary Report on Patentability, and International Preliminary Report on Patentability, International Application No. PCT/US2008/007662, mail date Jan. 7, 2010.
Notification Concerning Transmittal of International Preliminary Report on Patentability, and International Preliminary Report on Patentability, International Application No. PCT/US2008/067650, mail date Jan. 7, 2010.
International Search Report, International Application No. PCT/US2009/48389 (Sep. 11, 2009).
Written Opinion of the International Searching Authority, International Application No. PCT/US2009/48389 (Sep. 11, 2009).
Notification Concerning Transmittal of International Preliminary Report on Patentability, and International Preliminary Report on Patentability, International Application No. PCT/US2009/48389, mail date Jan. 13, 2011.
International Search Report, International Application No. PCT/US2009/003650 (Oct. 9, 2009).
Written Opinion of the International Searching Authority, International Application No. PCT/US2009/003650 (Oct. 9, 2009).
Notification Concerning Transmittal of International Preliminary Report on Patentability, and International Preliminary Report on Patentability, International Application No. PCT/US2009/003650, mail date Jan. 6, 2011.
International Search Report and Written Opinion of the International Searching Authority, International Application No. PCT/US2010/044568 (Nov. 8, 2010).

Notice of Allowance and Fees Due, U.S. Appl. No. 12/665,213, filed Feb. 19, 2010, Date of Notice: Feb. 10, 2012

Notification Concerning Transmittal of International Preliminary Report on Patentability, International Application No. PCT/US2010/044568, International Filing Date: Aug. 5, 2010, Date of Mailing: Feb. 16, 2012.

Hammond, et al., "Preparation of phenyloxymethylbenzamide derivatives for use as aspartic protease inhibitors," AN 2009:1589830; DN 152:74734, CAPLUS [online],[Retrieved on Mar. 16, 2012]. Retrieved from the Internet URL: https://stnweb.cas.org/cgi-bin/sdcgi?SID=753964-0147118521-200&APP=stnweb&.

Database Casreact, AN 90:168416: Abstract for—Orlova, E. K. et al., "Synthesis and neurotropic properties of some alpha-amino benzyl piperidines," Khimiko-Farmatsevticheskii Zhurral, 13(1): 47-51 (1979).

Dorwald, F. Zaragoza, "Side Reactions in Organic Synthesis: A Guide to Successful Synthesis Design," Weinheim: Wiley-VCH Verlag GmbH & Co. KGaA, Preface p. ix, (2005).

English Translation of Notification of the First Office Action, Chinese Patent Application No. 200580042064.7, Date of Notification May 8, 2009.

Examination Report from Gulf Cooperation Council Patent Office, GCC Application No. GCC/P/2006/7201, Dated Jul. 21, 2009.

Jordan, V.Craig, "Tamoxifen: a Most Unlikely Pioneering Medicine," Nature Reviews: Durg Discovery, 2:205-213 (Mar. 2003).

Notice of Allowance from US Patent Office, U.S. Appl. No. 11/664,558, dated Mar. 1, 2010.

Notice of Allowance from US Patent Office, U.S. Appl. No. 12/225,985, dated Oct. 12, 2010.

Office Action from European Patent Office, European Application No. 07 838 310.6, Dated Sep. 2, 2009.

Office Action from European Patent Office, European Application No. 06 837 406.5, Dated Oct. 29, 2009.

Office Action from US Patent Office, U.S. Appl. No. 12/665,213, Dated Sep. 29, 2010.

Office Action from US Patent Office, U.S. Appl. No. 12/665,213, Dated Oct. 29, 2010.

Office Action from US Patent Office, U.S. Appl. No. 12/665,213, Dated Dec. 17, 2010.

Rahuel, J. et al., "Structure-Based Drug Design: The Discovery of Novel Nonpeptide Orally Active Inhibitors of Human Renin," Chemistry & Biology, 7:493-504 (2000).

Shabat, D., et al., "Katalytische Antikorper als Sonden Fur die Evolution von Enzymen: Modellierung einer fruhen Glycosidase," *Angew. Chem.*, 108(22):2800-2802 (1996).

Stachel, S.J. et al., "Conformationally biased P3 amide replacements of beta-secretase inhibitors," Bioorganic & Med. Chem. Letters, 16(3):641-644 (2006).

Office Communication, U.S. Appl. No. 12/802,142, filed May 28, 2010, Date of Communication: Mar. 19, 2012.

Office Communication, U.S. Appl. No. 12/084,928, filed Nov. 5, 2009, Date of Communication: Mar. 5, 2012.

\* cited by examiner

PIPERIDINE RENIN INHIBITORS

RELATED APPLICATIONS

This application is the U.S. National Stage of International Application No. PCT/US2007/020164, filed 18 Sep. 2007, published in English, and claims the benefit under 35 U.S.C. §119 or 365 to U.S. Provisional Application No. 60/845,291, filed Sep. 18, 2006. The entire teachings of the above applications are incorporated herein by reference.

BACKGROUND OF THE INVENTION

Aspartic proteases, including renin, β-secretase (BACE), HIV protease, HTLV protease and plasmepsins I and II, are implicated in a number of disease states. In hypertension, elevated levels of angiotensin I, the product of renin catalyzed cleavage of angiotensinogen are present. Elevated levels of β amyloid, the product of BACE activity on amyloid precursor protein, are widely believed to be responsible for the amyloid plaques present in the brains of Alzheimer's disease patients. The viruses HIV and HTLV depend on their respective aspartic proteases for viral maturation. *Plasmodium falciparum* uses plasmepsins I and II to degrade hemoglobin.

In the renin-angiotensin-aldosterone system (RAAS), the biologically active peptide angiotensin II (Ang II) is generated by a two-step mechanism. The highly specific aspartic protease renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAAS represents a major advance in the treatment of cardiovascular diseases (Zaman, M. A. et al *Nature Reviews Drug Discovery* 2002, 1, 621-636). ACE inhibitors and $AT_1$ blockers have been accepted as treatments of hypertension (Waeber B. et al., "The renin-angiotensin system: role in experimental and human hypertension," in Berkenhager W. H., Reid J. L. (eds): *Hypertension*, Amsterdam, Elsevier Science Publishing Co, 1996, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al., *N Engl. J: Med*, 1992, 327, 669).

Interest in the development of renin inhibitors stems from the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be bypassed by chymase, a serine protease (Husain A., *J. Hypertens.*, 1993, 11, 1155). In patients, inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the ATI receptor (e.g., by losartan) on the other hand overexposes other AT-receptor subtypes to Ang II, whose concentration is dramatically increased by the blockade of AT1 receptors. In summary, renin inhibitors are not only expected to be superior to ACE inhibitors and $AT_1$ blockers with regard to safety, but more importantly also with regard to their efficacy in blocking the RAAS.

Only limited clinical experience (Azizi M. et al., *J. Hypertens.*, 1994, 12, 419; Neutel J. M. et al., *Am. Heart*, 1991, 122, 1094) has been generated with renin inhibitors because their peptidomimetic character imparts insufficient oral activity (Kleinert H. D., *Cardiovasc. Drugs*, 1995, 9, 645). The clinical development of several compounds has been stopped because of this problem together with the high cost of goods. It appears as though only one compound has entered clinical trials (Rahuel J. et al., *Chem. Biol.*, 2000, 7, 493; Mealy N. E., *Drugs of the Future*, 2001, 26, 1139). Thus, metabolically stable, orally bioavailable and sufficiently soluble renin inhibitors that can be prepared on a large scale are not available. Recently, the first non-peptide renin inhibitors were described which show high in vitro activity (Oefner C. et al., *Chem. Biol.*, 1999, 6, 127; Patent Application WO 97/09311; Maerki H. P. et al., *Il Farmaco*, 2001, 56, 21). The present invention relates to the unexpected identification of renin inhibitors of a non-peptidic nature and of low molecular weight. Orally active renin inhibitors which are active in indications beyond blood pressure regulation where the tissular renin-chymase system may be activated leading to pathophysiologically altered local functions such as renal, cardiac and vascular remodeling, atherosclerosis, and restenosis, are described.

All documents cited herein are incorporated by reference.

SUMMARY OF THE INVENTION

One embodiment of the invention is an aspartic protease inhibitor, which is a compound represented by Structural Formula (I):

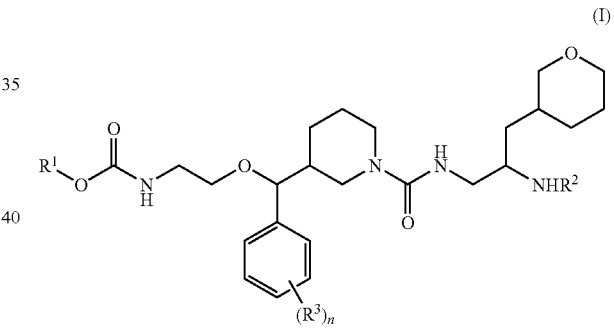

or a pharmaceutically acceptable salt thereof, wherein:
$R^1$ is alkyl, cycloalkyl or cycloalkylalkyl;
$R^2$ is H or alkyl;
$R^3$ is F, Cl, Br, cyano, nitro, alkyl, haloalkyl, alkoxy, haloalkoxy, or alkanesulfonyl; and
n is 0, 1, 2, or 3.

Another embodiment of the invention is an aspartic protease inhibitor, which is a compound represented by Structural Formula (II):

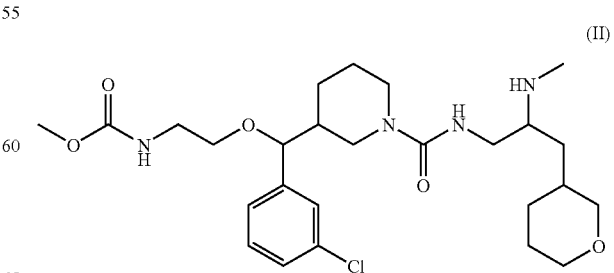

or a pharmaceutically acceptable salt thereof.

Another embodiment of the invention is an aspartic protease inhibitor, which is a compound represented by Structural Formula (IIa):

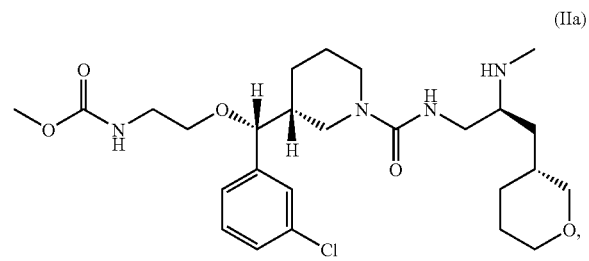

or a pharmaceutically acceptable salt thereof, wherein the compound is at least 90% optically pure.

Another embodiment of the invention is a pharmaceutical composition comprising a pharmaceutically acceptable carrier or diluent and an aspartic protease inhibitor disclosed herein (e.g., a compound represented by Structural Formulas (I), (II), (IIa) or a pharmaceutically acceptable salt thereof). The pharmaceutical composition is used in therapy, e.g., for inhibiting an aspartic protease mediated disorder in a subject.

Another embodiment of the invention is a method of antagonizing one or more aspartic proteases in a subject in need of such treatment. The method comprises administering to the subject an effective amount of an aspartic protease inhibitor disclosed herein (e.g., a compound represented by Structural Formulas (I), (II), (IIa) or a pharmaceutically acceptable salt thereof).

Another embodiment of the invention is a method of treating an aspartic protease mediated disorder in a subject. The method comprises administering to the subject an effective amount of an aspartic protease inhibitor disclosed herein (e.g., a compound represented by Structural Formulas (I), (II), (IIa) or a pharmaceutically acceptable salt thereof).

Another embodiment of the invention is the use of an aspartic protease inhibitor disclosed herein (e.g., a compound represented by Structural Formulas (I), (II), (IIa) or a pharmaceutically acceptable salt thereof) for the manufacture of a medicament for antagonizing one or more proteases in a subject in need of such treatment.

Another embodiment of the invention is the use of an aspartic protease inhibitor disclosed herein (e.g., a compound represented by Structural Formulas (I), (II), (IIa) or a pharmaceutically acceptable salt thereof) for the manufacture of a medicament for treating an aspartic protease mediated disorder in a subject.

Another embodiment of the invention is the use of an aspartic protease inhibitor disclosed herein (e.g., a compound represented by Structural Formulas (I), (II), (IIa) or a pharmaceutically acceptable salt thereof) for therapy, such as treating an aspartic protease mediated disorder in a subject. Values for the variables of Structural Formulas (I) are as described above.

Another embodiment of the invention is the use of an aspartic protease inhibitor disclosed herein (e.g., a compound represented by Structural Formulas (I), (II), (IIa) or a pharmaceutically acceptable salt thereof) for treating a subject having hypertension, congestive heart failure, cardiac hypertrophy, cardiac fibrosis, cardiomyopathy post-infarction, nephropathy, vasculopathy and neuropathy, a disease of the coronary vessels, post-surgical hypertension, restenosis following angioplasty, raised intra-ocular pressure, glaucoma, abnormal vascular growth, hyperaldosteronism, an anxiety state, or a cognitive disorder, wherein values for the variables of Structural Formula (I) are as described above.

DETAILED DESCRIPTION OF THE INVENTION

Figure 1:
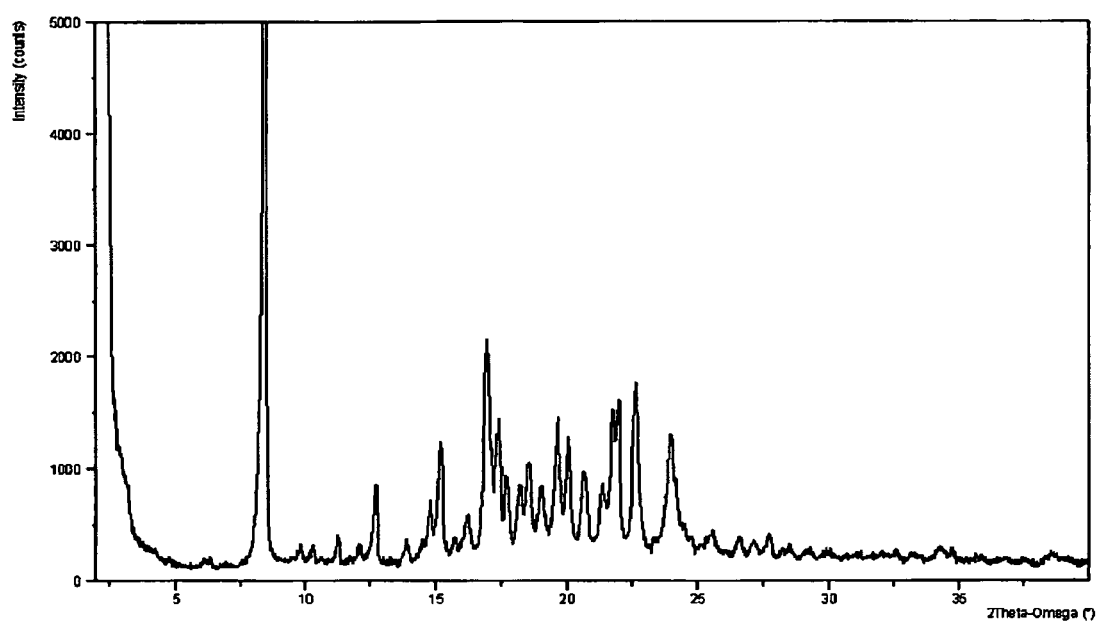
FIG. 1 shows an X-ray powder diffraction pattern of the pamoate salt of compound 7.

The invention is directed to an aspartic protease inhibitor represented by Structural Formula (I), or a pharmaceutically acceptable salt thereof.

In another embodiment, the aspartic protease inhibitor of the present invention is represented by the Structural Formula (Ia):

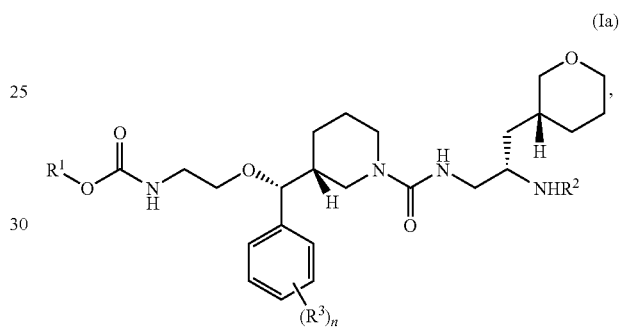

or a pharmaceutically acceptable salt thereof.

Values and specific values for the variables in Structural Formulas (I) and (Ia) are defined as follows:

$R^1$ is alkyl, cycloalkyl (e.g., cyclopropyl) or cycloalkylalkyl (e.g., cyclopropyl($C_1$-$C_3$)alkyl); more specifically, $R^1$ is ($C_1$-$C_3$)alkyl; even more specifically, $R^1$ is methyl;

$R^2$ is H or alkyl; more specifically, $R^2$ is H or ($C_1$-$C_3$)alkyl; even more specifically, $R^2$ is H or methyl;

$R^3$ is F, Cl, Br, cyano, nitro, alkyl, haloalkyl, alkoxy, haloalkoxy, or alkanesulfonyl; more specifically, $R^3$ is F, Cl, Br, cyano, nitro, ($C_1$-$C_3$)alkyl, halo($C_1$-$C_3$)alkyl, ($C_1$-$C_3$)alkoxy, halo($C_1$-$C_3$)alkoxy, or ($C_1$-$C_3$)alkanesulfonyl; even more specifically, $R^3$ is F, Cl, or methyl; and n is 0, 1, 2, or 3; more specifically, n is 0, 1, or 2; even more specifically, n is 1 or 2.

In a specific embodiment, the aspartic protease inhibitor is represented by Structural Formula (I) or (Ia), wherein $R^1$ is ($C_1$-$C_3$)alkyl; $R^2$ is H or ($C_1$-$C_3$)alkyl; $R^3$ is F, Cl, Br, cyano, nitro, ($C_1$-$C_3$)alkyl, halo($C_1$-$C_3$)alkyl, ($C_1$-$C_3$)alkoxy, halo($C_1$-$C_3$)alkoxy, or ($C_1$-$C_3$)alkanesulfonyl; and n is 0, 1, 2, or 3.

In another specific embodiment, the aspartic protease inhibitor is represented by Structural Formula (I) or (Ia), wherein $R^1$ is methyl and $R^2$ is H or methyl; values and specific values for other variables are as defined above for Formulas (I) and (Ia). In another specific embodiment, $R^1$ is methyl; $R^2$ is H or methyl; and $R^3$ is F, Cl or methyl; values and specific values for other variables are as defined above for Formulas (I) and (Ia).

In another specific embodiment, the aspartic protease inhibitor of the present invention is one of the following compounds or their enantiomers or diastereomers. Also included are pharmaceutically acceptable salts and solvates (e.g., hydrates) of all of the following and their enantiomers and diastereomers:

| Cpd No. | Structural | Name |
|---|---|---|
| 1 | | methyl 2-((R)-((R)-1-((S)-2-amino-3-((R)-tetrahydro-2H-pyran-3-yl)propylcarbamoyl)piperidin-3-yl)(3-chlorophenyl)methoxy)ethylcarbamate |
| 2 | | methyl 2-((R)-((R)-1-((S)-2-amino-3-((R)-tetrahydro-2H-pyran-3-yl)propylcarbamoyl)piperidin-3-yl)(3-fluorophenyl)methoxy)ethylcarbamate |
| 3 | | methyl 2-((R)-((R)-1-((S)-2-amino-3-((R)-tetrahydro-2H-pyran-3-yl)propylcarbamoyl)piperidin-3-yl)(3-chloro-5-fluorophenyl)methoxy)-ethylcarbamate |
| 4 | | methyl 2-((R)-((R)-1-((S)-2-amino-3-((R)-tetrahydro-2H-pyran-3-yl)propylcarbamoyl)piperidin-3-yl)(3,5-difluorophenyl)methoxy)ethylcarbamate |
| 5 | | methyl 2-((R)-((R)-1-((S)-2-amino-3-((R)-tetrahydro-2H-pyran-3-yl)propylcarbamoyl)piperidin-3-yl)(5-chloro-2-methylphenyl)methoxy)-ethylcarbamate |
| 6 | | methyl 2-((R)-((R)-1-((S)-2-amino-3-((R)-tetrahydro-2H-pyran-3-yl)propylcarbamoyl)piperidin-3-yl)(5-fluoro-2-methylphenyl)methoxy)-ethylcarbamate |

-continued

| Cpd No. | Structural | Name |
|---|---|---|
| 7 | | methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)-ethylcarbamate |
| 8 | | methyl 2-((R)-(5-chloro-2-methylphenyl)((R)-1-((S)-2-(methylamino)-3-((R)-tetrahydro-2H-pyran-3-yl)propylcarbamoyl)-piperidin-3-yl)methoxy)-ethylcarbamate |
| 9 | | methyl 2-((R)-(3-chloro-5-fluorophenyl)((R-1-((S)-2-(methylamino)-3-((R)-tetrahydro-2H-pyran-3-yl)propylcarbamoyl)-piperidin-3-yl)methoxy)-ethylcarbamate |
| 10 | | methyl 2-((R)-(3,5-difluorophenyl)((R)-1-((S)-2-(methylamino)-3-(R)-tetrahydro-2H-pyran-3-yl)propylcarbamoyl)-piperidin-3-yl)methoxy)-ethylcarbamate |
| 11 | | methyl 2-((S)-(5-chloro-2-methylphenyl)((R)-1-((S)-2-(methylamino)-3-((R)-tetrahydro-2H-pyran-3-yl)propylcarbamoyl)-piperidin-3-yl)methoxy)-ethylcarbamate |
| 12 | | methyl 2-((R)-(5-chloro-2-methylphenyl)((R)-1-((S)-2-(ethylamino)-3-((R)-tetrahydro-2H-pyran-3-yl)propylcarbamoyl)-piperidin-3-yl)methoxy)-ethylcarbamate |

| Cpd No. | Structural | Name |
|---|---|---|
| 13 | 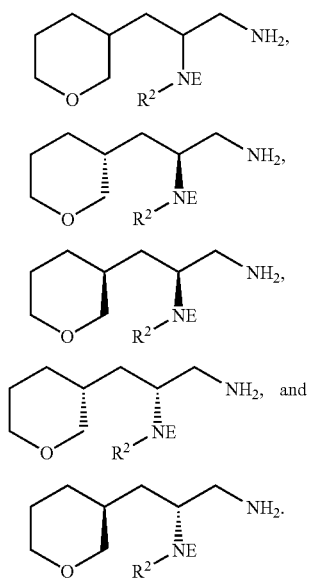 | methyl 2-((R)-(3-chlorophenyl)((R)-1-((S)-2-(ethylamino)-3-((R)-tetrahydro-2H-pyran-3-yl)propylcarbamoyl)-piperidin-3-yl)methoxy)-ethylcarbaniate |

Another embodiment of the invention is directed to an intermediate for synthesizing the aspartic protease inhibitors disclosed herein, represented by Structural Formulas (III), (IIIa), (IIIb), (IIIc) or (IIId) and salts thereof (preferably pharmaceutically acceptable salts):

(III)

(IIIa)

(IIIb)

(IIIc)

(IIId)

In Structural Formulas (III), (IIIa), (IIIb), (IIIc), and (IIId), E is H or an amine protecting group. Amine protecting groups include carbamate, amide, and sulfonamide protecting groups known in the art (T. W. Greene and P. G. M. Wuts "Protective Groups in Organic Synthesis" John Wiley & Sons, Inc., New York 1999) and the entire teaching of which is herein incorporated by reference. Specific amine protecting groups include tert-butoxycarbonyl (Boc), benzyloxycarbonyl (Cbz) and 1-[2-(trimethylsilyl)ethoxycarbonyl] (Teoc). More specifically, the amine protecting group is tert-butoxycarbonyl (Boc). Values and specific values for $R^2$ are as described for Structural Formula (I).

In a specific embodiment, the intermediate is each of the following compounds or their enantiomers or diastereomers. Pharmaceutically acceptable salts of all of the following are also included:

| Cpd No. | Cpd Name |
|---|---|
| IIIa-1 | tert-butyl (S)-1-amino-3-((R)-tetrahydro-2H-pyran-3-yl)propan-2-ylcarbamate |
| IIIa-2 | tert-butyl (S)-1-amino-3-((R)-tetrahydro-2H-pyran-3-yl)propan-2-yl(methyl)carbamate |
| III-1 | tert-butyl-1-amino-3-(tetrahydro-2H-pyran-3-yl)propan-2-ylcarbamate |
| III-2 | tert-butyl-1-amino-3-(tetrahydro-2H-pyran-3-yl)propan-2-yl(methyl)carbamate |

When any variable (e.g., $R^3$) occurs more than once in a compound, its definition on each occurrence is independent of any other occurrence. For example, $R^3$, for each occurrence, is independently selected from the group consisting of F, Cl, Br, cyano, nitro, alkyl, haloalkyl, alkoxy, haloalkoxy, and alkanesulfonyl.

When the "aspartic protease inhibitor" of the present invention is named or depicted by structure, it also includes pharmaceutically acceptable salts thereof.

"Alkyl", alone or part of another moiety (such as cycloalkylalkyl, alkoxy, haloalkoxy, haloalkyl or alkoxy), means a saturated aliphatic branched or straight-chain mono- or divalent hydrocarbon radical. Alkyls commonly have from one to six carbon atoms, typically from one to three carbon atoms. Thus, "$(C_1-C_3)$alkyl" means a radical having from 1-3 carbon atoms in a linear or branched arrangement. "$(C_1-C_3)$ alkyl" includes methyl, ethyl, propyl and isopropyl.

"Cycloalkyl", alone or as part of another moiety (such as cycloalkylalkyl) means a saturated aliphatic cyclic monovalent hydrocarbon radical. Typically, cycloalkyls have from three to ten carbon atoms and are mono, bi or tricyclic. Tricyclic cycloalkyls can be fused or bridged. Typically, cycloalkyls are $C_3-C_8$ monocyclic and are more commonly cyclopropyl.

"Cycloalkylalkyl" means an alkyl radical substituted with a cycloalkyl group.

"Haloalkyl" includes mono, poly, and perhaloalkyl groups where the halogens are independently selected from fluorine, chlorine, and bromine.

"Alkoxy" means an alkyl radical attached through an oxygen linking atom. "$(C_1\text{-}C_3)$-alkoxy" includes the methoxy, ethoxy, and propoxy.

"Haloalkoxy" is a haloalkyl group which is attached to another moiety via an oxygen linker.

"Alkanesulfonyl" is an alkyl radical attached through a

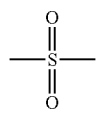

linking group. "$(C_1\text{-}C_3)$alkanesulfonyl" includes methanesulfonyl, ethanesulfonyl and propanesulfonyl.

Certain of the disclosed aspartic protease inhibitors may exist in various tautomeric forms. The invention encompasses all such forms, including those forms not depicted structurally.

Certain of the disclosed aspartic protease inhibitors may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S and the configuration at the chiral center is not defined by other means, either configuration can be present or a mixture of both configurations is present.

"Racemate" or "racemic mixture" means a compound of equimolar quantities of two enantiomers, wherein such mixtures exhibit no optical activity; i.e., they do not rotate the plane of polarized light.

"R" and "S" indicate configurations relative to the core molecule.

"⁓" represents "⋯⋯", "◀━" or "—", wherein the depicted enantiomer (e.g., "⋯⋯" or "◀━") is at least 60%, 70%, 80%, 90%, 99% or 99.9% optically pure.

The disclosed aspartic protease inhibitors may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed aspartic protease inhibitor is named or depicted by structure, the named or depicted stereoisomer is at least 60%, 70%, 80%, 90%, 99% or 99.9% by weight pure relative to the other stereoisomers.

When a single enantiomer is named or depicted by structure, the depicted or named enantiomer is at least 60%, 70%, 80%, 90%, 99% or 99.9% optically pure. Percent optical purity by weight is the ratio of the weight of the enantiomer over the weight of the enantiomer plus the weight of its optical isomer.

When a disclosed aspartic protease inhibitor is named or depicted by structure without indicating the stereochemistry, and the inhibitor has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer.

When a disclosed aspartic protease inhibitor is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

Pharmaceutically acceptable salts of the compounds of the aspartic protease inhibitors are included in the present invention. For example, an acid salt of an aspartic protease inhibitor containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of aspartic protease inhibitors containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

In accordance with the present invention, non-pharmaceutically acceptable salts of the compounds of the aspartic protease inhibitors and their synthetic intermediates are also included. These salts (for example, TFA salt) may be used, for example, for purification and isolation of the compounds of the aspartic protease inhibitors and their synthetic intermediates.

When a disclosed aspartic protease inhibitor is named or depicted by structure, it is to be understood that solvates (e.g., hydrates) of the aspartic protease inhibitor are also included.

"Solvates" refer to crystalline forms wherein solvent molecules are incorporated into the crystal lattice during crystallization. Solvates may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

When a disclosed aspartic protease inhibitor is named or depicted by structure, it is to be understood that the compound or its pharmaceutically acceptable salt, including solvates thereof, may exist in crystalline forms, non-crystalline forms or a mixture thereof. The aspartic protease inhibitor or solvates may also exhibit polymorphism (i.e. the capacity to occur in different crystalline forms). These different crystalline forms are typically known as "polymorphs." It is to be understood that when named or depicted by structure, the disclosed aspartic protease inhibitors and their solvates (e.g., hydrates) also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

It may be necessary and/or desirable during synthesis to protect sensitive or reactive groups on any of the molecules concerned. Representative conventional protecting groups are described in T. W. Greene and P. G. M. Wuts "Protective Groups in Organic Synthesis" John Wiley & Sons, Inc., New York 1999, and the entire teaching of which is herein incorporated by reference. Protecting groups may be added and removed using methods well known in the art.

The compounds of the invention are useful for ameliorating or treating disorders or diseases in which decreasing the levels of aspartic protease products is effective in treating the disease state or in treating infections in which the infectious agent depends upon the activity of an aspartic protease. In hypertension elevated levels of angiotensin I, the product of renin catalyzed cleavage of angiotensinogen are present. Thus, the compounds of the invention can be used in the treatment of hypertension, heart failure such as (acute and chronic) congestive heart failure; left ventricular dysfunction; cardiac hypertrophy; cardiac fibrosis; cardiomyopathy (e.g., diabetic cardiac myopathy and post-infarction cardiac myopathy); supraventricular and ventricular arrhythmias; arial fibrillation; atrial flutter; detrimental vascular remodeling; myocardial infarction and its sequelae; atherosclerosis; angina (whether unstable or stable); renal failure conditions, such as diabetic nephropathy; glomerulonephritis; renal fibrosis; scleroderma; glomerular sclerosis; microvascular complications, for example, diabetic retinopathy; renal vascular hypertension; vasculopathy; neuropathy; complications resulting from diabetes, including nephropathy, vasculopathy, retinopathy and neuropathy, diseases of the coronary vessels, proteinuria, albumenuria, post-surgical hypertension, metabolic syndrome, obesity, restenosis following angioplasty, eye diseases and associated abnormalities including raised intra-ocular pressure, glaucoma, retinopathy, abnormal vascular growth and remodelling, angiogenesis-related disorders, such as neovascular age related macular degeneration; hyperaldosteronism, anxiety states, and cognitive disorders (Fisher N. D.; Hollenberg N. K. *Expert Opin. Investig. Drugs*. 2001, 10, 417-26).

Elevated levels of βamyloid, the product of the activity of the well-characterized aspartic protease β-secretase (BACE) activity on amyloid precursor protein, are widely believed to be responsible for the development and progression of amyloid plaques in the brains of Alzheimer's disease patients. The secreted aspartic proteases of *Candida albicans* are associated with its pathogenic virulence (Naglik, J. R.; Challacombe, S. J.; Hube, B. *Microbiology and Molecular Biology Reviews* 2003, 67, 400-428). The viruses HIV and HTLV depend on their respective aspartic proteases for viral maturation. *Plasmodium falciparum* uses plasmepsins I and II to degrade hemoglobin.

A pharmaceutical composition of the invention may, alternatively or in addition to a disclosed aspartic protease inhibitor, comprise a prodrug or pharmaceutically active metabolite of such a compound or salt and one or more pharmaceutically acceptable carriers or diluent therefor.

The invention includes a therapeutic method for treating or ameliorating an aspartic protease mediated disorder in a subject in need thereof comprising administering to a subject in need thereof an effective amount of an aspartic protease inhibitor disclosed herein.

Administration methods include administering an effective amount of a compound or composition of the invention at different times during the course of therapy or concurrently in a combination form. The methods of the invention include all known therapeutic treatment regimens.

"Effective amount" means that amount of drug substance (i.e. aspartic protease inhibitors of the present invention) that elicits the desired biological response in a subject. Such response includes alleviation of the symptoms of the disease or disorder being treated. The effective amount of a disclosed aspartic protease inhibitor in such a therapeutic method is from about 0.01 mg/kg/day to about 10 mg/kg/day, preferably from about 0.5 mg/kg/day to 5 mg/kg/day.

The invention includes the use of a disclosed aspartic protease inhibitor for the preparation of a composition for treating or ameliorating an aspartic protease mediated chronic disorder or disease or infection in a subject in need thereof, wherein the composition comprises a mixture of one or more of the disclosed aspartic protease inhibitors and an optional pharmaceutically acceptable carrier.

"Pharmaceutically acceptable carrier" means compounds and compositions that are of sufficient purity and quality for use in the formulation of a composition of the invention that, when appropriately administered to an animal or human, do not produce an adverse reaction, and that are used as a vehicle for a drug substance (i.e. aspartic protease inhibitors of the present invention).

"Pharmaceutically acceptable diluent" means compounds and compositions that are of sufficient purity and quality for use in the formulation of a composition of the invention that, when appropriately administered to an animal or human, do not produce an adverse reaction, and that are used as a diluting agent for a drug substance (i.e. aspartic protease inhibitors of the present invention).

"Aspartic protease mediated disorder or disease" includes disorders or diseases associated with the elevated expression or overexpression of aspartic proteases and conditions that accompany such diseases.

An embodiment of the invention includes administering an aspartic protease inhibitor disclosed herein in a combination therapy (see U.S. Pat. No. 5,821,232, U.S. Pat. No. 6,716,875, U.S. Pat. No. 5,663,188, Fossa, A. A.; DePasquale, M. J.; Ringer, L. J.; Winslow, R. L. "Synergistic effect on reduction in blood pressure with coadministration of a renin inhibitor or an angiotensin-converting enzyme inhibitor with an angiotensin II receptor antagonist" *Drug Development Research* 1994, 33(4), 422-8, the aforementioned article and patents are hereby incorporated by reference) with one or more additional agents for the treatment of hypertension including α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist.

α-Blockers include doxazosin, prazosin, tamsulosin, and terazosin.

β-Blockers for combination therapy are selected from atenolol, bisoprol, metoprolol, acetutolol, esmolol, celiprolol, taliprolol, acebutolol, oxprenolol, pindolol, propanolol, bupranolol, penbutolol, mepindolol, carteolol, nadolol, carvedilol, and their pharmaceutically acceptable salts.

Calcium channel blockers include dihydropyridines (DHPs) and non-DHPs. The preferred DHPs are selected from the group consisting of amlodipine, felodipine, ryosidine, isradipine, lacidipine, nicardipine, nifedipine, nigulpidine, niludipine, nimodiphine, nisoldipine, nitrendipine, and nivaldipine and their pharmaceutically acceptable salts. Non-DHPs are selected from flunarizine, prenylamine, diltiazem, fendiline, gallopanil, mibefradil, anipamil, tiapamil, and verampimil and their pharmaceutically acceptable salts.

A diuretic is, for example, a thiazide derivative selected from amiloride, chlorothiazide, hydrochlorothiazide, methylchlorothiazide, and chlorothalidon.

Centrally acting antihypertensives include clonidine, guanabenz, guanfacine and methyldopa.

ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril.

Dual ACE/NEP inhibitors are, for example, omapatrilat, fasidotril, and fasidotrilat.

Preferred ARBs include candesartan, eprosartan, irbesartan, losartan, olmesartan, tasosartan, telmisartan, and valsartan.

Preferred aldosterone synthase inhibitors are anastrozole, fadrozole, and exemestane.

Preferred aldosterone-receptor antagonists are spironolactone and eplerenone.

A preferred endothelin antagonist is, for example, bosentan, enrasentan, atrasentan, darusentan, sitaxentan, and tezosentan and their pharmaceutically acceptable salts.

An embodiment of the invention includes administering an aspartic protease inhibitor disclosed herein or composition thereof in a combination therapy with one or more additional agents for the treatment of AIDS reverse transcriptase inhibitors, non-nucleoside reverse transcriptase inhibitors, other HIV protease inhibitors, HIV integrase inhibitors, entry inhibitors (including attachment, co-receptor and fusion inhibitors), antisense drugs, and immune stimulators.

Preferred reverse transcriptase inhibitors are zidovudine, didanosine, zalcitabine, stavudine, lamivudine, abacavir, tenofovir, and emtricitabine.

Preferred non-nucleoside reverse transcriptase inhibitors are nevirapine, delaviridine, and efavirenz.

Preferred HIV protease inhibitors are saquinavir, ritonavir, indinavir, nelfinavir, amprenavir, lopinavir, atazanavir, and fosamprenavir.

Preferred HIV integrase inhibitors are L-870,810 and S-1360.

Entry inhibitors include compounds that bind to the CD4 receptor, the CCR5 receptor or the CXCR4 receptor. Specific examples of entry inhibitors include enfuvirtide (a peptidomimetic of the HR2 domain in gp41) and sifurvitide.

A preferred attachment and fusion inhibitor is enfuvirtide.

An embodiment of the invention includes administering an aspartic protease inhibitor disclosed herein or composition thereof in a combination therapy with one or more additional agents for the treatment of Alzheimer's disease including tacrine, donepezil, rivastigmine, galantamine, and memantine.

An embodiment of the invention includes administering an aspartic protease inhibitor disclosed herein or composition thereof in a combination therapy with one or more additional agents for the treatment of malaria including artemisinin, chloroquine, halofantrine, hydroxychloroquine, mefloquine, primaquine, pyrimethamine, quinine, sulfadoxine.

Combination therapy includes co-administration of an aspartic protease inhibitor disclosed herein and said other agent, sequential administration of the disclosed aspartic protease inhibitor and the other agent, administration of a composition containing the aspartic protease inhibitor and the other agent, or simultaneous administration of separate compositions containing the aspartic protease inhibitor and the other agent.

The invention further includes the process for making the composition comprising mixing one or more of the disclosed aspartic protease inhibitors and an optional pharmaceutically acceptable carrier; and includes those compositions resulting from such a process, which process includes conventional pharmaceutical techniques. For example, an aspartic protease inhibitor disclosed herein may be nanomilled prior to formulation. An aspartic protease inhibitor disclosed herein may also be prepared by grinding, micronizing or other particle size reduction methods known in the art. Such methods include, but are not limited to, those described in U.S. Pat. Nos. 4,826,689, 5,145,684, 5,298,262, 5,302,401, 5,336,507, 5,340,564, 5,346,702, 5,352,459, 5,354,560, 5,384,124, 5,429,824, 5,503,723, 5,510,118, 5,518,187, 5,518,738, 5,534,270, 5,536,508, 5,552,160, 5,560,931, 5,560,932, 5,565,188, 5,569,448, 5,571,536, 5,573,783, 5,580,579, 5,585,108, 5,587,143, 5,591,456, 5,622,938, 5,662,883, 5,665,331, 5,718,919, 5,747,001, PCT applications WO 93/25190, WO 96/24336, and WO 98/35666, each of which is incorporated herein by reference. The pharmaceutical compositions of the invention may be prepared using techniques and methods known to those skilled in the art. Some of the methods commonly used in the art are described in *Remington's Pharmaceutical Sciences* (Mack Publishing Company), the entire teachings of which are incorporated herein by reference.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration occularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The dosage form containing the composition of the invention contains an effective amount of the drug substance (i.e. aspartic protease inhibitors of the present invention) necessary to provide a therapeutic and/or prophylactic effect. The composition may contain from about 5,000 mg to about 0.5 mg (preferably, from about 1,000 mg to about 0.5 mg) of a disclosed aspartic protease inhibitor or salt form thereof and may be constituted into any form suitable for the selected mode of administration. The compositions of the invention may be administered in a form suitable for once-weekly or once-monthly administration. For example, an insoluble salt of the drug substance (i.e. aspartic protease inhibitors of the present invention) may be adapted to provide a depot preparation for intramuscular injection (e.g., a decanoate salt) or to provide a solution for ophthalmic administration. Daily administration or post-periodic dosing may also be employed, wherein the composition may be administered about 1 to about 5 times per day.

For oral administration, the composition is preferably in the form of a tablet or capsule containing, e.g., 1000 to 0.5 milligrams of the drug substance (i.e. aspartic protease inhibitors of the present invention), more specifically 500 mg to 5 mg. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the drug substance (i.e. aspartic protease inhibitors of the present invention) is dispersed evenly throughout the mixture, which may be readily subdivided into dosage units containing equal amounts of a disclosed aspartic protease inhibitor. Preferably, the compositions are prepared by mixing a disclosed aspartic protease inhibitor with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binding agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

The disclosed aspartic protease inhibitors may also be administered via a slow release composition, wherein the composition includes a disclosed aspartic protease inhibitor and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an drug substance(s) (i.e. aspartic protease inhibitors of the present invention) and which slowly degrade/dissolve in a suitable environment (e.g., aqueous, acidic, basic and the like) to release the drug substance(s). Such particles degrade/dissolve in body fluids to release the drug substance(s) (i.e. aspartic protease inhibitors of the present invention) therein. The particles are preferably nanoparticles (e.g., in the range of about 1 to 500 nm in diameter, preferably about 50-200 nm in diameter, and most preferably about 100 nm in diameter). In a process for preparing a slow release composition, a slow release carrier and a disclosed aspartic protease inhibitor are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the disclosed aspartic protease inhibitor.

The disclosed aspartic protease inhibitors may be incorporated for administration orally or by injection in a liquid form, such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The disclosed aspartic protease inhibitors may be administered parenterally via injection. A parenteral formulation may consist of the drug substance (i.e. aspartic protease inhibitors of the present invention) dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the drug substance (i.e.

aspartic protease inhibitors of the present invention) in the liquid carrier whereby the final dosage unit contains from 0.005 to 10% by weight of the drug substance (i.e. aspartic protease inhibitors of the present invention). Other additives include preservatives, isotonizers, solubilizers, stabilizers, and pain-soothing agents. Injectable suspensions may also be prepared, in which case appropriate liquid carriers, suspending agents and the like may be employed.

The disclosed aspartic protease inhibitors may be administered intranasally using a suitable intranasal vehicle.

The disclosed aspartic protease inhibitors may be also administered topically using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the disclosed aspartic protease inhibitor, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration in the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

The invention is further defined by reference to the examples, which are intended to be illustrative and not limiting.

Representative compounds of the invention can be synthesized in accordance with the general synthetic schemes described above and are illustrated in the examples that follow. The methods for preparing the various starting materials used in the schemes and examples are well within the knowledge of persons skilled in the art.

The following abbreviations have the indicated meanings:

| Abbreviation | Meaning |
|---|---|
| Aq | aqueous |
| Boc | tert-butoxy carbonyl or r-butoxy carbonyl |
| (Boc)$_2$O | di-tert-butyl dicarbonate |
| Brine | saturated aqueous NaCl |
| Cbz | Benzyloxycarbonyl |
| CbzCl | Benzyl chloroformate |
| CDI | carbonyl diimidazole |
| CH$_2$Cl$_2$ | methylene chloride |
| CH$_3$CN or MeCN | acetonitrile |
| Cpd | compound |
| d | day |
| DAMP | 4,4'-(2-pyridinylmethylene)diphenol acetate |
| DAST | diethylaminosulfur trifluoride |
| DBU | 1,8-diazabicyclo[5.4.0]undec-7-ene |
| DCC | N,N'-dicyclohexylcarbodiimide |
| DCM | dichloromethane |
| DCU | N,N'-dicyclohexylurea |
| DIAD | diisopropyl azodicarboxylate |
| DiBAlH | Diisobutylaluminum hydride |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPPA | Diphenylphosphoryl azide |
| EDCI•HCl | 1-[3-(dimethylamino)propyl]-3-ethylcarbodiimide hydrochloride |
| Equiv | equivalents |
| Et | ethyl |
| Et$_2$O | ethyl ether |
| EtOAc | ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazole-1-yl)-1,1,3,3-tetramethyluronium hexafluorophosphate |
| KHMDS | potassium hexamethyldisilazane |
| LiHMDS | lithium hexamethyldisilazane |
| LAB | lithium amidotrihydroborate |
| LAH or LiAlH$_4$ | lithium aluminum hydride |
| LC-MS | liquid chromatography-mass spectroscopy |
| LHMDS | lithium hexamethyldisilazane |
| Me | methyl |
| MeCN | acetonitrile |
| MeOH | methanol |
| MsCl | methanesulfonyl chloride |
| min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Ph | phenyl |
| PTSA | p-toluene sulfonic acid |
| R-CBS | (R)-CBS-oxazaborolidine |
| Quant | quantitative yield |
| rt | room temperature |
| Satd | saturated |
| SOCl$_2$ | thionyl chloride |
| SPE | solid phase extraction |
| TBDPSCl | tert-butyl diphenyl silyl chloride |
| TBME | tert-butyl methyl ether |
| TBS | t-butyldimethylsilyl |
| TBSCl | t-butyldimethylsilyl chloride |
| TEA | triethylamine or Et$_3$N |
| TEAF | tetraethylammonium fluoride |
| TEMPO | 2,2,6,6-tetramethyl-1-piperidinyloxy free radical |
| Teoc | 1-[2-(trimethylsilyl)ethoxycarbonyl] |
| Teoc-OSu | 1-[2-(trimethylsilyl)ethoxycarbonyloxy]pyrrolidin-2,5-dione |
| TFA | trifluoroacetic acid |
| THF | tetrahydrofuran |
| tlc | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |
| TsCl | p-toluenesulfonyl chloride |
| Red-Al | sodium bis(2-methoxyethoxy)aluminum dihydride |

EXAMPLE 1
General Synthetic Schemes
The compounds of present invention can be synthesized by coupling a pyran intermediate represented by the following structure:
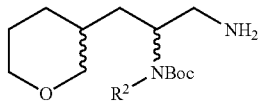
with a piperidine intermediate represented by the following structure:
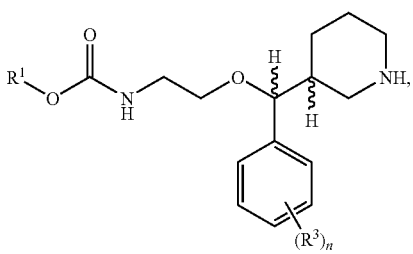
described in the following scheme:
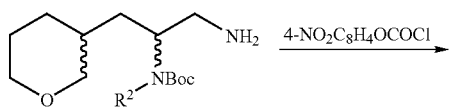
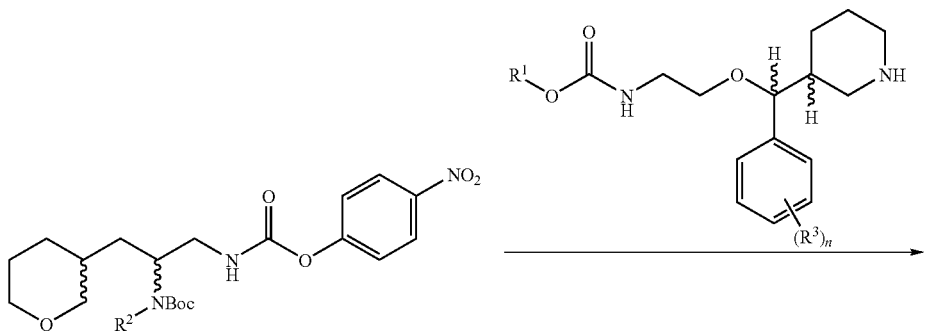
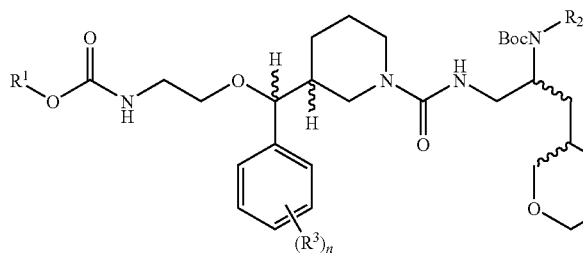
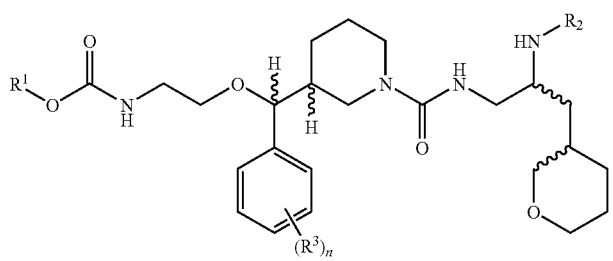

Preparation of the Pyran Intermediate from Glutamic Ester
The pyran intermediate can be prepared from glutamic ester using the following synthetic scheme:
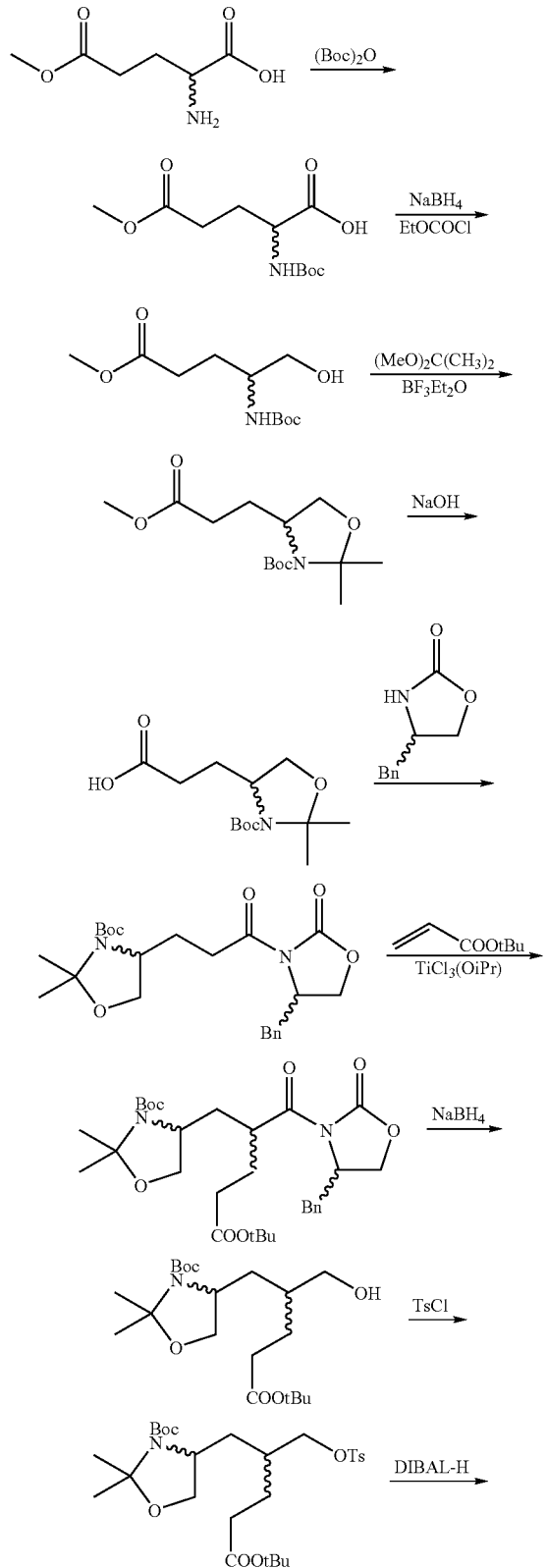
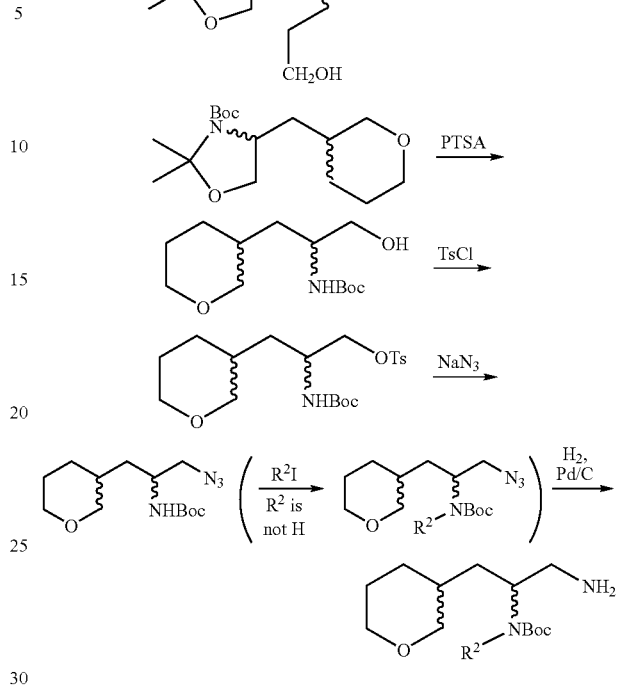
Preparation of the Pyran Intermediate from Pyroglutamic Ester
The pyran intermediate can also be prepared from pyroglutamic ester using the following synthetic scheme:
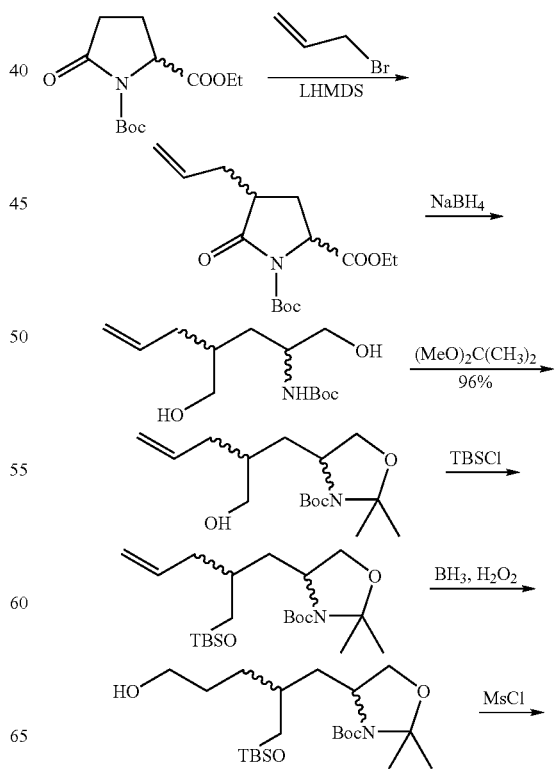

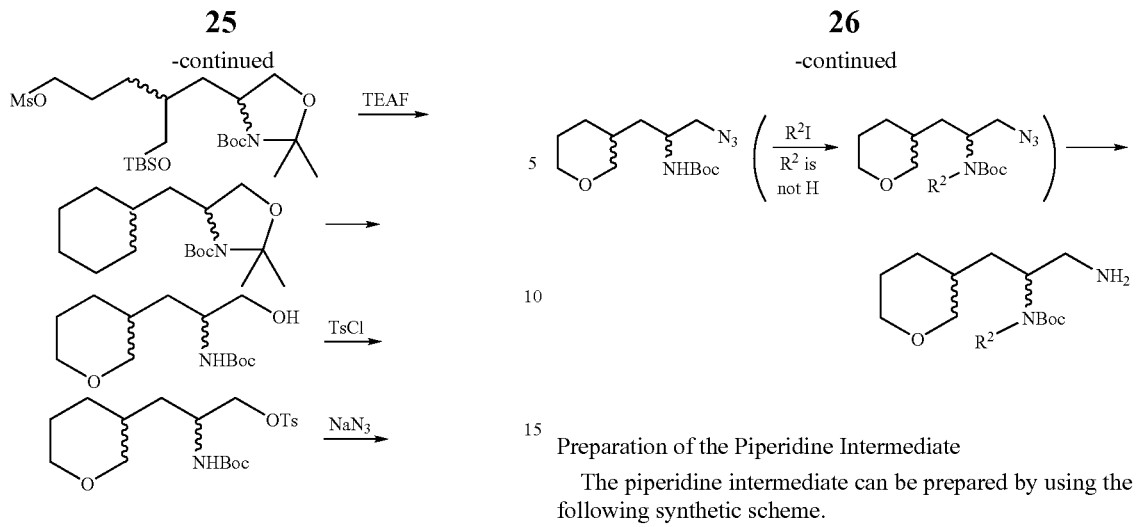
Preparation of the Piperidine Intermediate
The piperidine intermediate can be prepared by using the following synthetic scheme.
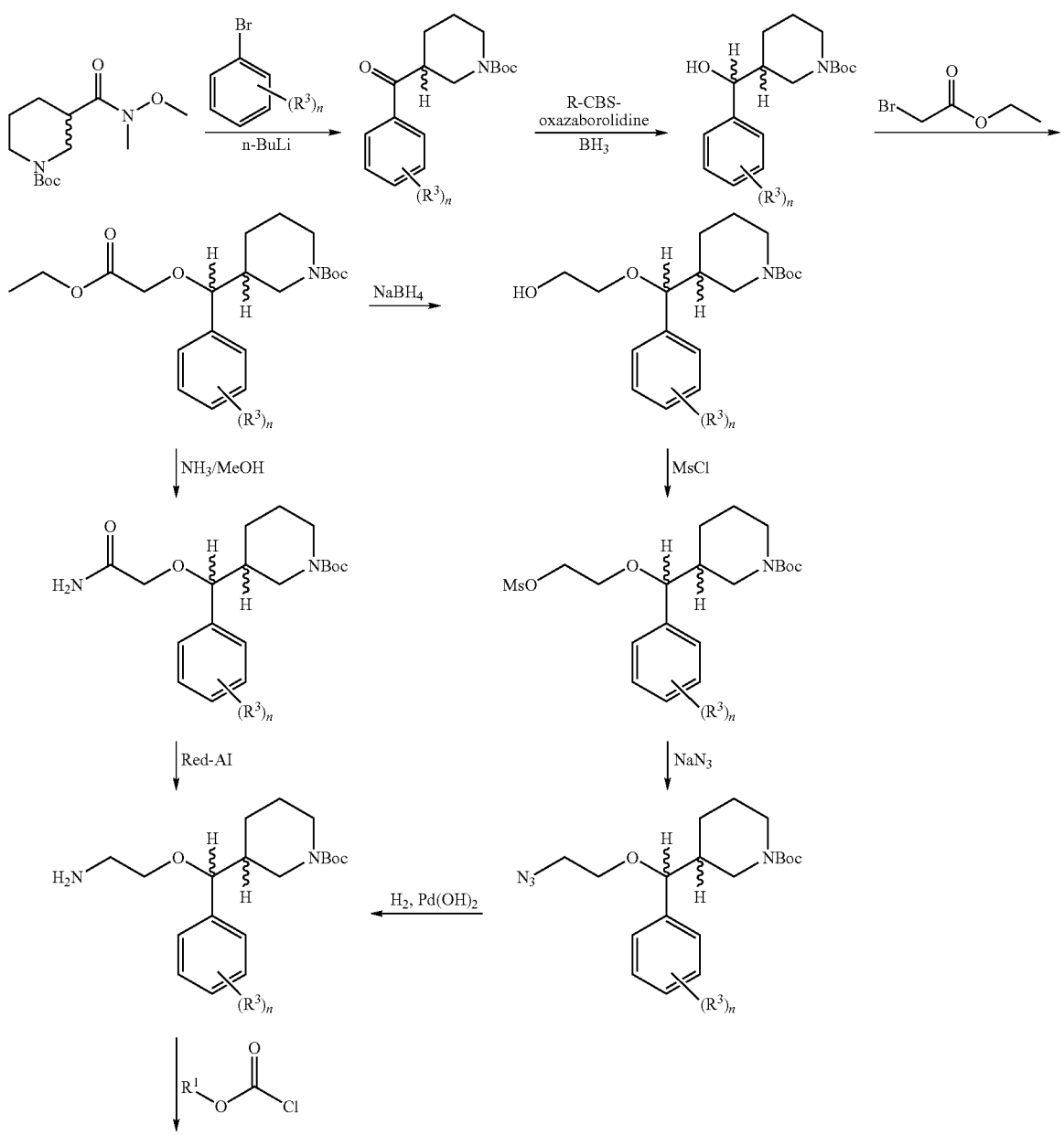

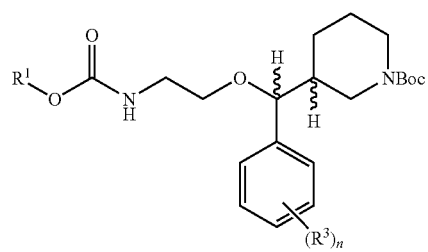
Alternatively, the piperidine intermediate can be prepared using the following synthetic scheme:
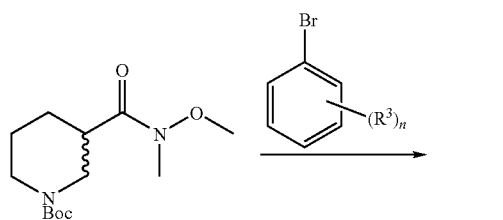
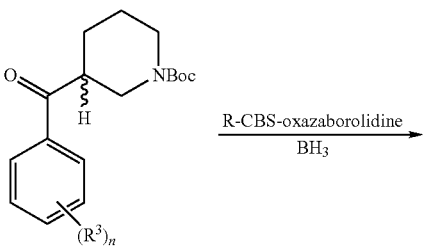
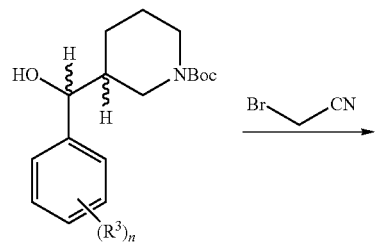
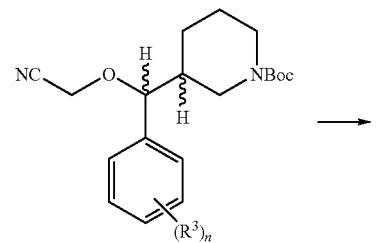
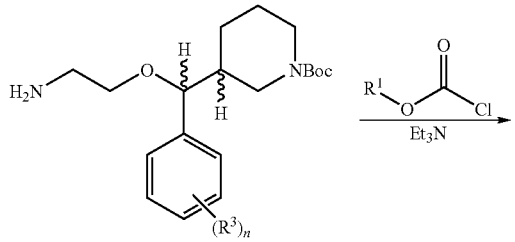
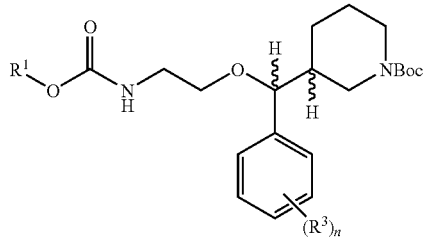
Specific conditions for synthesizing the disclosed aspartic protease inhibitors according to the above schemes are provided in Examples 2-11.
EXAMPLE 2
(R)-tert-butyl 3-((R)-(3-chlorophenyl)(2-(methoxycarbonylamino)ethoxy)methyl)piperidine-1-carboxylate
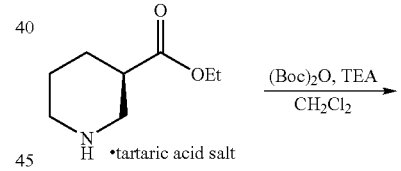
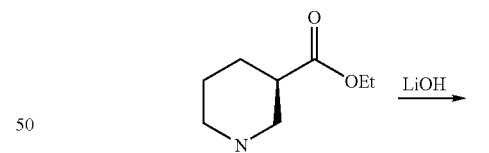
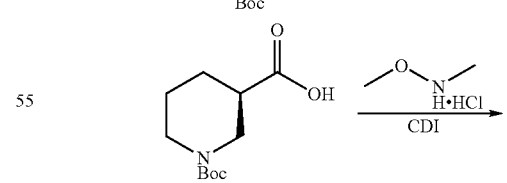
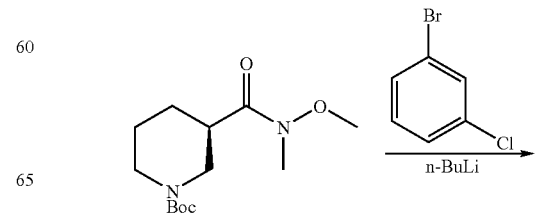

-continued

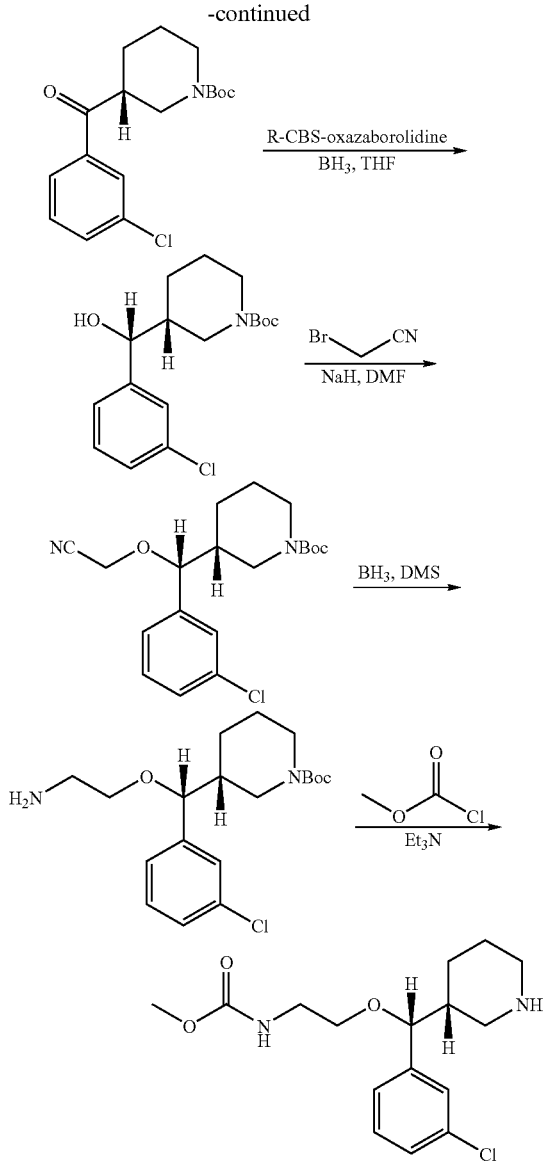

Step 1. (R)-1-tert-butyl 3-ethyl
piperidine-1,3-dicarboxylate

To a 20 L of round bottom flask was placed (R)-ethyl piperidine-3-carboxylate tartaric acid salt (2.6 kg, 8.47 mol, 1 eq) and CH$_2$Cl$_2$ (14 L). To the above solution, at 0° C. was added TEA (2.137 kg, 21.17 mol, 2.5 eq), followed by drop wise addition of (Boc)$_2$O (2.132 kg, 9.74 mol, 1.15 eq). The mixture was allowed to stir overnight at room temperature. The mixture was washed with saturated citric acid solution (3×2.5 L), saturated NaHCO$_3$ solution (3×2.5 L) and brine (2×2 L). The organic phase was dried over Na$_2$SO$_4$, filtered and the filtrate was evaporated to give colorless oil (2.2 kg, yield 100%).

Step 2.
(R)-1-(tert-butoxycarbonyl)piperidine-3-carboxylic acid

To a solution of (R)-1-tert-butyl 3-ethyl piperidine-1,3-dicarboxylate (2.2 kg, 8.469 mol, 1 eq) in 5 L of MeOH was added a solution of LiOH (629.6 g, 15 mol, 1.77 eq) in 7.5 L of water at 0-5° C. After addition, the mixture was stirred overnight at room temperature. TLC showed the starting material was consumed. The pH of the system was adjusted to 7 by addition of saturated citric acid solution. Most of the methanol was removed. The pH was adjusted to 4-5 with citric acid. The mixture was extracted 3 times with 5 L of CH$_2$Cl$_2$, the organic layers were combined and dried over Na$_2$SO$_4$ and evaporated to afford a white solid (1.775 kg, 92%).

Step 3. (R)-tert-butyl 3-(methoxy(methyl)carbamoyl)
piperidine-1-carboxylate

To a stirred solution of (R)-1-(tert-butoxycarbonyl)piperidine-3-carboxylic acid (233 g, 1.2 mol) in THF (1.2 L) was added carbonyldiimidazole (230 g, 1.42 mol). The mixture was stirred for 1 h under ice-water bath. A suspension of triethylamine (207 mL, 1.41 mol) and N,O-dimethylhydroxylamine hydrochloride (138 g, 1.42 mol) in THF (900 mL) was added. The reaction mixture was allowed to warm to room temperature and stirred overnight. TLC showed the reaction was complete. The solvent was evaporated, and the residue was dissolved in CH$_2$Cl$_2$ (1.2 L) and washed successively with 0.5 N hydrochloride solution, saturated solution of sodium carbonate and brine, dried over anhydrous sodium sulfate and evaporated to give crude compound (R)-tert-butyl 3-(methoxy(methyl)carbamoyl)piperidine-1-carboxylate (250 g, 91%), which was used in the next step directly without purification. $^1$H NMR (400 MHz, CDCl$_3$): 4.05-4.19 (m, 2H), 3.72 (s, 3H), 3.17 (s, 3H), 2.75-2.85 (m, 2H), 2.65 (t, 1H), 1.90 (d, 1H), 1.60-1.78 (m, 2H), 1.44 (s, 9H).

Step 4. (R)-tert-butyl
3-(3-chlorobenzoyl)piperidine-1-carboxylate

To a solution of 1-bromo-3-chlorobenzene (54.3 g, 0.286 mol) in anhydrous THF (500 mL) at −78° C. under nitrogen was added drop wise a solution of 2.5 M n-BuLi in hexane (114 mL, 0.286 mol). After stirring for 1 hr at −78° C., a solution of (R)-tert-butyl 3-(methoxy(methyl)carbamoyl)piperidine-1-carboxylate (65.8 g, 0.242 mol) in anhydrous THF (300 mL) was added drop wise. After addition, the reaction mixture was allowed to warm to room temperature and stirred for 2 h. TLC indicated the reaction was complete. The mixture was quenched with saturated NH$_4$Cl solution (300 mL) and extracted with ethyl acetate (3×200 mL). The combined organic layers were washed with brine, dried over Na$_2$SO$_4$ and concentrated in vacuo to give the crude product (R)-tert-butyl 3-(3-chlorobenzoyl)piperidine-1-carboxylate (92 g, 100%), which was used immediately for next step without purification.

Step 5. (R)-tert-butyl 3-((R)-(3-chlorophenyl)(hydroxy)methyl)piperidine-1-carboxylate To a solution of (R)-tert-butyl 3-(3-chlorobenzoyl)piperidine-1-carboxylate (92 g, 0.286 mol) in anhydrous THF (300 mL) at −15° C. under nitrogen was added drop wise a solution of 1 M R-CBS-oxazaborolidine in toluene (45 mL, 45 mmol, 0.15 eq). After stirring for 1 hr at −15° C., a solution of 10 M BH$_3$ in THF (33 mL, 0.33 mol, 1.1 eq) was added drop wise. After addition, the reaction mixture was stirred for 2 h at −15° C. TLC indicated the starting material was consumed. Methanol (200 mL) was added drop wise carefully at −15° C. The solvent was removed under reduced pressure, the residue was purified by column chromatography on silica gel eluting with AcOEt/hexane (1:30→1:15) to provide a light yellow oil (82 g, HPLC≧70%, ratio≧3:1). The mixture was dissolved in ethyl acetate until the alcohol was just dissolved (about 5 mL/1 g), the solvent was removed on the rotary evaporator until a few of crystals appeared. The solution was cooled to room temperature slowly and stood for 1-2 h. To the above solution was added hexane (about 300 mL) and then filtered, the crystals were washed with cool hexane and recrystallized another two times to afford (R)-tert-butyl 3-((R)-(3-chlorophenyl)(hydroxy)methyl)piperidine-1-carboxylate as the pure isomer (32.5 g, ee.≧99%, yield 35% for two steps).

Step 6. (R)-tert-butyl 3-((R)-(3-chlorophenyl)(cyanomethoxy)methyl)piperidine-1-carboxylate To a solution of (R)-tert-butyl 3-((R)-(3-chlorophenyl)(hydroxy)methyl)piperidine-1-carboxylate (32.5 g, 0.1 mol), NaH (12 g, 0.3 mol) was added at 0° C. The mixture was stirred for 1 h at room temperature. The mixture was cooled to 40° C., then bromoacetonitrile (35.7 g, 0.3 mol) was added drop wise. The mixture was stirred an additional 0.5 h at -20° C. HPLC indicated the reaction was ~30% complete. The addition of NaH and bromoacetonitrile was repeated two more times. HPLC indicated the reaction was ~60% completed. The reaction was quenched with sat. NH$_4$Cl. The mixture was extracted with CH$_2$Cl$_2$. The organic layer was dried over Na$_2$SO$_4$, concentrated to give the crude product as brown oil (36.8 g), which was used for the next step without purification.

Step 7. (R)-tert-butyl 3-((R)-(2-aminoethoxy)(3-chlorophenyl)methyl)piperidine 1-carboxylate (R)-tert-butyl 3-((R)-(3-chlorophenyl)(cyanomethoxy)methyl)piperidine-1-carboxylate (36.8 g, 0.10 mol) was dissolved in anhydrous THF (350 mL), and the solution was heated under reflux under a nitrogen atmosphere. A solution of BH$_3$.Me$_2$S (30 mL, 0.30 mol) in THF was added drop wise, and stirring was continued under reflux overnight. The resulting solution was cooled to room temperature. The reaction was quenched by careful, drop wise addition of MeOH until bubbling ceased. After evaporation of the solution, the crude product was obtained (70 g), which was used for the next step without purification.

Step 8. (R)-tert-butyl 3-((R)-(3-chlorophenyl)(2-(methoxycarbonylamino)ethoxy)methyl)piperidine-1-carboxylate To a solution of (R)-tert-butyl 3-((R)-(2-aminoethoxy)(3-chlorophenyl)methyl)piperidine-1-carboxylate (70 g, crude, 0.1 mol) and DMAP (1.83 g, 15 mmol, 0.15 eq) in dry CH$_2$Cl$_2$ (150 mL), Et$_3$N (12.1 g, 15.8 mL, 120 mmol) was added. The resulting mixture was cooled to 0~5° C. using a ice-water bath, a solution of methyl chloroformate (11.28 g, 120 mmol, 1.2 eq) in dry CH$_2$Cl$_2$ (100 mL) was added drop wise. After addition, the reaction mixture was stirred for 3 h at 0~5° C. TLC showed the starting material had disappeared. Water (80 mL) was added. The aqueous layer was extracted with CH$_2$Cl$_2$ (3×100 mL), the combined organic layers were washed with 10% citric acid (2×150 mL) and brine (100 mL), then dried over Na$_2$SO$_4$, filtered and concentrated to the crude product, which was purified by preparative HPLC to afford (R)-tert-butyl 3-((R)-(3-chlorophenyl)(2-(methoxycarbonylamino)-methyl)piperidine-1-carboxylate (10.7 g, the total yield for three steps is 25%). $^1$H NMR (400 MHz, CDCl$_3$):1.12-1.40 (m, 4H), 1.43 (s, 9H), 1.64 (m, 2H), 2.82 (m, 2H), 3.25 (m, 2H), 3.61 (s, 3H), 3.74 (m, 1H), 4.05 (m, 1H), 4.16 (m, 1H), 7.22 (m, 1H), 7.32 (m, 3H).

Step 9. methyl 2-((R)-(3-chlorophenyl)((R)-piperidin-3-yl)methoxy)ethylcarbamate (R)-tert-butyl 3-((R)-(3-chlorophenyl)(2-(methoxycarbonylamino)-ethoxy)methyl)piperidine-1-carboxylate (10.7 g, 25 mmol) was dissolved in a solution of 20% (V/V) TFA/CH$_2$Cl$_2$ (150 mL). The reaction mixture was stirred at room temperature for 1 h. TLC showed the reaction was completed. A solution of saturated sodium bicarbonate was added drop wise to adjust pH 8-9. The resulting mixture was extracted with CH$_2$Cl$_2$ (3×200 mL), washed with brine, dried over Na$_2$SO$_4$, concentrated in vacuo to afford methyl 2-((R)-(3-chlorophenyl)((R)-piperidin-3-yl)methoxy)ethylcarbamate (11.2 g, 100%), which was used for next step directly without purification.

Alternatively, (R)-tert-butyl 3-((R)-(3-chlorophenyl)(2-(methoxycarbonylamino)ethoxy)methyl)piperidine-1-carboxylate may be prepared by the following procedures:

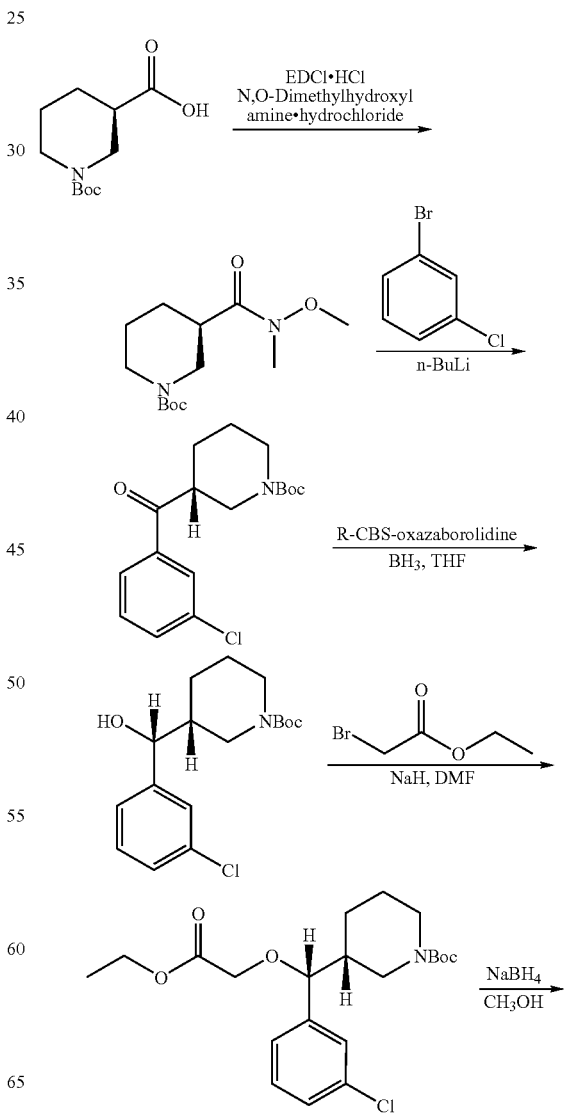

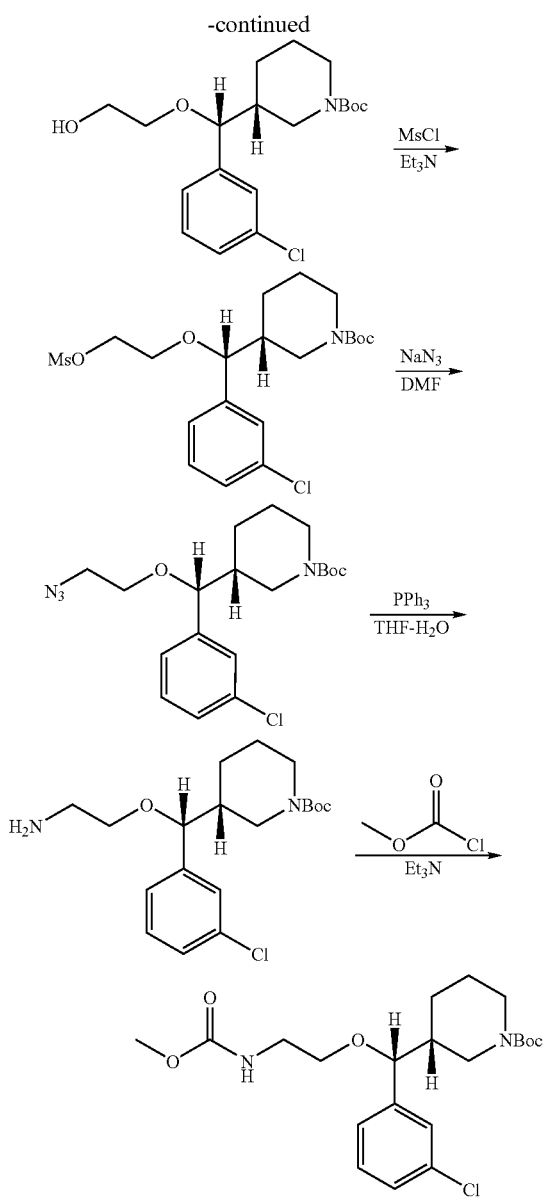

Step 1. (R)-tert-butyl 3-(methoxy(methyl)carbamoyl)piperidine-1-carboxylate (R)-1-(tert-Butoxycarbonyl)piperidine-3-carboxylic acid (25 g, 0.11 mol, 1.0 equiv), N,O-dimethylhydroxylamine hydrochloride, (10.5 g, 0.14 mol, 1.25 equiv) and EDCI.HCl (26.3 g, 0.14 mol, 1.25 equiv) and diisopropylethylamine (48 mL, 0.28 mol, 2.5 equiv) were dissolved in dichloromethane (400 mL) and stirred overnight at rt. The reaction mixture was diluted with EtOAc, washed with 5% aq HCl (2×150 mL), satd aq NaHCO$_3$ (150 mL), brine (100 mL), and dried over Na$_2$SO$_4$. Concentration afforded (R)-tert-butyl 3-(methoxy(methyl)carbamoyl)piperidine-1-carboxylate (24.42 g, 82%) as a clear oil. The crude product was used for next step without further purification. MS ESI+ve m/z 295 (M+Na). $^1$H NMR (CDCl$_3$) δ 4.19-4.00 (m, 2H), 3.77 (m, 3H), 3.12 (s, 3H), 2.79 (m, 2H), 2.64 (m, 1H), 1.89 (m, 1H), 1.71-1.52 (m, 2H), 1.51-1.33 (m, 10H).

Step 2. (R)-tert-butyl 3-(3-chlorobenzoyl)piperidine-1-carboxylate

To a solution of 1-bromo-3-chlorobenzene (100 g, 0.52 mol) in anhydrous THF (550 mL) at −78° C. under nitrogen was added dropwise a solution of 2.5 M n-BuLi in hexane (210 mL, 0.52 mol). After stirring for 1 hr at −78° C., a solution of (R)-tert-butyl 3-(methoxy(methyl)carbamoyl)piperidine-1-carboxylate (120 g, 0.44 mol) in anhydrous THF (500 mL) was added dropwise. After addition, the reaction mixture was allowed to warm to rt and stirred for 2 hr. The mixture was quenched with saturated NH$_4$Cl solution (500 mL) and extracted with EtOAc (3×400 mL). The combined organic layers were washed with brine, dried over Na$_2$SO$_4$ and concentrated in vacuo to give the crude (R)-tert-butyl 3-(3-chlorobenzoyl)piperidine-1-carboxylate (178 g), which was used immediately for next step without purification.

Step 3. (R)-tert-butyl 3-((R)-(3-chlorophenyl)(hydroxy)methyl)piperidine-1-carboxylate To a solution of (R)-tert-butyl 3-(3-chlorobenzoyl)piperidine-1-carboxylate (178 g, 0.55 mol) in anhydrous THF (600 mL) at −15° C. under nitrogen was added dropwise a solution of 1 M R-CBS-oxazaborolidine in toluene (82 mL, 82 mmol, 0.15 eq). After stirring for 1 hr at −15° C., a solution of 10 M BH$_3$ in THF (60 mL, 0.60 mol, 1.1 eq) was added dropwise. After addition, the reaction mixture was stirred for 2 hr at −15° C. Methanol (400 mL) was added dropwise carefully at −15° C. The solvent was removed under reduced pressure, the residue was purified by column chromatography on silica gel eluting with AcOEt/hexane (1:30→1:15) to provide the light yellow oil (95 g, HPLC purity≧70%, isomer ratio≧3:1). The mixture was dissolved in EtOAc till the alcohol was just dissolved (about 5 mL/1 g), the solvent was removed on the rotary evaporator until a few crystals appeared. The solution was cooled to rt slowly and stood for 1-2 hr. To the above solution was added hexane (about 300 mL) and then filtered, the crystals were washed with cool hexane and re-crystallized from AcOEt-hexane twice to afford the pure isomer (R)-tert-butyl 3-((R)-(3-chlorophenyl)(hydroxy)methyl)piperidine-1-carboxylate (20 g, ee≧99%).

Step 4. (R)-tert-butyl 3-((R)-(3-chlorophenyl)(2-ethoxy-2-oxoethoxy)methyl)piperidine-1-carboxylate To a suspension of NaH (7.44 g, 161 mmol) in anhydrous DMF (50 mL) at 0-5° C. was added dropwise a solution of (R)-tert-butyl 3-((R)-(3-chlorophenyl)(hydroxy)methyl)piperidine-1-carboxylate (17.45 g, 54 mmol) in anhydrous DMF (100 mL), the reaction mixture was stirred for 1 hr at rt. A solution of ethyl bromoacetate (17.82 g, 11.87 mL, 107 mmol) in anhydrous DMF (100 mL) was added dropwise to the above mixture at 0-5° C. After addition, the reaction mixture was stirred for 2-3 hr at rt. The reaction mixture was poured into saturated aqueous NH$_4$Cl and EtOAc (1000 mL) was added. The organic layer was washed with water (3×200 mL) and brine, dried over Na$_2$SO$_4$, filtered and concentrated in vacuo. The residue was purified on silica gel chromatography to afford (R)-tert-butyl 3-((R)-(3-chlorophenyl)(2-ethoxy-2-oxoethoxy)methyl)piperidine-1-carboxylate (14 g, 64% yield).

Step 5. (R)-tert-butyl 3-((R)-(3-chlorophenyl)(2-hydroxyethoxy)methyl)piperidine-1-carboxylate To a solution of (R)-tert-butyl 3-((R)-(3-chlorophenyl)(2-ethoxy-2-oxoethoxy)methyl)piperidine-1-carboxylate (14 g, 34 mmol) in MeOH (200 mL) was added NaBH₄ (10.35 g, 272 mmol) in portions while the temperature was lower than 40° C. After addition, the mixture was stirred at rt for 2-3 hr. The solvent was removed in vacuo to provide a residue which was partitioned between water and EtOAc. The organic layer was washed with H₂O and brine, dried over Na₂SO₄ and evaporated to give the crude (R)-tert-butyl 3-((R)-(3-chlorophenyl)(2-hydroxyethoxy)methyl)piperidine-1-carboxylate (12.50 g), which was used in the next step without purification.

Step 6. (R)-tert-butyl 3-((R)-(3-chlorophenyl)(2-(methylsulfonyloxy)ethoxy)methyl)piperidine-1-carboxylate To a solution of (R)-tert-butyl 3-((R)-(3-chlorophenyl)(2-hydroxyethoxy)methyl)piperidine-1-carboxylate (12.50 g, 34 mmol) in dry CH₂Cl₂ (150 mL) was added Et₃N (13.74 g, 18.3 mL, 136 mmol, 4 eq) at −5-0° C. Then a solution of MsCl (7.75 g, 5.16 mL, 68 mmol, 2 eq) in dry CH₂Cl₂ (50 mL) was added dropwise at the same temperature. After addition, it was allowed to warm to rt gradually. Upon reaction completion water (100 mL) was added. The aqueous layer was extracted with CH₂Cl₂ (3×80 mL), the combined organic layers was washed with 10% citric acid, sat. NaHCO₃ and brine, then dried over Na₂SO₄, filtered and concentrated to give (R)-tert-butyl 3-((R)-(3-chlorophenyl)(2-(methylsulfonyloxy)ethoxy)methyl)piperidine-1-carboxylate (15 g), which was used in the next step without purification.

Step 7. (R)-tert-butyl 3-((R)-(2-azidoethoxy)(3-chlorophenyl)methyl)piperidine-1-carboxylate (R)-tert-butyl 3-((R)-(3-chlorophenyl)(2-(methylsulfonyloxy)ethoxy)methyl)piperidine-1-carboxylate (15 g, 34 mmol) was dissolved into anhydrous DMF (150 mL), solid NaN₃ (6.7 g, 102 mmol, 3 eq) was added and the reaction mixture was heated to 80° C. for overnight. The reaction mixture was cooled to rt and then was added with EtOAc (500 mL), the organic phase was washed with water (3×100 mL) and brine (2×80 mL), dried over Na₂SO₄ and concentrated in vacuo to provide crude (R)-tert-butyl 3-((R)-(2-azidoethoxy)(3-chlorophenyl)methyl)piperidine-1-carboxylate (13.3 g), which was used for next step without purification.

Step 8. (R)-tert-butyl 3-((R)-(2-aminoethoxy)(3-chlorophenyl)methyl)piperidine-1-carboxylate (R)-tert-butyl 3-((R)-(2-azidoethoxy)(3-chlorophenyl)methyl)piperidine-1-carboxylate (13.3 g, 33.8 mmol) was dissolved in THF/H₂O (20:1, 180 mL/9 mL), triphenylphosphine (36.0 g, 135 mmol) was added in portions. The reaction mixture was stirred overnight at rt. The solvent was removed under reduced pressure to the residue, which was purified on silica gel chromatography to afford (R)-tert-butyl 3-((R)-(2-aminoethoxy)(3-chlorophenyl)methyl)piperidine-1-carboxylate (10.4 g, purity: HPLC=75%).

Step 9. (R)-tert-butyl 3-((R)-(3-chlorophenyl)(2-(methoxycarbonylamino)ethoxy)methyl)piperidine-1-carboxylate To a solution of (R)-tert-butyl 3-((R)-(2-aminoethoxy)(3-chlorophenyl)methyl)piperidine-1-carboxylate (7.7 g, 21 mmol, HPLC=75%) and DMAP (1.27 g, 10 mmol, 0.5 eq) in dry CH₂Cl₂ (120 mL), Et₃N (6.38 g, 8.45 mL, 63 mmol) was added. The resulting mixture was cooled to 0-5° C. under ice-water bath, a solution of methyl chloroformate (8.1 mL, 104.5 mmol, 5 eq) in dry CH₂Cl₂ (50 mL) was added dropwise. After addition, the reaction mixture was stirred for 1-2 hr at 0-5° C. The reaction was quenched with water (80 mL). The aqueous layer was extracted with CH₂Cl₂ (3×50 mL), the combined organic layers were washed with 10% citric acid (2×80 mL) and brine, then dried over Na₂SO₄, filtered and concentrated to the crude product, which was purified by preparative HPLC to afford (R)-tert-butyl 3-((R)-(3-chlorophenyl)(2-(methoxycarbonylamino)ethoxy)methyl)piperidine-1-carboxylate (4.4 g, HPLC≧98%, the total yield for five steps is 41%).

The following compounds were prepared following procedures analogous to those described above:
1) (R)-tert-butyl 3-((R)-(3,5-difluorophenyl)(2-(methoxycarbonylamino)ethoxy)methyl)piperidine-1-carboxylate using (3,5-difluorophenyl)lithium in Step 2.

Alternatively, (R)-tert-butyl 3-((R)-(2-aminoethoxy)(3-chlorophenyl)methyl)piperidine-1-carboxylate may be prepared by the following procedures:

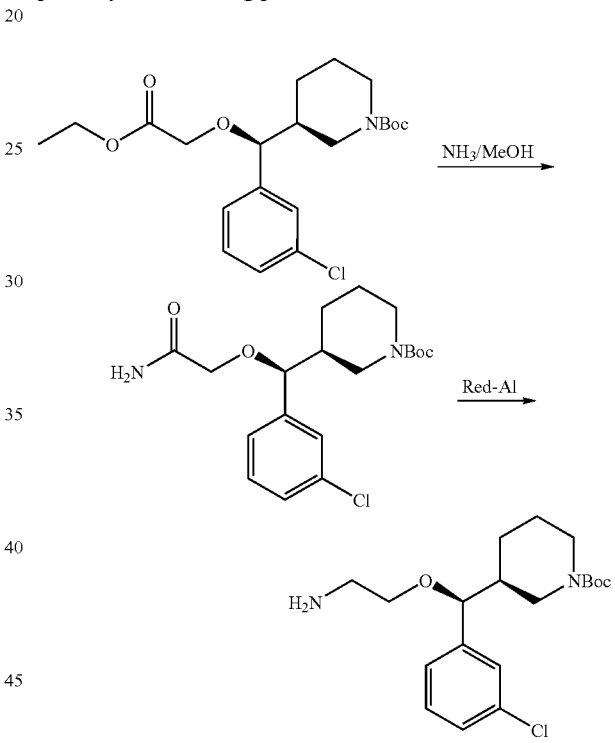

Step 1: Preparation of (R)-tert-butyl 3-((R)-(2-amino-2-oxoethoxy)(3-chlorophenyl)methyl)-piperidine-1-carboxylate (R)-tert-Butyl 3-((R)-(3-chlorophenyl)(2-ethoxy-2-oxoethoxy)methyl)-piperidine-1-carboxylate (0.971 g, 2.36 mmol) was dissolved in 7 M NH₃/MeOH (20 mL), and stirred overnight at room temperature. The solvent was removed under reduced pressure to give (R)-tert-butyl 3-((R)-(2-amino-2-oxoethoxy)(3-chlorophenyl)methyl)piperidine-1-carboxylate (902 mg, 100%), which was used for the next step without further purification. MS ESI+ve m/z 383 (M+H)⁺.

Step 2: Preparation of (R)-tert-butyl 3-((R)-(2-aminoethoxy)(3-chlorophenyl)methyl)-piperidine-1-carboxylate To a solution of (R)-tert-butyl 3-((R)-(2-amino-2-oxoethoxy)(3-chlorophenyl)methyl)piperidine-1-carboxylate (902 mg, 2.36 mmol) in anhydrous toluene (30 mL) at 0° C. was added Red-Al® (65% solution in toluene, 1.4 mL, 7.07 mmol) slowly over 10 min. After the addition, the solution was stirred overnight at room temperature. The reaction was cooled to 0° C. and quenched with Na₂SO₄.10H₂O. The resulting mixture was stirred for 2-3 h, filtered through Celite®, and washed with THF (200 mL). The filtrate was dried and concentrated to give crude product (R)-tert-butyl 3-((R)-(2-aminoethoxy)(3-chlorophenyl)methyl)piperidine-1-carboxylate (776 mg, 89%). MS ESI+ve m/z 369 (M+H)⁺.

Alternatively, (R)-tert-butyl 3-((R)-(2-aminoethoxy)(3-chlorophenyl)methyl)-piperidine-1-carboxylate may also be prepared by the following procedures:

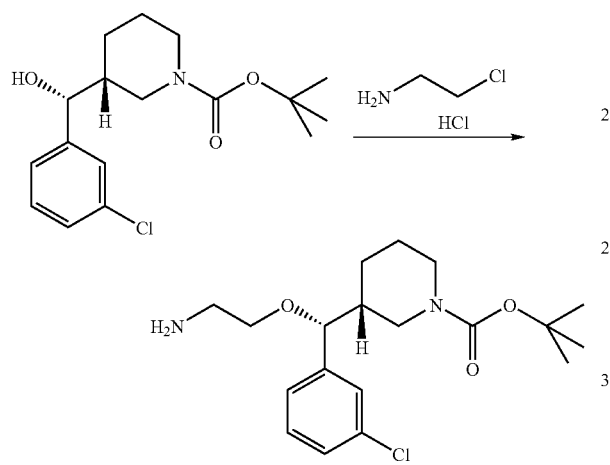

To a solution of (1.00 g, 3.07 mmol) (R)-tert-butyl 3-((R)-(3-chlorophenyl)(hydroxy)methyl)piperidine-1-carboxylate (98:2 diastereomeric ratio) in 10 ml (10 vol) of PhCF₃ was added, sequentially, 8.1 ml (50 eq) of a 50% by weight solution of NaOH in water, tetrabutylammonium hydrogensulfate (0.261 g, 0.25 eq), and chloroethylamine HCl (1.068 g, 3 eq), and stirred at 50° C. for a period of 20 h. HPLC analysis showed 88% conversion with minor impurities as well as approx. 9% starting alcohol. The reaction was allowed to cool to RT and the layers separate. The addition of 10 vol. of water was needed to ensure the clean separation of the layers. The organic layer was retained and rinsed with 10 vol brine. The organic layer was retained and concentrated under vacuum. The resulting residual oil was dissolved in 10 vol tert-butyl methyl ether (TBME) at which point 10 vol of a 20% weight solution of citric acid in water was added. (Note: tartaric acid works as well while acids such as HCl, oxalic acid, TsOH result in deprotection of the NBoc). HPLC analysis showed that clean extraction of the desired amine into the aq. layer had been achieved and the undesired starting alcohol was in the organic layer; the TBME layer was discarded. The aq. layer was rinsed once more with S vol of TBME in order to ensure the removal of the undesired starting alcohol. The organic TBME layer was discarded. The aq. layer was brought to a pH of approx. 13 by the addition of 2 vol of 50% weight NaOH in water at which point 10 vol DCM (dichloromethane) was added. Clean extraction of the desired product into the DCM was achieved. The organic extract was rinsed with 10 vol brine (no purification seen by HPLC), dried over NaSO4, and concentrated to afford 750 mg (66% yield, 97% purity) of the desired product (confirmed by HPLC/MS and NMR).

Alternatively, (R)-tert-butyl 3-((R)-(3-chlorophenyl)(2-(methoxycarbonylamino)ethoxy)methyl)piperidine-1-carboxylate may also be prepared by the following process:

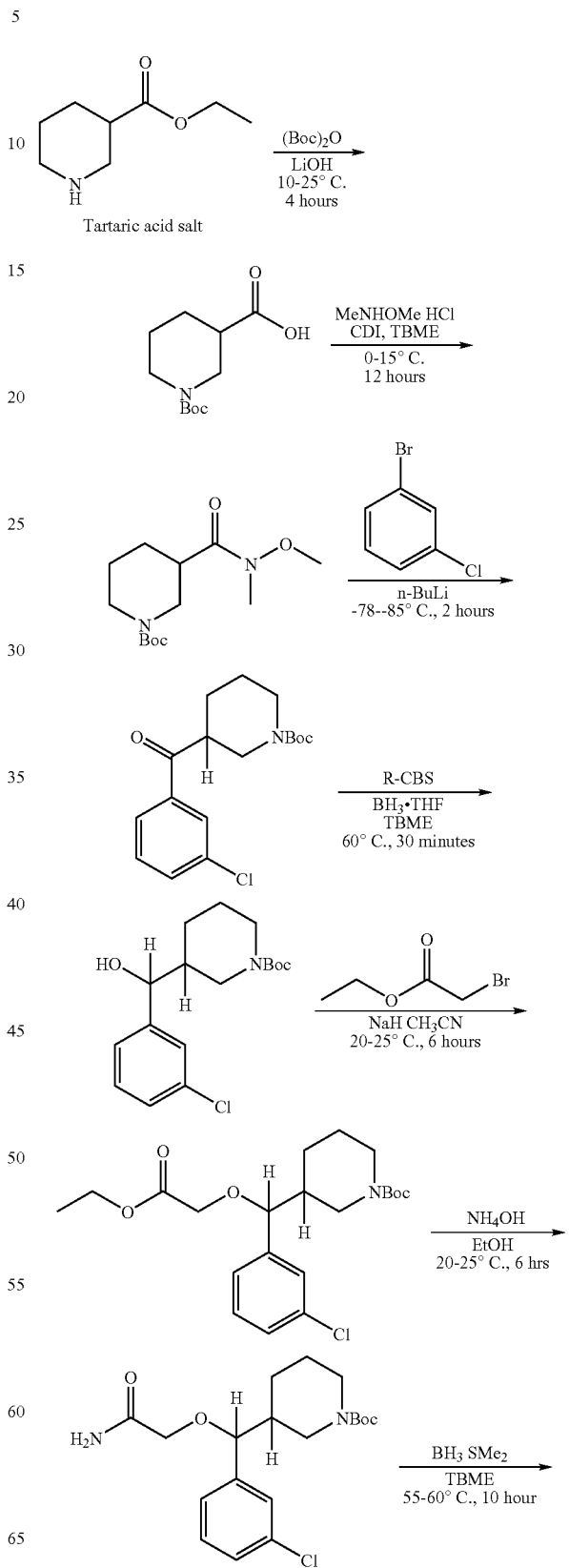

-continued

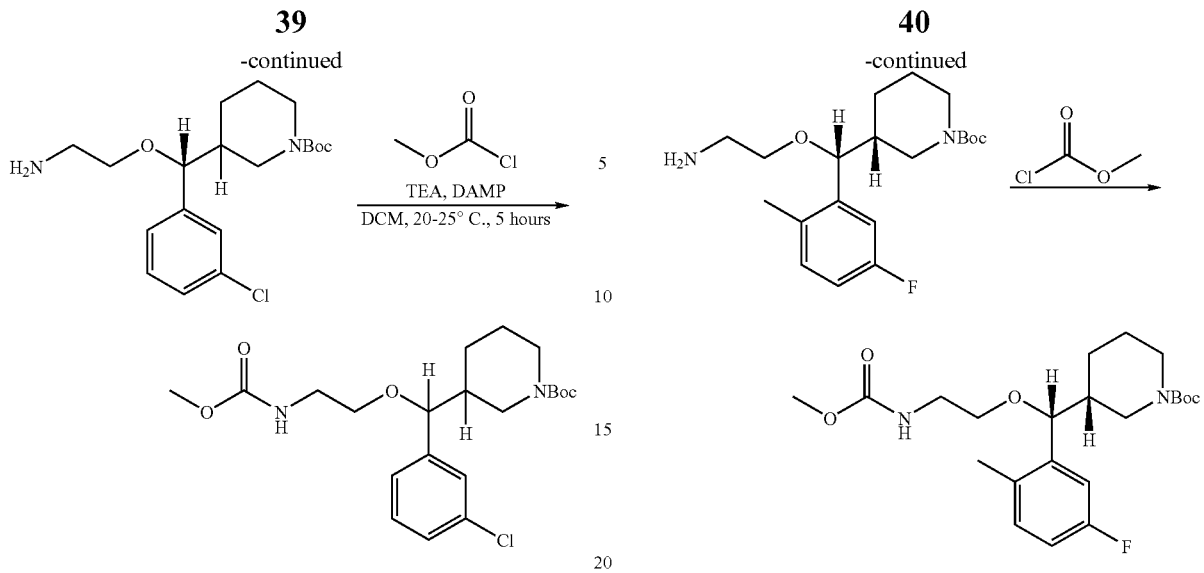

EXAMPLE 3

(R)-tert-butyl 3-((R)-(5-fluoro-2-methylphenyl)(2-(methoxycarbonylamino)ethoxy)methyl)piperidine-1-carboxylate

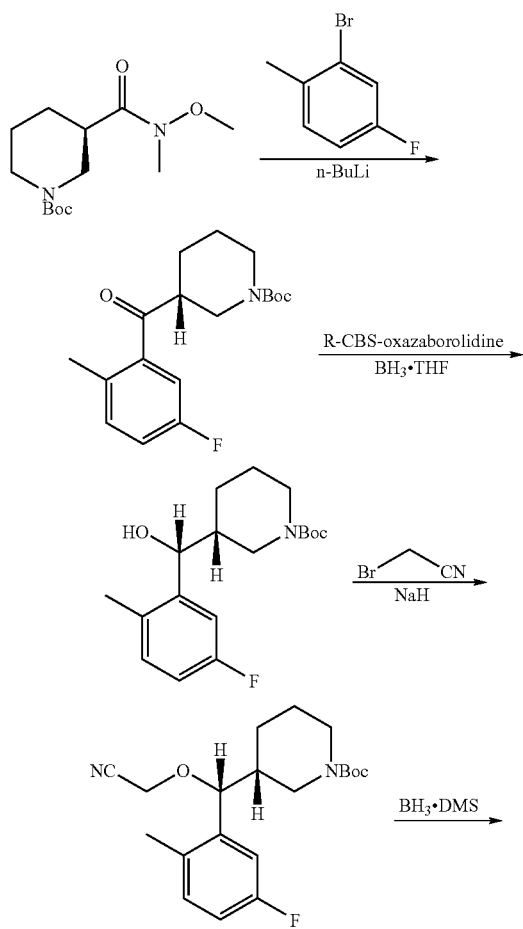

Step 1. (R)-tert-butyl 3-(5-fluoro-2-methylbenzoyl)piperidine-1-carboxylate

To a solution of 2-bromo-4-fluoro-1-methylbenzene (10.6 g, 0.056 mol) in anhydrous THF (150 mL) at −78° C. under nitrogen was added dropwise a solution of 2.5 M n-BuLi in hexane (22 mL, 0.056 mol). After stirring for 1 hr at −78° C., a solution of (R)-tert-butyl 3-(methoxy(methyl)carbamoyl)piperidine-1-carboxylate (10 g, 0.037 mol) in anhydrous THF (120 mL) was added dropwise. After addition, the reaction mixture was allowed to warm to rt and stirred for 2 hr. The mixture was quenched with saturated NH$_4$Cl (100 mL) solution and extracted with EtOAc (3×80 mL). The combined organic layers were washed with brine, dried over Na$_2$SO$_4$ and concentrated in vacuo to provide crude (R)-tert-butyl 3-(5-fluoro-2-methylbenzoyl)piperidine-1-carboxylate (10.5 g, yield 88%), which was used in the next step without purification.

Step 2. (R)-tert-butyl 3-((R)-(5-fluoro-2-methylphenyl)(hydroxy)methyl)piperidine-1-carboxylate To a solution of (R)-tert-butyl 3-(5-fluoro-2-methylbenzoyl)piperidine-1-carboxylate (10.5 g, 0.0336 mol) in anhydrous THF (150 mL) at −15° C. under nitrogen was added dropwise a solution of 1 M R-CBS-oxazaborolidine in toluene (3 mL, 3 mmol, 0.09 eq). After stirring for 1 hr at −15° C., a solution of 10 M BH$_3$ in THF (17 mL, 0.0336 mol, 1 eq) was added dropwise. After addition, the reaction mixture was stirred for 2 hr at −15° C. Methanol (80 mL) was added dropwise carefully at −15° C. The solvent was removed under reduced pressure, the residue was purified by column chromatography on silica gel eluting with AcOEt/hexane (1:30→1:15) to provide the light yellow oil (95 g, HPLC≧70%, ratio≧3:1). The mixture was dissolved in a minimum volume of EtOAc, the solvent was removed on the rotary evaporator until crystals appeared. The solution was cooled to rt and stood for 1-2 h. To the solution was added hexane and then filtered, the crystals were washed with cool hexane and re-crystallized an additional two times to afford the pure isomer (R)-tert-butyl 3-((R)-(5-fluoro-2-methylphenyl)(hydroxy)methyl)piperidine-1-carboxylate (3.2 g, ee≧99%). $^1$H NMR (CDCl$_3$) δ 7.1 (m, 2H), 6.85 (m, 1H), 4.7 (m, 1H), 2.3 (s, 3H), 1.45 (s, 9H), 1.25 (m, 4H).

Step 3. (R)-tert-butyl 3-((R)-(cyanomethoxy)(5-fluoro-2-methylphenyl)methyl)piperidine-1-carboxylate To a solution of (R)-tert-butyl 3-((R)-(5-fluoro-2-methylphenyl)(hydroxy)methyl)piperidine-1-carboxylate (1.2 g, 0.0037 mol) in MeCN (20 mL), NaH (0.27 g, 0.011 mol) was added at 0° C. The mixture was stirred for 1 hr followed by cooling to −40° C. and adding bromoacetonitrile (1.3 g, 0.011 mol) in portions. The mixture was stirred for 0.5 hour at −20° C. The reaction was quenched with H$_2$O. The mixture was extracted with CH$_2$Cl$_2$. The organic layer was dried by Na$_2$SO$_4$, concentrate to get the target molecule (R)-tert-butyl 3-((R)-(cyanomethoxy)(5-fluoro-2-methylphenyl)methyl)piperidine-1-carboxylate (1.2 g, 90%).

Step 4. (R)-tert-butyl 3-((R)-(2-aminoethoxy)(5-fluoro-2-methylphenyl)methyl)piperidine-1-carboxylate A solution of (R)-tert-butyl 3-((R)-(cyanomethoxy)(5-fluoro-2-methylphenyl)methyl)piperidine-1-carboxylate (1.8 g, 0.005 mol) in anhydrous THF (20 ml) was heated to reflux under nitrogen. A solution of BH$_3$.Me$_2$S in THF was added dropwise and stirring was continued under reflux overnight. When the resulting solution was cooled to rt, MeOH was added dropwise to quench the reaction. After evaporation of the solution, the crude product was purified by column chromatography to afford (R)-tert-butyl 3-((R)-(2-aminoethoxy)(5-fluoro-2-methylphenyl)methyl)piperidine-1-carboxylate (1.2 g, yield 66%).

Step 5. (R)-tert-butyl 3-((R)-(5-fluoro-2-methylphenyl)(2-(methoxycarbonylamino)ethoxy)methyl)piperidine-1-carboxylate To a solution of (R)-tert-butyl 3-((R)-(2-aminoethoxy)(5-fluoro-2-methylphenyl)methyl)piperidine-1-carboxylate (3.1 g, 8.5 mmol) and DMAP (0.54 g) in dry CH$_2$Cl$_2$ (45 mL), Et$_3$N (2.58 g, 3.6 mL) was added. The resulting mixture was cooled to 0-5° C. under ice-water bath, a solution of methyl chloroformate (4.0 g, 43 mmol, 5 eq) in dry CH$_2$Cl$_2$ (50 mL) was added dropwise. After addition, the reaction mixture was stirred for 1-2 h at 0-5° C. The reaction was quenched with water (50 mL). The aqueous layer was extracted with CH$_2$Cl$_2$ (3×30 mL), the combined organic layers were washed with 10% citric acid (2×50 mL) and brine, then dried over Na$_2$SO$_4$, filtered and concentrated to the crude product, which was purified by preparative HPLC to afford (R)-tert-butyl 3-((R)-(5-fluoro-2-methylphenyl)(2-(methoxycarbonylamino)ethoxy)methyl)piperidine-1-carboxylate (400 mg, HPLC≧98%). $^1$H NMR (CDCl$_3$) δ 7.2 (m, 1H), 7.1 (m, 1H), 6.9 (m, 1H), 4.4 (m, 1H), 4.1 (m, 1H), 3.7 (m, 1H), 3.6 (s, 3H), 3.2 (m, 2H), 2.9 (m, 2H), 2.3 (s, 3H), 1.75 (m, 1H), 1.6 (m, 1H), 1.4 (s, 9H), 1.25 (m, 2H).

EXAMPLE 4

(R)-tert-butyl 3-((R)-(3-chloro-5-fluorophenyl)(2-(methoxycarbonylamino)ethoxy)methyl)piperidine-1-carboxylate

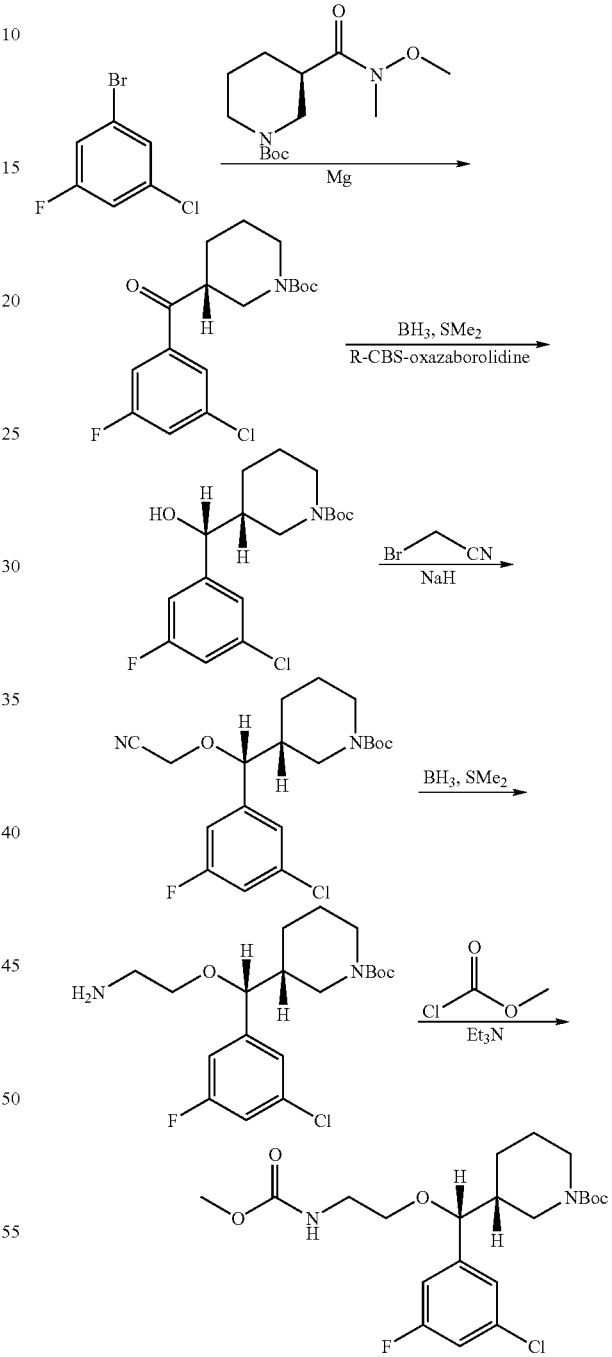

Step 1. (R)-tert-butyl 3-(3-chloro-5-fluorobenzoyl)piperidine-1-carboxylate

In a 2 L three-necked bottle flushed with N$_2$, Mg (26.5 g, 1.1 mol) was warmed to 50° C., 1-bromo-3-chloro-5-fluorobenzene (157 g, 0.75 mol) solution in anhydrous THF (1 L) was added dropwise, then the mixture was stirred at r.t. for 2 hr. To a solution of (R)-tert-butyl 3-(methoxy(methyl)carbamoyl)piperidine-1-carboxylate (120 g, 0.441 mol) in anhydrous THF (1.1 L) at −78° C. under nitrogen was added dropwise the above Grignard reagent. The reaction mixture was allowed to warm to rt and stirred for 2 h. The mixture was quenched with saturated NH$_4$Cl solution (500 mL) and extracted with EtOAc (3×400 mL). The combined organic layer was washed with brine, dried over Na$_2$SO$_4$ and concentrated in vacuo to give (R)-tert-butyl 3-(3-chloro-5-fluorobenzoyl)piperidine-1-carboxylate (163 g), which was used immediately without further purification.

Step 2. (R)-tert-butyl 3-((R)-(3-chloro-5-fluorophenyl)(hydroxy)methyl)piperidine-1-carboxylate A mixture of 10 M H$_3$B.S$_2$Me in THF (47.7 mL, 0.477 mol) and 1 M R-CBS-oxazaborolidine in toluene (72 mL, 0.072 mol) were dissolved in 100 mL anhydrous THF and cooled to −15° C. (R)-tert-butyl 3-(3-chloro-5-fluorobenzoyl)piperidine-1-carboxylate in 400 mL anhydrous THF was added dropwise to the above solution and stirred at −15° C. for 2 hr. The reaction was quenched with methanol (500 mL). The solvent was removed under reduced pressure and the residue was purified by column chromatography. The product was re-crystallized three times with EtOAc/Hexanes to give (R)-tert-butyl 3-((R)-(3-chloro-5-fluorophenyl)(hydroxy)methyl)piperidine-1-carboxylate (55 g, 0.156 mol). $^1$H NMR (CDCl$_3$, 400 MHz) δ 7.10 (s, 1H), 7.04-6.90 (dd, 2H), 4.46-4.30 (d, 1H), 4.05-2.40 (m, 5H), 1.74 (s, 1H), 1.60 (s, 1H), 1.53-1.31 (m, 1H), 1.30-1.14 (m, 1H).

Step 3. (R)-tert-butyl 3-((R)-(3-chloro-5-fluorophenyl)(cyanomethoxy)methyl)piperidine-1-carboxylate A solution of (R)-tert-butyl 3-((R)-(3-chloro-5-fluorophenyl)(hydroxy)methyl)piperidine-1-carboxylate (55 g, 0.156 mol) in acetonitrile (1.2 L) was cooled to 0° C., NaH (19.2 g, 0.48 mol, 60% in oil) was added in portions, then the mixture was stirred at rt for 1 hr. The mixture was cooled to −20° C. and bromoacetonitrile (57.7 g, 0.48 mol) was added dropwise. After 0.5 hr, additional NaH (19.2 g, 0.48 mol, 60% in oil) and bromoacetonitrile (57.7 g, 0.48 mol) was added. TLC showed 80% of the starting material was reacted. The reaction was quenched with saturated NH$_4$Cl solution (200 mL), water (1 L) was added. Acetonitrile was removed by reduced pressure, CH$_2$Cl$_2$ (1 L) was added, the aqueous layer was back extracted with CH$_2$Cl$_2$ (3×500 mL), dried over Na$_2$SO$_4$ and concentrated in vacuo to give the crude (R)-tert-butyl 3-((R)-(3-chloro-5-fluorophenyl)(cyanomethoxy)methyl)piperidine-1-carboxylate (90 g), which was used for the next step without further purification.

Step 4. (R)-tert-butyl 3-((R)-(2-aminoethoxy)(3-chloro-5-fluorophenyl)methyl)piperidine-1-carboxylate A solution of (R)-tert-butyl 3-((R)-(3-chloro-5-fluorophenyl)(cyanomethoxy)methyl)piperidine-1-carboxylate (90 g) in anhydrous THF (1.3 L), under protection of N$_2$, was heated to reflux followed by the dropwise addition of 10 M H$_3$B.SMe$_2$ in THF (70 mL, 0.7 mol). The mixture was stirred at reflux overnight. The reaction was quenched with MeOH (500 mL) and the solvent removed in vacuo, the residue was purified by column chromatography to give (R)-tert-butyl 3-((R)-(2-aminoethoxy)(3-chloro-5-fluorophenyl)methyl)piperidine-1-carboxylate (24 g, 0.062 mol).

Step 5. (R)-tert-butyl 3-((R)-(3-chloro-5-fluorophenyl)(2-(methoxycarbonylamino)ethoxy)methyl)piperidine-1-carboxylate A solution of (R)-tert-butyl 3-((R)-(2-aminoethoxy)(3-chloro-5-fluorophenyl)methyl)piperidine-1-carboxylate (24 g, 0.062 mol) in dry CH$_2$Cl$_2$ (300 mL) and Et$_3$N (31.4 g, 43 mL) was cooled to 0° C. in ice-water bath, a solution of methyl chloroformate (11.8 g, 0.124 mol) in dry CH$_2$Cl$_2$ (100 mL) was added dropwise. After addition, the reaction mixture was stirred for 1-2 h at 0-5° C. Water (200 mL) was added to quench the reaction. The aqueous layer was extracted with CH$_2$Cl$_2$ (3×100 mL), the combined organic layers were washed with 10% citric acid (2×80 mL) and brine, then dried over Na$_2$SO$_4$, filtered and concentrated to give the crude product, which was purified by column chromatography to give (R)-tert-butyl 3-((R)-(3-chloro-5-fluorophenyl)(2-(methoxycarbonylamino)ethoxy)methyl)piperidine-1-carboxylate (19 g, 0.043 mol). $^1$H NMR (CD$_3$OD) δ 7.17 (s, 1H), 7.16-7.08 (m, 1H), 7.07-7.00 (m, 1H), 4.20-4.00 (m, 2H), 3.90-3.78 (d, 1H), 3.61 (s, 3H), 3.28-3.20 (m, 2H), 2.92-2.68 (dd, 2H), 1.52-1.74 (m, 2H), 1.42 (s, 9H), 1.35-1.10 (m, 3H),

EXAMPLE 5

(R)-tert-butyl 3-((R)-(3-fluorophenyl)(2-(methoxycarbonylamino)ethoxy)methyl)piperidine-1-carboxylate

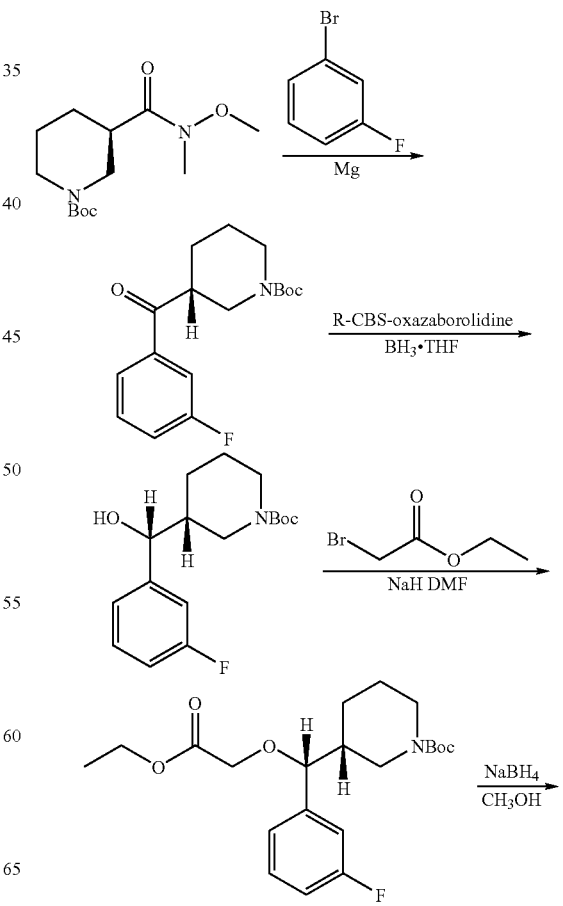

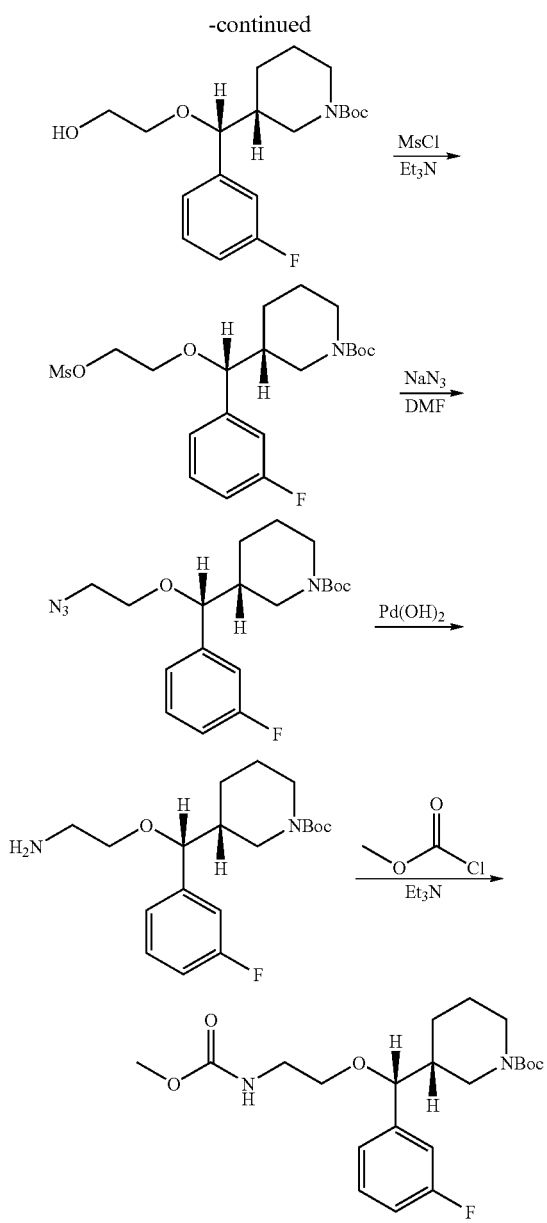

Step 1. (R)-tert-butyl 3-(3-fluorobenzoyl)piperidine-1-carboxylate

A solution of 1-bromo-3-fluoro-benzene (57.7 g, 0.33 mol) in anhydrous THF (480 mL) was added dropwise to Mg (10.6 g, 0.44 mol) at rt under nitrogen. The mixture was stirred at 50-60° C. for 1 hr. The resulting Grignard reagent was used for the next step. The Grignard reagent was added dropwise to a solution of (R)-tert-butyl 3-(methoxy(methyl)carbamoyl)piperidine-1-carboxylate (60 g, 0.22 mol) in anhydrous THF (600 mL) at −78° C. under nitrogen. After addition, the mixture was allowed to stir at rt for 1.5 hr. The mixture was quenched with saturated NH$_4$Cl solution (300 mL) and extracted with EtOAc (3×200 mL). The combined organic layers were washed with brine, dried over Na$_2$SO$_4$ and concentrated in vacuo to give crude (R)-tert-butyl 3-(3-fluorobenzoyl)piperidine-1-carboxylate (67.5 g, 100%), which was used immediately in the next step without purification.

Step 2. (R)-tert-butyl 3-((R)-(3-fluorophenyl)(hydroxy)methyl)piperidine-1-carboxylate To a solution of 1 M R-CBS-oxazaborolidine in toluene (33 mL, 33 mmol, 0.15 eq) and 10 M BH$_3$ in THF (22 mL, 0.22 mol, 1.0 eq) at −15° C. under nitrogen was added dropwise a solution of (R)-tert-butyl 3-(3-fluorobenzoyl)piperidine-1-carboxylate (67.5 g, 0.22 mol) in anhydrous THF (300 mL). After addition, the reaction mixture was stirred for 1 hr at rt. Methanol (200 mL) was added dropwise carefully at 0° C. The solvent was removed under reduced pressure to provide the crude product. The crude product was dissolved in EtOAc until the alcohol was just dissolved (about 5 mL/1 g), the solvent was removed on the rotary evaporator until a few crystals appeared. To the above solution was added petroleum ether (about 300 mL) under stirring, which was allowed to stir at rt for 2 hr and then filtered, the crystals were washed with petroleum ether and re-crystallized to afford the pure R)-tert-butyl 3-((R)-(3-fluorophenyl)(hydroxy)methyl)piperidine-1-carboxylate (26 g, 39%).

Step 3. (R)-tert-butyl 3-((R)-(2-ethoxy-2-oxoethoxy)(3-fluorophenyl)methyl)piperidine-1-carboxylate To a suspension of NaH (4.8 g, 120 mmol) in THF (400 mL) at 0-5° C. was added dropwise a solution of (R)-tert-butyl 3-((R)-(2-ethoxy-2-oxoethoxy)(3-fluorophenyl)methyl)piperidine-1-carboxylate (30.9 g, 100 mmol) in anhydrous THF (100 mL), the reaction mixture was stirred for 1 hr at rt. A solution of ethyl bromoacetate (20.04 g, 13.40 mL, 120 mmol) in anhydrous THF (100 mL) was added dropwise to the above mixture, and the reaction was heated to reflux for 3-5 hr. The reaction mixture was poured into saturated aqueous NH$_4$Cl, then extracted with EtOAc (3×100 mL). The organic layer was washed with water (3×100 mL) and brine, dried over Na$_2$SO$_4$, filtered and concentrated in vacuo to afford crude (R)-tert-butyl 3-((R)-(2-ethoxy-2-oxoethoxy)(3-fluorophenyl)methyl)piperidine-1-carboxylate (29.88 g 76%), which was used for next step without purification.

Step 4. (R)-tert-butyl 3-((R)-(3-fluorophenyl)(2-hydroxyethoxy)methyl)piperidine-1-carboxylate To a solution of (R)-tert-butyl 3-((R)-(2-ethoxy-2-oxoethoxy)(3-fluorophenyl)methyl)piperidine-1-carboxylate (29.88 g, 75.9 mmol) in MeOH (300 mL) was added NaBH$_4$ (23 g, 605.2 mmol) in portions while the temperature was lower than 40° C. After addition, the mixture was stirred at rt for 2-3 hr. The solvent was removed in vacuo to give a residue which was partitioned between water and EtOAc. The organic layer was washed with H$_2$O and brine, dried over Na$_2$SO$_4$, filtered and concentrated in vacuo. The residue was purified on silica gel chromatography to afford (R)-tert-butyl 3-((R)-(3-fluorophenyl)(2-hydroxyethoxy)methyl)piperidine-1-carboxylate (11 g, 41%).

Step 5. (R)-tert-butyl 3-((R)-(3-fluorophenyl)(2-(methylsulfonyloxy)ethoxy)methyl)piperidine-1-carboxylate To a solution of (R)-tert-butyl 3-((R)-(3-fluorophenyl)(2-hydroxyethoxy)methyl)piperidine-1-carboxylate (11 g, 31.16 mmol) in dry CH$_2$Cl$_2$ (140 mL) was added Et$_3$N (12.60 g, 16.68 mL, 124.65 mmol, 4 eq) at −5-0° C. Then a solution of MsCl (7.1 g, 4.72 mL, 62.32 mmol, 2 eq) in dry CH$_2$Cl$_2$ (40 mL) was added dropwise at the same temperature. After addition, it was allowed to warm to rt gradually. Water (100 mL) was added. The aqueous layer was extracted with CH$_2$Cl$_2$ (3×80 mL), the combined organic layers was washed with 10% citric acid, sat. NaHCO$_3$ and brine, then dried over Na$_2$SO$_4$, filtered and concentrated to give (R)-tert-butyl 3-((R)-(3-fluorophenyl)(2-(methylsulfonyloxy)ethoxy)methyl)piperidine-1-carboxylate (13.8 g), which was used in the next step without purification.

Step 6. (R)-tert-butyl 3-((R)-(2-azidoethoxy)(3-fluorophenyl)methyl)piperidine-1-carboxylate (R)-tert-Butyl 3-((R)-(3-fluorophenyl)(2-(methylsulfonyloxy)ethoxy)methyl)piperidine-1-carboxylate (13.8 g, 32 mmol) was dissolved into anhydrous DMF (150 mL), solid NaN$_3$ (6.1 g, 96 mmol, 3 eq) was added and the reaction mixture was heated to 80° for overnight. The reaction mixture was cooled to rt and then was added with EtOAc (500 mL), the organic phase was washed with water (3×100 mL) and brine (2×80 mL), dried over Na$_2$SO$_4$ and concentrated in vacuo to give crude (R)-tert-butyl 3-((R)-(2-azidoethoxy)(3-fluorophenyl)methyl)piperidine-1-carboxylate (12 g), which was used in the next step without further purification.

Step 7. (R)-tert-butyl 3-((R)-(2-aminoethoxy)(3-fluorophenyl)methyl)piperidine-1-carboxylate A suspension of (R)-tert-butyl 3-((R)-(2-azidoethoxy)(3-fluorophenyl)methyl)piperidine-1-carboxylate (12 g, 31.75 mmol) and Pd(OH)$_2$/C (1.2 g) in MeOH (240 ml) was stirred under H$_2$ for 1 hr. The mixture was filtered and evaporated under reduced pressure to give desired (R)-tert-butyl 3-((R)-(2-aminoethoxy)(3-fluorophenyl)methyl)piperidine-1-carboxylate (10 g).

Step 8. (R)-tert-butyl 3-((R)-(3-fluorophenyl)(2-(methoxycarbonylamino)ethoxy)methyl)piperidine-1-carboxylate To a solution of (R)-tert-butyl 3-((R)-(2-aminoethoxy)(3-fluorophenyl)methyl)piperidine-1-carboxylate (10 g, 28.41 mmol) and DMAP (1.8 g, 14.21 mmol, 0.5 eq) in dry CH$_2$Cl$_2$ (150 mL), Et$_3$N (8.62 g, 11.42 mL, 85.23 mmol) was added. The resulting mixture was cooled to 0-5° C. under ice-water bath, a solution of methyl chloroformate (10.95 mL, 142.05 mmol, 5 eq) in dry CH$_2$Cl$_2$ (60 mL) was added dropwise. After addition, the reaction mixture was stirred for 1-2 hr at 0-5° C. Water (80 mL) was added to quench the reaction. The aqueous layer was extracted with CH$_2$Cl$_2$ (3×50 mL), the combined organic layers were washed with 10% citric acid (2×80 mL) and brine, then dried over Na$_2$SO$_4$, filtered and concentrated to the crude product, which was purified by silica gel to afford (R)-tert-butyl 3-((R)-(3-fluorophenyl)(2-(methoxycarbonylamino)ethoxy)methyl)piperidine-1-carboxylate (11.3 g, 97%).

EXAMPLE 6

(R)-tert-butyl 3-((R)-(5-chloro-2-methylphenyl)(2-(methoxycarbonylamino)ethoxy)methyl)piperidine-1-carboxylate

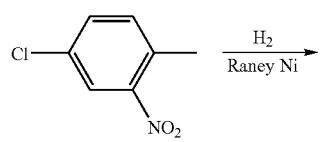

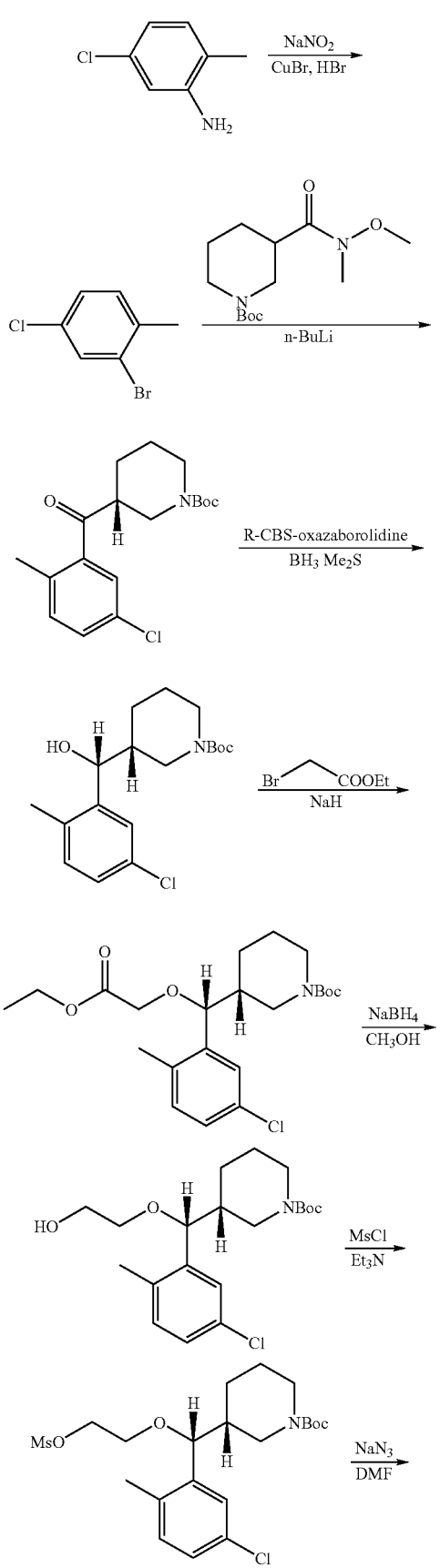

49

-continued

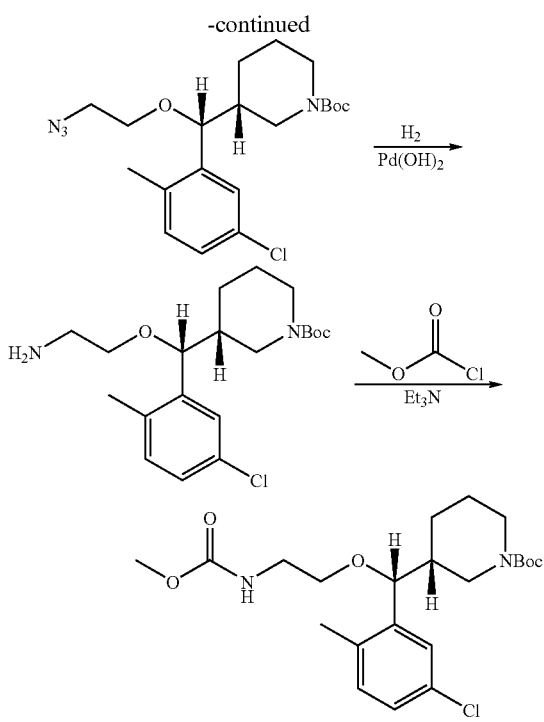

Step 1. 5-chloro-2-methylbenzenamine

A 2 L flask was charged the solution of 4-chloro-1-methyl-2-nitrobenzene (60 g, 0.35 mol) in MeOH (1 L), Raney Ni was added, the air in flask was replaced three times with $H_2$, the mixture was stirred for 3 hr at rt. The solution was filtered and concentrated. The residue was dissolved in $CH_2Cl_2$ (500 mL), and the solution was washed with brine, dried over $Na_2SO_4$. Solvent removal gave 5-chloro-2-methylbenzenamine (50 g, 0.35 mol). $^1$H NMR (CDCl$_3$, 400 MHz) δ 7.02-6.93 (d, 2H), 6.70-6.60 (d, 2H), 3.67 (s, 2H), 2.14 (s, 3H).

Step 2. 2-bromo-4-chloro-1-methylbenzene 5-chloro-2-methylbenzenamine (50 g, 0.355 mol) was dissolved in HBr solution (1.5 M, 100 mL) and cooled to 0° C., a solution of NaNO$_2$ (27.6 g, 0.4 mol) in water (200 mL) was added dropwise. After addition, the mixture was stirred for 1 hr. In another flask CuBr (30 g, 0.21 mol) was added to HBr solution (1.5 M, 30 mL) and heated to 60° C., then the mixture was added to the above solution. The mixture was heated to reflux for 1 hr then cooled to rt. The reaction was quenched with water (500 mL), the aqueous layer was extracted 3 times with $CH_2Cl_2$, dried over $Na_2SO_4$, solvent removal and purification by column chromatography afforded 2-bromo-4-chloro-1-methylbenzene (53 g, 0.26 mol). $^1$H NMR (CDCl$_3$, 400 MHz) δ 7.53 (s, 1H), 7.20-7.10 (m, 2H), 2.36 (s, 3H).

Step 3. (R)-tert-butyl 3-(5-chloro-2-methylbenzoyl)piperidine-1-carboxylate

To a solution of 2-bromo-4-chloro-1-methylbenzene (53 g, 0.26 mol) in anhydrous THF (600 mL) at −78° C. under nitrogen was added dropwise a solution of 2.5 M n-BuLi in hexane (103 mL, 0.26 mol). After stirring for 1 hr at −78° C., a solution of the (R)-tert-butyl 3-(methoxy(methyl)carbamoyl)piperidine-1-carboxylate (67 g, 0.246 mol) in anhydrous

50

THF (300 mL) was added dropwise. After addition, the reaction mixture was allowed to warm to rt and stirred for 2 hr. The mixture was quenched with saturated NH$_4$Cl solution (500 mL) and extracted with EtOAc (3×400 mL). The combined organic layers were washed with brine, dried over $Na_2SO_4$ and concentrated in vacuo to give crude (R)-tert-butyl 3-(5-chloro-2-methylbenzoyl)piperidine-1-carboxylate (86 g), which was used immediately in the next step without purification.

Step 4. (R)-tert-butyl 3-((R)-(5-chloro-2-methylphenyl)(hydroxy)methyl)piperidine-1-carboxylate A mixture of 10 M $BH_3 \cdot Me_2S$ in THF (25.4 mL, 0.254 mol) and 1 M R-CBS-oxazaborolidine in toluene (38 mL, 0.038 mol) were dissolved in 100 mL anhydrous THF and cooled to −15° C. (R)-tert-butyl 3-(5-chloro-2-methylbenzoyl)piperidine-1-carboxylate in 200 mL anhydrous THF was added dropwise to the above solution and stirred at −15° C. for 2 hr. The reaction was quenched with methanol (300 mL). The solvent was removed under reduced pressure, and the residue was purified by column chromatography to give (R)-tert-butyl 3-((R)-(5-chloro-2-methylphenyl)(hydroxy)methyl)piperidine-1-carboxylate (32 g), which contained 30% isomer.

Step 5. (R)-tert-butyl 3-((R)-(5-chloro-2-methylphenyl)(2-ethoxy-2-oxoethoxy)methyl)piperidine-1-carboxylate To a suspension of NaH (5.64 g, 0.141 mol) in the mixed solvent of DMF (70 mL) and THF (70 mL) at −25° C. was added dropwise a solution of (R)-tert-butyl 3-((R)-(5-chloro-2-methylphenyl)(hydroxy)methyl)piperidine-1-carboxylate (16 g, 47 mmol) in anhydrous THF (100 mL), the reaction mixture was stirred for 1 hr at rt. A solution of ethyl bromoacetate (15.6 g, 94 mmol) in anhydrous THF (70 mL) was added dropwise to the above mixture at −10–−5° C. After addition, the reaction mixture was stirred for 2-3 hr at rt. The reaction was quenched with saturated NH$_4$Cl solution (100 mL) and EtOAc (500 mL) was added. The organic layer was washed with water (5×50 mL) and brine, dried over $Na_2SO_4$, filtered and concentrated in vacuo. The residue was purified by column chromatography to afford (R)-tert-butyl 3-((R)-(5-chloro-2-methylphenyl)(2-ethoxy-2-oxoethoxy)methyl)piperidine-1-carboxylate (8 g, 18.8 mmol).

Step 6. (R)-tert-butyl 3-((R)-(5-chloro-2-methylphenyl)(2-hydroxyethoxy)methyl)piperidine-1-carboxylate To a solution of (R)-tert-butyl 3-((R)-(5-chloro-2-methylphenyl)(2-ethoxy-2-oxoethoxy)methyl)piperidine-1-carboxylate (8 g, 18.8 mmol) in MeOH (300 mL) was added NaBH$_4$ (5.6 g, 0.15 mol) in portions while the temperature was lower than 40° C. After addition, the mixture was stirred overnight. The solvent was removed in vacuo to the residue, which was partitioned between water and EtOAc. The organic layer was washed with H$_2$O and brine, dried over $Na_2SO_4$ and evaporated to give crude (R)-tert-butyl 3-((R)-(5-chloro-2-methylphenyl)(2-hydroxyethoxy)methyl)piperidine-1-carboxylate (7 g), which was used in the next step without purification.

Step 7. (R)-tert-butyl 3-((R)-(5-chloro-2-methylphenyl)(2-(methylsulfonyloxy)ethoxy)methyl)piperidine-1-carboxylate To a solution of (R)-tert-butyl 3-((R)-(5-chloro-2-methylphenyl)(2-hydroxyethoxy)methyl)piperidine-1-carboxylate (7 g, 18.3 mmol) in dry CH₂Cl₂ (100 mL) was added Et₃N (54 g, 10 mL, 0.73 mmol) at −5-0° C. Then a solution of MsCl (4.2 g, 36.5 mmol) in dry CH₂Cl₂ (50 mL) was added dropwise at the same temperature. After addition, it was allowed to warm to rt gradually. The reaction mixture was washed with 10% citric acid solution (30 mL), NaHCO₃ and brine, then dried over Na₂SO₄, filtered and concentrated to give (R)-tert-butyl 3-((R)-(5-chloro-2-methylphenyl)(2-(methyl sulfonyloxy)ethoxy)methyl)piperidine-1-carboxylate (8.4 g), which was used in the next step without purification.

Step 8. (R)-tert-butyl 3-((R)-(2-azidoethoxy)(5-chloro-2-methylphenyl)methyl)piperidine-1-carboxylate (R)-tert-butyl 3-((R)-(5-chloro-2-methylphenyl)(2-(methylsulfonyloxy)ethoxy)methyl)piperidine-1-carboxylate (8.4 g, 18.3 mmol) was dissolved in anhydrous DMF (150 mL), solid NaN₃ (3.56 g, 54.8 mmol.) was added and the reaction mixture was heated to 60° C. for overnight. The reaction mixture was cooled to rt and diluted with EtOAc (500 mL), the organic phase was washed with water (5×50 mL) and brine (100 mL), dried over Na₂SO₄ and concentrated in vacuo to give (R)-tert-butyl 3-((R)-(2-azidoethoxy)(5-chloro-2-methylphenyl)methyl)piperidine-1-carboxylate (7 g).

Step 9. (R)-tert-butyl 3-((R)-(2-aminoethoxy)(5-chloro-2-methylphenyl)methyl)piperidine-1-carboxylate (R)-tert-butyl 3-((R)-(2-azidoethoxy)(5-chloro-2-methylphenyl)methyl)piperidine-1-carboxylate (7 g, 17.1 mmol.) was dissolved in EtOAc (300 mL), 0.8 g of Pd(OH)₂ was added and the air in bottle was replaced 3 times with H₂, the reaction was stirred at rt for 3 hr. The solution was filtered and concentrated to give (R)-tert-butyl 3-((R)-(2-aminoethoxy)(5-chloro-2-methylphenyl)methyl)piperidine-1-carboxylate (6.2 g), which was used in the next step without further purification.

Step 10. (R)-tert-butyl 3-((R)-(5-chloro-2-methylphenyl)(2-(methoxycarbonylamino)ethoxy)methyl)piperidine-1-carboxylate To a solution of (R)-tert-butyl 3-((R)-(2-aminoethoxy)(5-chloro-2-methylphenyl)methyl)piperidine-1-carboxylate (6.2 g, 16.2 mmol) and DMAP (0.2 g, 1.62 mmol) in dry CH₂Cl₂ (70 mL), Et₃N (8 g, 81 mmol) was added. The resulting mixture was cooled to 0-5° C. in ice-water bath, a solution of methyl chloroformate (3.1 g, 32.4 mmol) in dry CH₂Cl₂ (30 mL) was added dropwise. After addition, the reaction mixture was stirred for 1-2 hr at 0-5° C. The reaction was quenched with water. The aqueous layer was extracted with CH₂Cl₂ (3×30 mL), the combined organic layers were washed with brine, then dried over Na₂SO₄, filtered and concentrated to give the crude product, which was firstly purified by column chromatography and then by preparative HPLC to give (R)-tert-butyl 3-((R)-(5-chloro-2-methylphenyl)(2-(methoxycarbonylamino)ethoxy)methyl)piperidine-1-carboxylate (1.5 g). ¹H NMR (CD₃OD, 400 MHz) δ 7.30 (s, 1H), 7.20-7.10 (d, 2H), 4.81 (s, 1H), 4.46-4.30 (d, 1H), 4.29-4.15 (d, 1H), 3.95-3.83 (d, 1H), 3.62 (s, 3H), 3.30 (s, 4H), 2.90-2.65 (dd, 2H), 2.30 (s, 3H), 1.70 (s, 1H), 1.59 (s, 1H), 1.41 (s, 9H), 1.35-1.20 (m, 3H).

EXAMPLE 7

2,2-dimethyl-4-(((R)-tetrahydro-2H-pyran-3-yl)methyl)oxazolidine

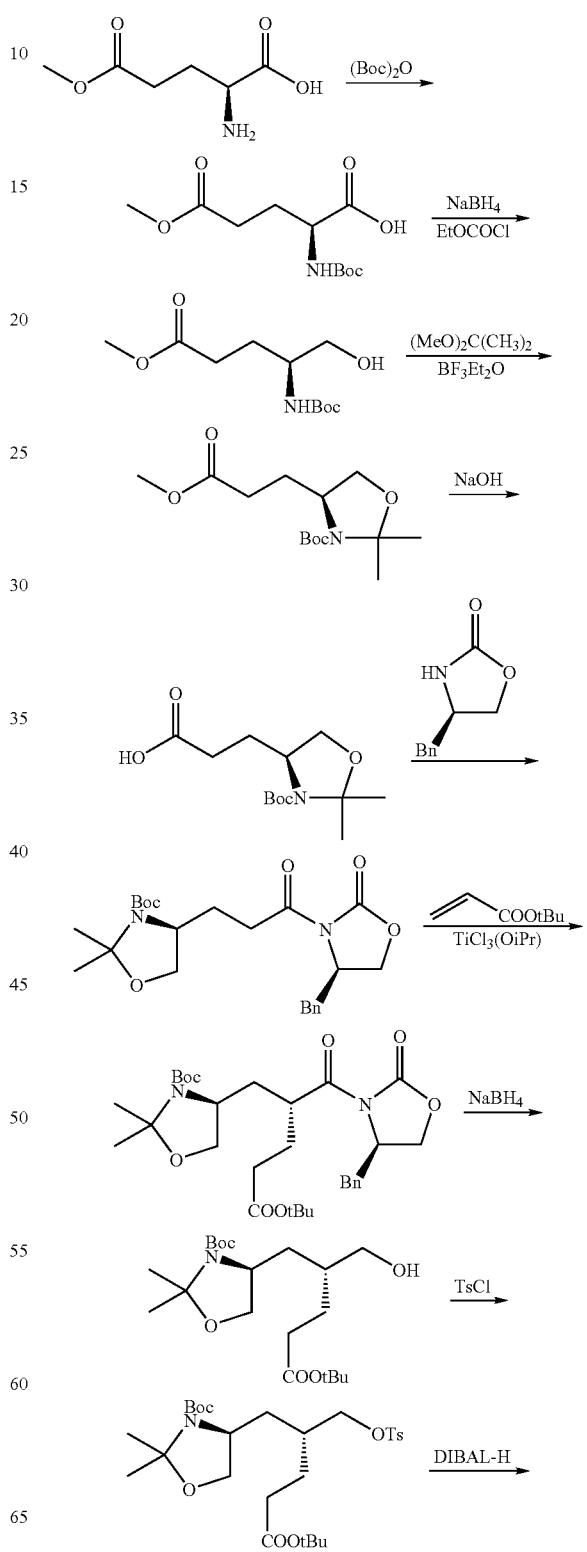

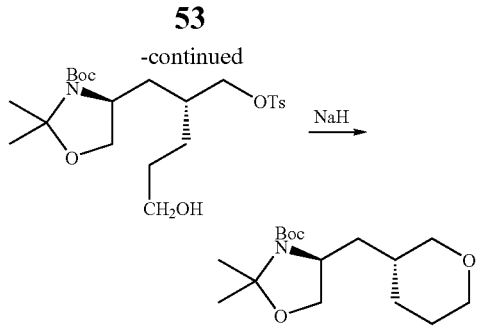

Step 1. (S)-2-(tert-butoxycarbonylamino)-5-methoxy-5-oxopentanoic acid

To a round bottom flask, Et$_3$N (303 g, 3 mol) was added dropwise to a stirred solution of Boc$_2$O (261.6 g, 1.2 mol) and 2-amino-pentanedioic acid 5-methyl ester (161 g, 1 mol) in water (800 ml) and dioxane (800 ml). After 18 hr the solution was extracted with petroleum ether (2×1000 ml) and the aqueous phase was cooled on ice and carefully acidified to pH 3 by slow addition of 10% citric acid solution. The urethane was then extracted into EtOAc (3×1000 ml) and the combined extracts were washed with brine, then dried (Na$_2$SO$_4$), filtered and concentrated under reduced pressure to give (S)-2-(tert-butoxycarbonylamino)-5-methoxy-5-oxopentanoic acid (238 g, 91.2%), which was used without further purification.

Step 2. (S)-methyl 4-(tert-butoxycarbonylamino)-5-hydroxypentanoate

To a stirred solution of (S)-2-(tert-butoxycarbonylamino)-5-methoxy-5-oxopentanoic acid (35.2 g, 0.135 mol) in THF (500 mL) at −10° C. was added N-methylmorpholine (15 mL, 0.135 mol) followed by ethyl chloroformate (14.72 g, 0.135 mol). After 10 min, NaBH$_4$ (15.37 g, 0.405 mol) was added in one portion. MeOH (1200 mL) was then added dropwise to the mixture over a period of 20 min at 0° C. The solution was stirred for an additional 20 min and then neutralized with 1M KHSO$_4$. The organic solvent was removed and the aqueous layer was extracted with EtOAc (3×500 ml). The combined organic phases were washed consecutively with 1M KHSO$_4$ (300 mL), H$_2$O (300 mL), 5% aqueous NaHCO$_3$ (300 mL), and dried (Na$_2$SO$_4$). The solvent was evaporated to give a residue, which was purified by column chromatography to give the desired (S)-methyl 4-(tert-butoxycarbonylamino)-5-hydroxypentanoate (24 g, 72%)

Step 3. (S)-tert-butyl 4-(3-methoxy-3-oxopropyl)-2,2-dimethyloxazolidine-3-carboxylate (S)-methyl 4-(tert-butoxycarbonylamino)-5-hydroxypentanoate (24 g, 97.2 mmol) and isopropenyl methyl ether (88.8 g, 854.6 mmol) was dissolved in acetone (2000 mL) and BF$_3$-Et$_2$O (0.82 mL, 5.84 mmol) was added at rt. The mixture was stirred for 1 hr at rt. The reaction was quenched by addition of Et$_3$N (11.6 mL). The reaction solution was washed with aqueous saturated NaHCO$_3$ (200 mL) and evaporated, and (S)-tert-butyl 4-(3-methoxy-3-oxopropyl)-2,2-dimethyloxazolidine-3-carboxylate (25.1 g, 90%) was obtained as an oil, which was used in the next step without further purification.

Step 4. (S)-3-(3-(tert-butoxycarbonyl)-2,2-dimethyloxazolidin-4-yl)propanoic acid An aqueous solution of sodium hydroxide (195 mL, 4.0 M in H$_2$O, 0.261 mol, 3.0 eq) was added to a solution of (S)-tert-butyl 4-(3-methoxy-3-oxopropyl)-2,2-dimethyloxazolidine-3-carboxylate (25.1 g, 0.087 mol), and the resulting cloudy reaction mixture was stirred at 23° C. for 3.5 hr. The mixture was concentrated under reduced pressure to ~50 mL volume and then was partitioned between 0.5 M HCl (360 ml) and EtOAc (2×360 ml). The combined organic layers were dried over Na$_2$SO$_4$ and were filtered. The filtrate was concentrated under reduced pressure to give (S)-3-(3-(tert-butoxycarbonyl)-2,2-dimethyloxazolidin-4-yl)propanoic acid (21.6 g, 91%), which was used without further purification.

Step 5. (S)-tert-butyl 2,2-dimethyl-4-(3-((R)-4-methyl-2-oxooxazolidin-3-yl)-3-oxopropyl)oxazolidine-3-carboxylate A 2000 mL flask was charged with (S)-3-(3-(tert-butoxycarbonyl)-2,2-dimethyloxazolidin-4-yl)propanoic acid (21.6 g, 79 mmol) and 750 mL of dry THF. The solution was cooled to 0° C., then triethylamine (23.94 g, 237 mmol, 3.0 equiv) and pivaloyl chloride (9.76 mL, 79 mmol, 1.0 equiv) were sequentially added. The solution was stirred for 4 hr at 0° C. After this time (R)-4-benzyl-2-oxalozolidinone (13.26 g, 75.2 mmol, 0.95 equiv) and dried LiCl (3.68 g, 86.4 mmol, 1.1 equiv) were added and the reaction was allowed to stir for 13 hr with concomitant warming to ambient temperature. After this time 560 mL of 0.5 M HCl was added, the mixture was transferred to a separatory funnel and the layers were separated. The aqueous layer was extracted with EtOAc (3×370 mL), and the combined organic layers washed with 10% K$_2$CO$_3$ (2×370 mL), and brine (2×370 mL), then dried over Na$_2$SO$_4$, and evaporated. The crude material was purified by flash chromatography, eluting with 0-29% EtOAc in hexanes. This afforded 26.3 g (81%) of (S)-tert-butyl 2,2-dimethyl-4-(3-((R)-4-methyl-2-oxooxazolidin-3-yl)-3-oxopropyl)oxazolidine-3-carboxylate as a clear syrup.

Step 6. (S)-tert-butyl 4-((R)-5-tert-butoxy-2-((R)-4-methyl-2-oxooxazolidine-3-carbonyl)-5-oxopentyl)-2,2-dimethyloxazolidine-3-carboxylate At 0° C., 1.0M TiCl$_4$ in CH$_2$Cl$_2$ solution (8.55 mL, 0.7 eq) was added to CH$_2$Cl$_2$ (100 mL) followed by the addition of 1.0M TiCl(Oi—Pr)$_3$ in hexanes solution (4.28 mL, 0.35 eq) and stirred 5 min DIPEA (2.87 mL, 1.35 eq) was added and stirred 15 min. A solution of (S)-tert-butyl 2,2-dimethyl-4-(3-((R)-4-methyl-2-oxooxazolidin-3-yl)-3-oxopropyl)oxazolidine-3-carboxylate (5.28 g, 12.22 mmol) in CH$_2$Cl$_2$ (50 mL) was added. The reaction mixture was stirred 1 hr at 0° C. To the solution, t-butylacrylate (2.22 mL, 1.25 eq) was added and the mixture was left stirred over 48 hr with concomitant warming to rt. The mixture was concentrated, partitioned between EtOAc (300 mL) and 1% HCl solution (100 mL). The organic layer was washed with sat. NaHCO$_3$ solution (60 mL), brine (60 mL), dried over Na$_2$SO$_4$. After filtration and concentration, the residue was purified by ISCO (120 g column, 0~35% EtOAc in Hexanes gradient) to afford 4.12 g (60%) (S)-tert-butyl 4-((R)-5-tert-butoxy-2-((R)-4-methyl-2-oxooxazolidine-3-carbonyl)-5-oxopentyl)-2,2-dimethyloxazolidine-3-carboxylate as a yellowish solid. MS ESI+ve m/z 583 (M+Na).

Step 7. (S)-tert-butyl 4-((R)-5-tert-butoxy-2-(hydroxymethyl)-5-oxopentyl)-2,2-dimethyloxazolidine-3-carboxylate (S)-tert-butyl 4-((R)-5-tert-butoxy-2-((R)-4-methyl-2-oxooxazolidine-3-carbonyl)-5-oxopentyl)-2,2-dimethyloxazolidine-3-carboxylate (4.12 g, 7.36 mmol) was dissolved in 4:1 THF and methanol (200 mL) and cooled to 0° C. Sodium borohydride (557 mg, 2 eq) was added slowly. After 10 min., the mixture was warmed up to rt slowly. The mixture was stirred 2 hr at rt. The mixture was concentrated, redissolved in EtOAc (300 mL), washed with 1% HCl solution (100 mL), brine (60 mL), and dried over Na₂SO₄. After filtration and concentration, the residue was purified by ISCO (40 g column, 10-65% EtOAc in Hexanes gradient, check TLC with Ninhydrin stain) to afford 2.86 g of (S)-tert-butyl 4-((R)-5-tert-butoxy-2-(hydroxymethyl)-5-oxopentyl)-2,2-dimethyloxazolidine-3-carboxylate as a white solid. MS ESI+m/v 410 (M+Na).

Step 8. (S)-tert-butyl 4-((R)-5-tert-butoxy-5-oxo-2-(tosyloxymethyl)pentyl)-2,2-dimethyloxazolidine-3-carboxylate To a solution of (S)-tert-butyl 4-((R)-5-tert-butoxy-2-(hydroxymethyl)-5-oxopentyl)-2,2-dimethyloxazolidine-3-carboxylate (244 mg, 0.63 mmol) in anhydrous DCM (6 mL) was added pyridine (2 mL) and catalytic amount of DMAP, the solution was chilled to 0° C. Tosic chloride (360 mg, 1.88 mmol) was added and stirred at rt overnight. The reaction mixture was diluted with EtOAc (40 mL) and washed with 1 N HCl (2×, 50 ml+20 ml), followed by H₂O, aq. NaHCO₃, brine, dried over Na₂SO₄, and filtered. After evaporation of solvent, the residue was purified on silica gel column, eluted with 0-20% EtOAc in hexane to afford (S)-tert-butyl 4-((R)-5-tert-butoxy-5-oxo-2-(tosyloxymethyl)pentyl)-2,2-dimethyloxazolidine-3-carboxylate (317 mg, yield 93%).

Step 9. (S)-tert-butyl 4-((R)-5-hydroxy-2-(tosyloxymethyl)pentyl)-2,2-dimethyloxazolidine-3-carboxylate To a solution of (S)-tert-butyl 4-((R)-5-tert-butoxy-5-oxo-2-(tosyloxymethyl)pentyl)-2,2-dimethyloxazolidine-3-carboxylate (317 mg, 0.58 mmol) in anhydrous DCM (8 mL) at −78° C. under N₂ was added DiBAlH (1 M in hexane, 1.75 mL, 1.75 mmol) dropwise. After the addition, the reaction mixture was stirred for another 30 min. The reaction was quenched with MeOH (2 mL), followed by 50% Rochelle's salt aq solution and stirred 2 hr. The resulting solution was extracted with DCM (3×20 mL), the combined organic phases were concentrated and dissolved in THF/MeOH (10 mL, 4/1, v/v), and chilled to 0° C., NaBH₄ (11 mg, 0.29 mmol) was added and stirred at this temperature for 30 min. The reaction was quenched by aqueous NH₄Cl, then extracted with EtOAc (3×20 mL), the combined organic phases were washed with H₂O, brine, and dried over Na₂SO₄, and filtered, and concentrated to give crude product (S)-tert-butyl 4-((R)-5-hydroxy-2-(tosyloxymethyl)pentyl)-2,2-dimethyloxazolidine-3-carboxylate (255 mg, 92%). It was used without further purification.

Step 10. (S)-tert-butyl 2,2-dimethyl-4-(((R)-tetrahydro-2H-pyran-3-yl)methyl)oxazolidine-3-carboxylate To a solution of (S)-tert-butyl 4-((R)-5-hydroxy-2-(tosyloxymethyl)pentyl)-2,2-dimethyloxazolidine-3-carboxylate (254 mg, 0.54 mmol) in anhydrous DMF (8 mL) at 0° C. under N₂ was added NaH (43 mg, 1.08 mmol). After stirred at this temperature for 1 hr, the reaction was quenched with aq. NH₄Cl and then evaporated to dryness. The residue was dissolved in EtOAc and H₂O, the separated aqueous phase was extracted with EtOAc. The combined organic phases were washed with H₂O, brine, and dried over Na₂SO₄, filtered, and evaporated. The residue was purified on silica gel column to afford (S)-tert-butyl 2,2-dimethyl-4-(((R)-tetrahydro-2H-pyran-3-yl)methyl)oxazolidine-3-carboxylate (136 mg, 84%).

EXAMPLE 8

2,2-dimethyl-4-(((R)-tetrahydro-2H-pyran-3-yl)methyl)oxazolidine

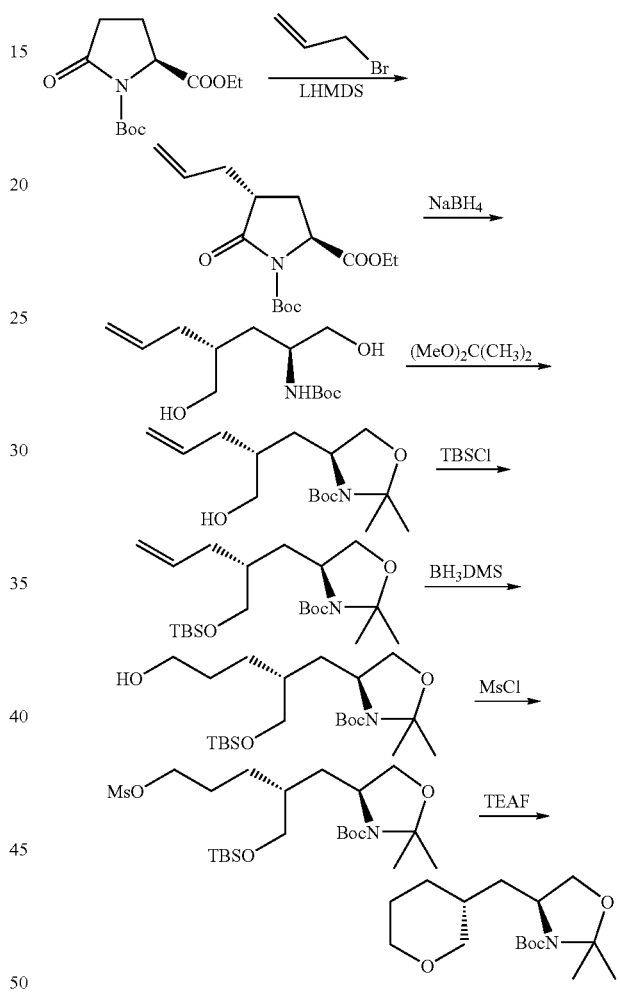

Step 1. (2S,4R)-1-tert-butyl 2-ethyl 4-allyl-5-oxopyrrolidine-1,2-dicarboxylate

To a solution of HMDS in anhydrous THF (200 mL) was added dropwise 2.5 M n-BuLi in hexane (130 mL) and the mixture was stirred at −78° C. for 1 hr. To a solution of (S)-1-tert-butyl 2-ethyl 5-oxopyrrolidine-1,2-dicarboxylate (80 g, 0.311 mol) in anhydrous THF (1600 mL) stirred at −78° C. was added lithium hexamethyldisilazide in THF. After the reaction mixture was stirred at −78° C. for 1 hr, 3-bromopropene (38.47 g, 0.318 mol) in THF (200 mL) was added and stirring was continued for 2 hr. The reaction mixture was quenched with saturated ammonium chloride solution (600 mL) at −78° C. and extracted with EtOAc (3×500 mL). The combined organic layers were dried over Na₂SO₄, filtered and evaporated to dryness. The crude product was separated by column chromatography to afford (2S,4R)-1-tert-butyl 2-ethyl 4-allyl-5-oxopyrrolidine-1,2-dicarboxylate (15 g, 16%).

Step 2. tert-butyl (2S,4R)-1-hydroxy-4-(hydroxymethyl)hept-6-en-2-ylcarbamate To a solution of (2S,4R)-1-tert-butyl 2-ethyl 4-allyl-5-oxopyrrolidine-1,2-dicarboxylate (30 g, 0.1 mol) in MeOH/H$_2$O (700/70 mL) was added NaBH$_4$ (25 g, 0.66 mol), the result mixture was stirred 1 hr at rt and quenched with sat. aq. NH$_4$Cl (300 mL). The organic solvent was removed under vacuum and extracted with EtOAc (3×250 mL). The combined organic phases were washed with brine (250 mL) and dried over anhydrous Na$_2$SO$_4$, filtered and evaporated to afford crude tert-butyl (2S,4R)-1-hydroxy-4-(hydroxymethyl)hept-6-en-2-ylcarbamate (22 g, 85%). It was used in the next step without further purification.

Step 3. (S)-tert-butyl 4-((R)-2-(hydroxymethyl)pent-4-enyl)-2,2-dimethyloxazolidine-3-carboxylate To a solution of tert-butyl (2S,4R)-1-hydroxy-4-(hydroxymethyl)hept-6-en-2-ylcarbamate (6.8 g, 26.2 mmol) in acetone (150 mL), PTSA (0.45 g, 2.62 mmol) was added. The reaction mixture was cooled to −20° C. followed by the addition of 2,2-dimethoxypropane (4.1 g, 39.4 mmol). The resulting mixture was stirred and allowed to warm to rt for 1 hr. TEA (0.5 mL) was then added and stirred for another 5 min. The solvent was removed under reduced pressure. The residue was dissolved in Et$_2$O (300 mL), washed with 1 N HCl (80 mL), sat. aq. NaHCO$_3$ (80 mL), brine (80 mL) successively, and dried, filtered, and concentrated under vacuum to give crude (S)-tert-butyl 4-((R)-2-(hydroxymethyl)pent-4-enyl)-2,2-dimethyloxazolidine-3-carboxylate (7.5 g, 96%). It was used without further purification.

Step 4. (S)-tert-butyl 4-((R)-2-((tert-butyldimethylsilyloxy)methyl)pent-4-enyl)-2,2-dimethyloxazolidine-3-carboxylate To a solution of (S)-tert-butyl 4-((R)-2-(hydroxymethyl)pent-4-enyl)-2,2-dimethyloxazolidine-3-carboxylate (11.5 g, 38.4 mmol), imidazole (7.84 g, 115.2 mmol) and DMAP (234 mg, 1.92 mmol) in CH$_2$Cl$_2$ (200 mL) was added a solution of TBSCl (8.68 g, 57.6 mmol) in CH$_2$Cl$_2$ (100 mL) dropwise. The reaction mixture was stirred at rt for overnight. The reaction was washed with water (100 mL) and the aqueous layer was extracted with CH$_2$Cl$_2$ (3×100 mL), the combined organic layers was washed with brine (70 mL), then dried over Na$_2$SO$_4$, filtered and concentrated to give the crude product, which was purified by column chromatography to afford (S)-tert-butyl 4-((R)-2-((tert-butyldimethylsilyloxy)methyl)pent-4-enyl)-2,2-dimethyloxazolidine-3-carboxylate (9 g, 57%).

Step 5. (S)-tert-butyl 4-((R)-2-((tert-butyldimethylsilyloxy)methyl)-5-hydroxypentyl)-2,2-dimethyloxazolidine-3-carboxylate A solution of (S)-tert-butyl 4-((R)-2-((tert-butyldimethylsilyloxy)methyl)pent-4-enyl)-2,2-dimethyloxazolidine-3-carboxylate (26 g, 63 mmol) in THF (200 mL) was cooled in an ice-bath, followed by dropwise addition of 10 M BH$_3$SMe$_2$ (6.3 mL). After stirring for 5 hr, 10% NaOH solution (32 mL) followed by 30% H$_2$O$_2$ (32 mL) were added carefully. The reaction mixture was stirred at rt for 16 hr. The reaction mixture was diluted with diethyl ether (500 mL) and the aqueous layer was extracted with diethyl ether (3×250 mL). The combined organic layers were washed with brine, dried over Na$_2$SO$_4$, filtered and concentrated to give the crude product, which was purified by column chromatography to afford (S)-tert-butyl 4-((R)-2-((tert-butyldimethylsilyloxy)methyl)-5-hydroxypentyl)-2,2-dimethyloxazolidine-3-carboxylate (19.6 g, 72%).

Step 6. (S)-tert-butyl 4-((R)-2-((tert-butyldimethylsilyloxy)methyl)-5-(methylsulfonyloxy)pentyl)-2,2-dimethyloxazolidine-3-carboxylate To a solution of (S)-tert-butyl 4-((R)-2-((tert-butyldimethylsilyloxy)methyl)-5-hydroxypentyl)-2,2-dimethyloxazolidine-3-carboxylate (32 g, 74.2 mmol) and Et$_3$N (22.5 g, 226 mmol) in CH$_2$Cl$_2$ (400 mL) was added a solution of MsCl (10.1 g, 89 mmol) in CH$_2$Cl$_2$ (50 mL) at 0-5° C. After addition, the reaction mixture was allowed to warm to rt and stir for 1 hr. The reaction was washed with water (200 mL) and the aqueous layer was extracted with CH$_2$Cl$_2$ (3×150 mL). The combined organic layers was washed with 10% citric acid (60 mL), sat. NaHCO$_3$ (60 mL) and brine (100 mL), then dried over Na$_2$SO$_4$, filtered and concentrated to give (S)-tert-butyl 4-((R)-2-((tert-butyldimethylsilyloxy)methyl)-5-(methylsulfonyloxy)pentyl)-2,2-dimethyloxazolidine-3-carboxylate (37.7 g, 100%), which was used in the next step without purification.

Step 7. (S)-tert-butyl 2,2-dimethyl-4-(((R)-tetrahydro-2H-pyran-3-yl)methyl)oxazolidine-3-carboxylate To a solution of (S)-tert-butyl 4-((R)-2-((tert-butyldimethylsilyloxy)methyl)-5-(methylsulfonyloxy)pentyl)-2,2-dimethyloxazolidine-3-carboxylate (37.7 g, 74.2 mmol) in THF (1000 mL) was added tetraethylammonium fluoride hydrate (41 g, 185.5 mmol) in portions. The reaction mixture was stirred under reflux overnight. The mixture was diluted with EtOAc (1000 mL), washed with water (300 mL) and brine (500 mL). The organic phase was dried over Na$_2$SO$_4$, filtered and concentrated in vacuo to give the crude product, which was purified by column chromatography to afford (S)-tert-butyl 2,2-dimethyl-4-(((R)-tetrahydro-2H-pyran-3-yl)methyl)oxazolidine-3-carboxylate (12.0 g, 54%).

EXAMPLE 9 tert-butyl (S)-1-amino-3-((R)-tetrahydro-2H-pyran-3-yl)propan-2-ylcarbamate

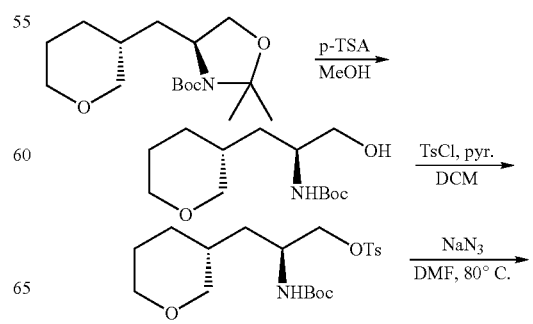

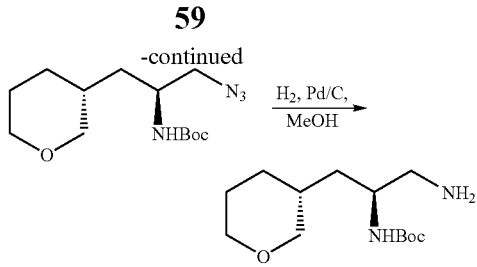

Step 1. Preparation of tert-butyl (S)-1-hydroxy-3-((R)-tetrahydro-2H-pyran-3-yl)propan-2-ylcarbamate To a solution of (S)-tert-butyl 2,2-dimethyl-4-(((R)-tetrahydro-2H-pyran-3-yl)methyl)oxazolidine-3-carboxylate (643 mg, 2.15 mmol) in MeOH (10 mL) was added p-TSA (37 mg, 0.22 mmol), then the solution was stirred at rt for 12 hr. TEA (2 mL) was added, followed by Boc$_2$O (46 mg, 0.21 mmol). After the addition the reaction solution was stirred for another 30 min. The organic solvent was removed under reduced pressure to give the crude product tert-butyl (S)-1-hydroxy-3-((R)-tetrahydro-2H-pyran-3-yl)propan-2-ylcarbamate. It was used in the next step without further purification. MS ESI+ve m/z 260 (M+1).

Step 2. Preparation of (S)-2-(tert-butoxycarbonylamino)-3-((R)-tetrahydro-2H-pyran-3-yl)propyl 4-methylbenzenesulfonate The above crude product tert-butyl (S)-1-hydroxy-3-((R)-tetrahydro-2H-pyran-3-yl)propan-2-ylcarbamate was dissolved in anhydrous DCM (22 mL). To this solution was added pyridine (2 mL) and TsCl (1.230 g, 6.45 mmol). After stirred at rt for 4 hr, another batch of pyridine (3 mL) and TsCl (0.700 g, 3.67 mmol) was added and stirred for another 12 hr. The reaction mixture was diluted with EtOAc (80 mL), washed with 1 N HCl (75 mL), followed by H$_2$O (2×30 mL), saturated aq. NaHCO$_3$, brine, and dried over anhydrous Na$_2$SO$_4$, and filtered, and concentrated under reduced pressure. The resulted slurry was purified through flash chromatography on silica gel (eluted with gradient system: 0-35% EtOAc in hexane) to afford (S)-2-(tert-butoxycarbonylamino)-3-((R)-tetrahydro-2H-pyran-3-yl)propyl 4-methylbenzenesulfonate, 670 mg, yield 75% for two steps. MS ESI+ve m/z 436 (M+Na).

Step 3. tert-butyl (S)-1-azido-3-((R)-tetrahydro-2H-pyran-3-yl)propan-2-ylcarbamate The solution of (S)-2-(tert-butoxycarbonylamino)-3-((R)-tetrahydro-2H-pyran-3-yl)propyl 4-methylbenzenesulfonate (132 mg, 0.32 mmol) and NaN$_3$ (62 mg, 0.95 mmol) in anhydrous DMF was heated to 80° C. under N$_2$ atmosphere for 1.5 hr, cooled to rt and diluted with EtOAc, and washed with H$_2$O (3×20 mL), followed by brine, and dried over anhydrous Na$_2$SO$_4$, and filtered, and concentrated under reduced pressure. The resulted slurry was purified through flash chromatography on silica gel (eluted with gradient system: 0-30% EtOAc in hexane) to afford tert-butyl (S)-1-azido-3-((R)-tetrahydro-2H-pyran-3-yl)propan-2-ylcarbamate 58 mg, yield 64%. MS ESI+ve m/z 307 (M+Na).

Step 4: tert-butyl (S)-1-amino-3-((R)-tetrahydro-2H-pyran-3-yl)propan-2-ylcarbamate Hydrogenation of tert-butyl (S)-1-azido-3-((R)-tetrahydro-2H-pyran-3-yl)propan-2-ylcarbamate (146 mg, 0.51 mmol) was carried out in MeOH (10 mL), 10% Pd/C (25 mg) under 40 psi of H$_2$ for 2 h. After filtration 114 mg of tert-butyl (S)-1-amino-3-((R)-tetrahydro-2H-pyran-3-yl)propan-2-ylcarbamate was obtained, yield 86%. MS ESI+ve m/z 259 (M+H).

EXAMPLE 10 tert-butyl (S)-1-amino-3-((R)-tetrahydro-2H-pyran-3-yl)propan-2-yl(methyl)carbamate

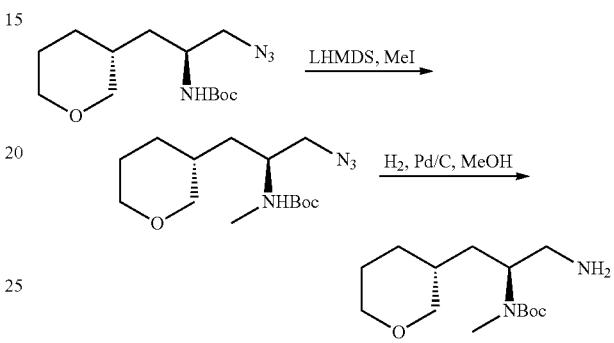

Step 1. tert-butyl (S)-1-azido-3-((R)-tetrahydro-2H-pyran-3-yl)propan-2-yl(methyl)carbamate To a solution of tert-butyl (S)-1-azido-3-((R)-2H-pyran-3-yl)propan-2-ylcarbamate (30 mg, 0.11 mmol) in anhydrous THF (4 mL) at −78° C. was added 1.0 M LHMDS solution in THF (253 μL, 0.25 mmol), then stirred at this temperature for 30 min. To this mixture was added MeI (125 μL, 0.22 mmol), then the temperature was allowed to warm to 0° C., and stand for 12 hr in the refrigerator. The reaction mixture was quenched with saturated aq. NH$_4$Cl, extracted with EtOAc (30 mL), the separated organic phase was washed with H$_2$O (2×10 mL), brine, and dried (Na$_2$SO$_4$), and filtered. The filtrate was concentrated, the resulting slurry was purified through flash chromatography on silica gel (eluted with gradient system, 0-30% EtOAc in hexane) to afford tert-butyl (S)-1-azido-3-((R)-tetrahydro-2H-pyran-3-yl)propan-2-yl(methyl)carbamate 31 mg, yield 100%. MS ESI+ve m/z 321 (M+Na).

Step 2. tert-butyl (S)-1-amino-3-((R)-tetrahydro-2H-pyran-3-yl)propan-2-yl(methyl)carbamate Hydrogenation of (S)-1-azido-3-((R)-tetrahydro-2H-pyran-3-yl)propan-2-yl(methyl)carbamate (62 mg, 0.51 mmol) was carried out in EtOAc (20 mL), 10% Pd/C (15 mg) under 40 psi of H$_2$ for 2 h. After filtration 52 mg of tert-butyl (S)-1-amino-3-((R)-tetrahydro-2H-pyran-3-yl)propan-2-ylcarbamate was obtained, yield 91%. MS ESI+ve m/z 273 (M+H).

Alternative Procedure I:

Alternatively, tert-butyl (S)-1-amino-3-((R)-tetrahydro-2H-pyran-3-yl)propan-2-yl(methyl)carbamate may be prepared by the following procedures:

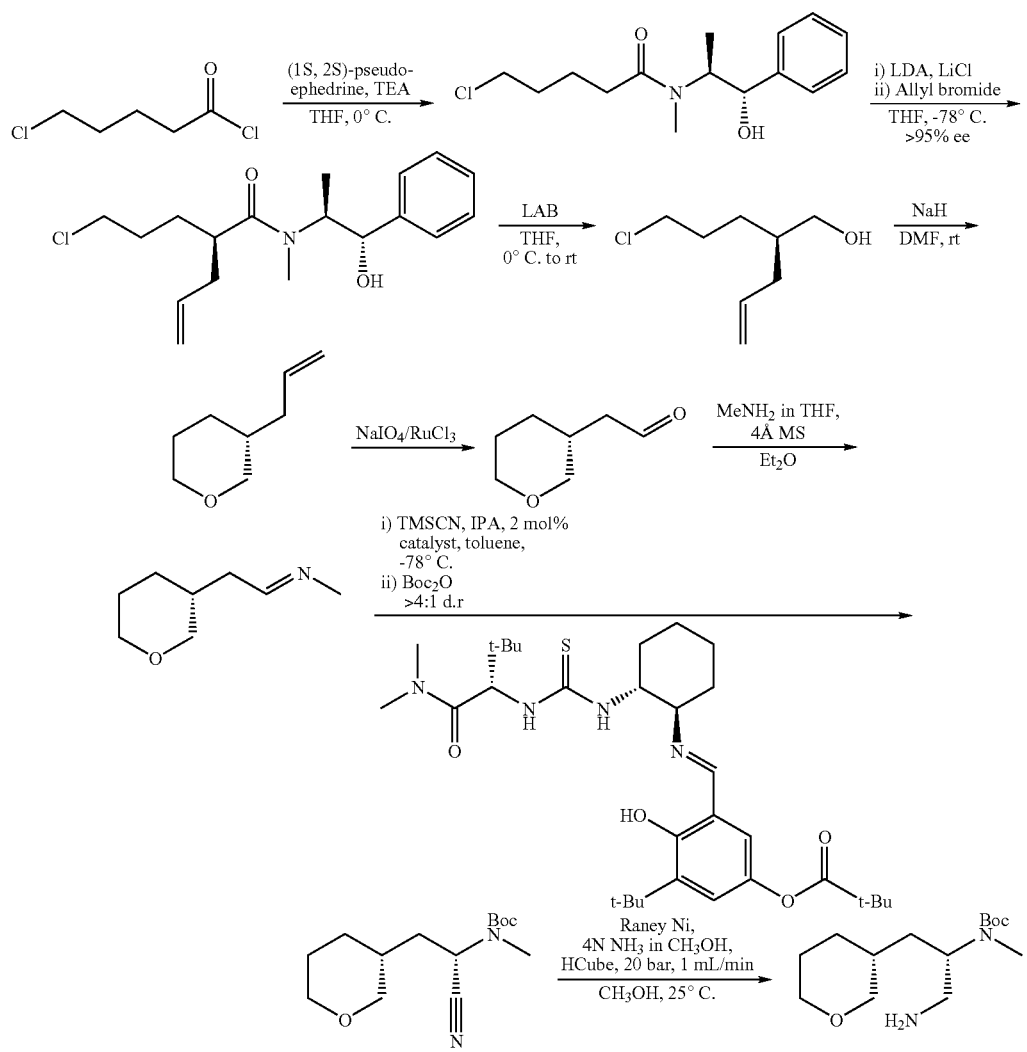

Step 1. 5-Chloro-N-((1S,2S)-1-hydroxy-1-phenyl-propan-2-yl)-N-methylpentanamide

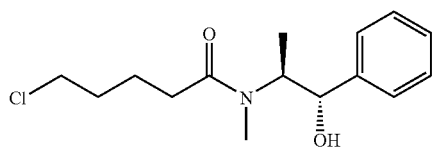

To a magnetically stirred solution of (1S,2S)-pseudoephedrine (60 g, 363.1 mmol) in THF (600 mL) at room temperature was added triethylamine (65.4 mL, 472 mmol) in one portion. The resulting white suspension was cooled to 0° C. A solution of 5-chloropentanoyl chloride (49 mL, 381 mmol) in THF (130 mL) was added dropwise to the mixture over 45 min using an addition funnel. The mixture was then allowed to stir at 0° C. for 30 min. H₂O (40 mL) was added and the resulting mixture was concentrated to ~10% of the original volume. The resulting solution was partitioned between H₂O/EtOAc and the layers were separated. The aqueous layer was extracted with EtOAc (600 mL). The combined organic layers were washed with saturated aqueous NaHCO₃, brine, dried over MgSO₄, filtered, and concentrated under reduced pressure to furnish the crude product as pale yellow oil. The crude amide was purified by flash chromatography (ISCO; 3×330 g column; CH₂Cl₂ to 5% MeOH/CH₂Cl₂) to provide the product as a clear, viscous oil. The residual MeOH was removed through azeotroping with toluene (3×100 mL) to provide 5-chloro-N-((1S,2S)-1-hydroxy-1-phenylpropan-2-yl)-N-methylpentanamide (96.2 g, 339 mmol, 93%). LCMS (m/z=266.0)

Step 2. (R)-2-(3-Chloropropyl)-N-((1S,2S)-1-hydroxy-1-phenylpropan-2-yl)-N-methylpent-4-enamide

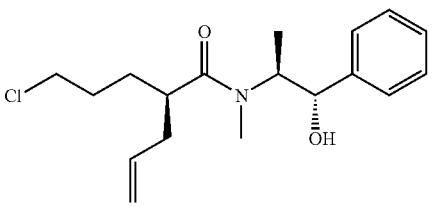

To a magnetically stirred suspension of LiCl (83 g, 1.96 mol) in THF (700 mL) at room temperature was added diisopropylamine (104 mL, 736 mmol) in one portion. nBuLi (2.5M in hexane, 281 mL, 703 mmol) was added dropwise over 30 min using an addition funnel. The light yellow mixture stirred at −78° C. for 20 min and then was warmed to 0° C. for 15 min. The mixture was then cooled to −78° C. and 5-chloro-N-((1S,2S)-1-hydroxy-1-phenylpropan-2-yl)-N-methylpentanamide (92.8 g, 327 mmol) in THF (330 mL) was added dropwise over 30 min using an addition funnel. The mixture was stirred at −78° C. for 1 h and then was warmed to 0° C. for 25 min. Allylbromide (41.5 mL, 490 mmol) was then added slowly over 2 min via syringe and then the reaction was warmed to room temperature. The reaction stirred at room temperature for 50 min and was judged complete by LC/MS. The mixture was cooled to 0° C. and saturated aqueous NaHCO$_3$ (400 mL) and H$_2$O (200 mL) were added. EtOAc was added, the phases were separated and the aqueous phase was extracted with EtOAc (1500 mL total). The combined with organic layers were washed with 1N HCl (4×150 mL), brine, dried over MgSO$_4$, filtered, and concentrated under reduced pressure to furnish (R)-2-(3-chloropropyl)-N-((1S,2S)-1-hydroxy-1-phenylpropan-2-yl)-N-methylpent-4-enamide as an orange oil (101.2 g, 312 mmol, 95%). The crude material was carried on without further purification. LC/MS (m/z=306.0).

Step 3. (R)-2-(3-Chloropropyl)pent-4-en-1-ol

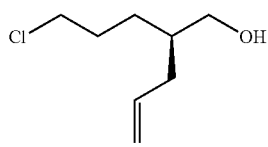

A magnetically stirred solution of diisopropylamine (184 mL, 1.29 mol) in THF (600 mL) was cooled to −78° C. nBuLi (2.5M in hexane, 482 mL, 1.21 mol) was added dropwise over 35 min using an addition funnel. The cloudy mixture stirred at −78° C. for 15 min and then was warmed to 0° C. for 15 min during which time the solution became clear and light yellow. Borane-ammonia (90%, 42 g, 1.24 mol) was added in four equal portions, one minute apart. (Caution: vigorous evolution of gas). The cloudy mixture was warmed to room temperature for 20 min and then was recooled to 0° C. (R)-2-(3-chloropropyl)-N-((1S,2S)-1-hydroxy-1-phenylpropan-2-yl)-N-methylpent-4-enamide (100.2 g, 309 mmol) in THF (300 mL) was added dropwise over 10 min using an addition funnel. The reaction was warmed to room temperature and stirred for 2.5 h. The reaction was cooled to −10° C. and was quenched with HCl (3M, 1500 mL). The phases were separated and the aqueous phase was extracted with Et$_2$O (2000 mL total). The combined organic layers were washed with 3N HCl, brine, dried over MgSO$_4$, filtered, and concentrated under reduced pressure to furnish the crude product as a yellow oil. The crude material was purified by flash chromatography (ISCO; 330 g column; Hexane to 30% EtOAc/Hexane) to provide (R)-2-(3-chloropropyl)pent-4-en-1-ol as a clear, viscous oil (32.6 g, 200 mmol, 65%); $^1$H NMR (400 MHz. CDCl$_3$) δ 5.82 (m, 1H), 5.07 (m, 2H), 3.78 (m, 1H), 3.58 (d, J=8.0 Hz, 2H), 3.54 (t, J=8 Hz, 2H), 2.14 (m, 2H), 1.85 (m, 2H), 1.64 (m, 1H), 1.49 (m, 1H).

Step 4. (R)-3-Allyl-tetrahydro-2H-pyran

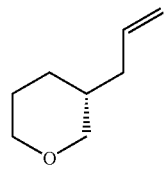

DMF (350 mL) was added to a round bottom flask containing NaH (60% w/w, 15 g, 0.376 mmol) and a magnetic stir bar. The suspension was cooled to 5-10° C. in an ice bath and stirred for 5 min. A solution of (R)-2-(3-chloropropyl)pent-4-en-1-ol (30.6 g, 188 mmol) in DMF (350 mL) was added via addition funnel over 25 min. Caution: Gas evolution and exotherm. The resulting creamy suspension was stirred for 30 min. The reaction was warmed to room temperature and the resulting beige suspension was stirred for 2 h, at which time it was judged complete by TLC. The reaction mixture was cooled to 0° C. and quenched by addition of H$_2$O (250 mL) and HCl (3N, 250 mL). The phases were separated and the aqueous phase was extracted with petroleum ether (4×250 mL). The combined with organic layers were washed with H$_2$O, brine, dried over MgSO$_4$, filtered, and concentrated under reduced pressure to furnish the crude product as a yellow oil. The crude material was purified by flash chromatography (ISCO; 120 g column; Hexane to 30% EtOAc/Hexane) to provide (R)-3-allyl-tetrahydro-2H-pyran as a clear oil (19.8 g, 157 mmol, 83%); $^1$H NMR (400 MHz. CDCl$_3$) δ 5.72-5.82 (m, 1H), 5.00-5.06 (m, 2H), 3.86-3.91 (m, 2H), 3.37 (m, 1H), 3.08 (t, J=12 Hz, 1H), 1.85-1.98 (m, 3H), 1.59-1.69 (m, 3H), 1.15-1.21 (m, 1H).

Step 5. (R)-2-(Tetrahydro-2H-pyran-3-yl)acetaldehyde

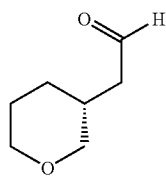

To a magnetically stirred solution of (R)-3-allyl-tetrahydro-2H-pyran (18.7 g, 148 mmol) in acetonitrile (740 mL) at room temperature was added RuCl$_3$.2H$_2$O (1.43 g, 5.92 mmol) in one portion. The resulting dark brown solution was stirred at room temperature for 5 min and then NaIO$_4$ (69 g, 326 mmol) was added in one portion. H$_2$O was added in small portions (10×8 mL) at 5 min intervals. The reaction was stirred at room temperature for 30 min, at which time it was judged complete by TLC. The reaction mixture was quenched by addition of saturated aqueous Na$_2$S$_2$O$_3$ (250 mL) and H$_2$O (1000 mL). The phases were separated and the aqueous phase was extracted with Et$_2$O (4×400 mL). The combined with organic layers were washed with H$_2$O, brine, dried over MgSO$_4$, filtered, and concentrated under reduced pressure to furnish the crude product as a yellow oil. The crude material was purified by flash chromatography (ISCO; 120 g column; Hexane to 40% EtOAc/Hexane) to provide (R)-2-(tetrahydro-2H-pyran-3-yl)acetaldehyde as a yellow oil (14.3 g, 111 mmol, 60%); ¹H NMR (400 MHz, CDCl₃) δ 9.78 (t, J=2, 1H), 3.84-3.88 (m, 2H), 3.40-3.47 (m, 1H), 3.17 (dd, J=11.2, 8.8 Hz, 1H), 2.31-2.41 (m, 2H), 2.21-2.28 (m, 1H), 1.88-1.93 (m, 1H), 1.61-1.72 (m, 2H), 1.29-1.33 (m, 1H).

Step 6. (R,E)-N-(2-(Tetrahydro-2H-pyran-3-yl)ethylidene)methanamine

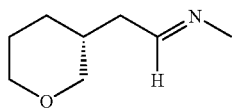

To a magnetically stirred solution of (R)-2-(tetrahydro-2H-pyran-3-yl)acetaldehyde (11 g, 85.8 mmol) in Et₂O (215 mL) at room temperature was added MeNH₂ (2M in THF, 215 mL, 429.2 mmol) and molecular sieves (4 Å, powdered, activated, 21.5 g). The reaction was stirred at room temperature for 1 h. The resulting mixture was then filtered and concentrated under reduced pressure to furnish (R,E)-N-(2-(tetrahydro-2H-pyran-3-yl)ethylidene)methanamine as a yellow oil (11.3 g, 80 mmol, 93%). The crude material was carried on without further purification. ¹H NMR (400 MHz, CDCl₃) δ 7.67 (m, 1H), 3.86-3.91 (m, 2H), 3.36-3.43 (m, 1H), 3.29 (s, 3H), 3.13 (dd, J=11.0, 9.8 Hz, 1H), 1.95-2.14 (m, 2H), 1.86-1.91 (m, 2H), 1.62-1.68 (m, 2H), 1.21-1.30 (m, 1H).

Step 7. tert-Butyl (S)-1-cyano-2-((R)-tetrahydro-2H-pyran-3-yl)ethyl(methyl)-carbamate

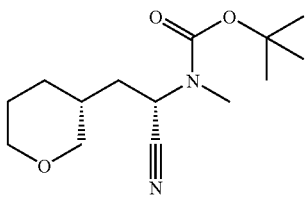

A 2 L, round bottom flask was charged with toluene (400 mL), a magnetic stir bar, (R,E)-N-(2-(Tetrahydro-2H-pyran-3-yl)ethylidene)methanamine (11.3 g, 80.1 mmol) and 3-{(E)-[((1R,2R)-2-{[({(1S)-1-[(dimethylamino)carbonyl]-2,2-dimethylpropyl}amino)carbonothioyl]amino}cyclohexyl)imino]methyl}-5-(1,1-dimethylethyl)-4-hydroxyphenyl 2,2-dimethylpropanoate (J. Am. Chem. Soc., 2002, 124, 10012-10014) (0.9 g, 1.6 mmol). The mixture was cooled to −78° C. and trimethylsilanecarbonitrile (21.4 mL, 160.2 mmol) was added dropwise over 15 min using an addition funnel. Isopropyl alcohol (12.3 mL, 160.2 mmol) was then added dropwise over 10 min. The reaction stirred at −78° C. for 3 h and then was warmed to room temperature and stirred for 1 h. Bis(1,1-dimethylethyl) dicarbonate (35.0 g, 160.2 mmol) was then added and the resulting mixture was stirred at room temperature for 1 h. The reaction was quenched by the addition of saturated aqueous NaHCO₃ (400 mL) and EtOAc (300 mL). The layers were separated and the aqueous layer was washed with EtOAc (100 mL). The combined organic layers were dried over Na₂SO₄, filtered, and concentrated under reduced pressure to give the crude product. The crude material was divided into two parts and each was purified by flash chromatography (ISCO; 120 g column; 0% to 10% EtOAc/Hexane over 30 min, then 10% EtOAc/Hexane 47 min, then 10% to 20% EtOAc/Hexane over 2 min, then 20% EtOAc/Hexane for 11 min). The two purified batches were combined to provide tert-butyl (S)-1-cyano-2-((R)-tetrahydro-2H-pyran-3-yl)ethyl(methyl)carbamate (18.9 g, 70 mmol, 86%) as an orange oil. ¹H NMR (400 MHz, CDCl₃) δ 5.00 (brs, 1H), 3.83-3.90 (m, 2H), 3.42-3.48 (m, 1H), 3.19 (dd, J=11.3, 8.6, 1H), 2.92 (s, 3H), 1.85-1.95 (m, 1H), 1.60-1.82 (m, 5H), 1.50 (s, 9H), 1.28-1.33 (m, 1H).

Step 8. tert-Butyl (S)-1-amino-3-((R)-tetrahydro-2H-pyran-3-yl)propan-2-yl(methyl)carbamate

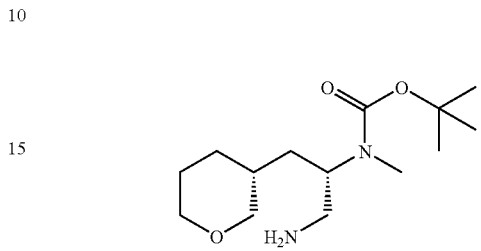

tert-Butyl (S)-1-cyano-2-((R)-tetrahydro-2H-pyran-3-yl) ethyl(methyl)carbamate (397 mg, 4:1 mixture of diastereomers at the alpha-amino stereocenter) was dissolved in a solution of 4M NH₃ in MeOH (15 mL) and passed through a Raney-nickel cartridge (CatCart®, 50 mm) on an in-line hydrogenation apparatus (H-Cube) with the following settings: ambient temperature (14° C.), flow rate 1.0 mL/min, H₂ pressure 30 atm. The solution was recirculated so that the product solution was fed back into the apparatus. After thirty minutes, TLC analysis (1:9 MeOH/CH₂Cl₂, KMnO₄ stain) showed complete conversion of the starting material. After 60 min total reaction time, the solution was evaporated to yield 371 mg (92%) of tert-butyl (S)-1-amino-3-((R)-tetrahydro-2H-pyran-3-yl)propan-2-yl(methyl)carbamate as a clear, rose-colored oil. LC-MS (ELSD) m/e 273.6 (M+H)⁺.

Alternative Procedure II:

Alternatively, tert-butyl (S)-1-amino-3-((R)-tetrahydro-2H-pyran-3-yl)propan-2-yl(methyl)carbamate may also be prepared by the following procedures:

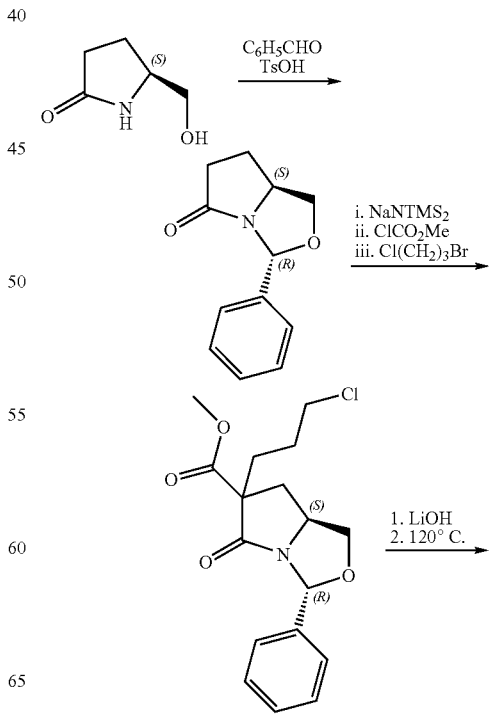

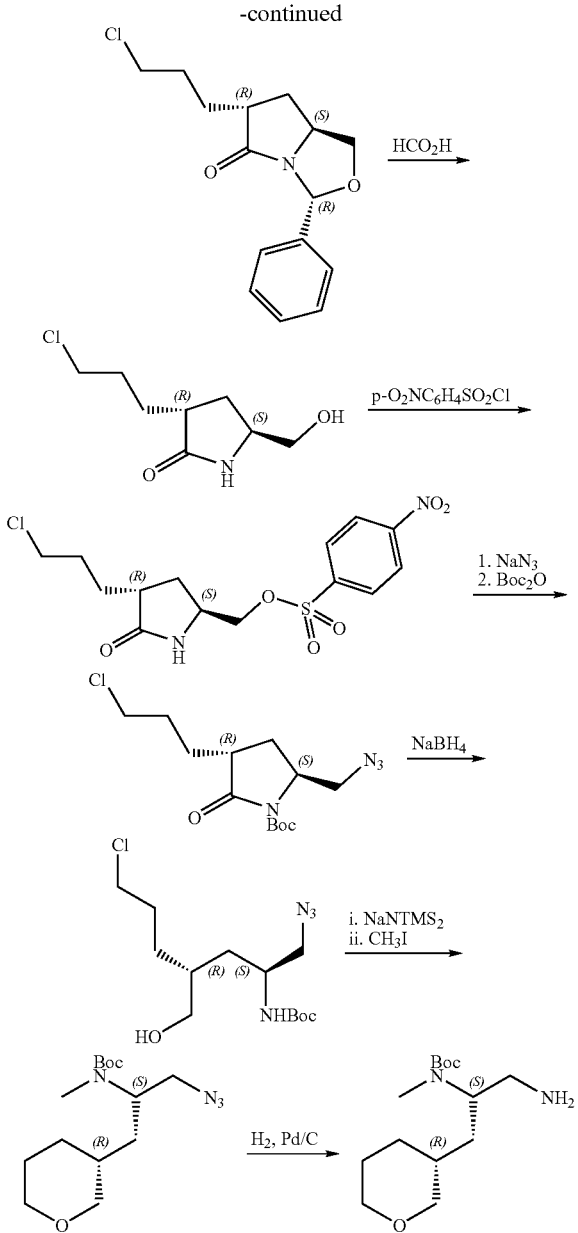

~90% conversion of the starting amide to the β-dicarbonyl intermediate at 1.28 min. A second portion of methyl chloroformate solution (1.75 g, 1.43 mL, 0.0185 mol, in 1.8 mL of THF) was added over 10 min and the mixture stirred an additional hour at 0° C. After this time the starting amide was consumed. 1-Bromo-3-chloropropane (69.3 mL, 111 g, 0.704 mol, 4.0 equiv) was added and the mixture heated to reflux for 17 h. After this time LC/MS showed formation of the desired alkylated compound. The mixture was cooled to ambient temperature and the quenched by addition of 0.5 M HCl. A ~5° C. exotherm was observed. The mixture was transferred to a separatory funnel containing 100 mL of EtOAc and the layers separated. The organic layer was washed with brine, and evaporated. The crude (3R,7aS)-methyl 6-(3-chloropropyl)-5-oxo-3-phenyl-hexahydropyrrolo[1,2-c]oxazole-6-carboxylate (62.05 g, contaminated with Cl(CH₂)₃Br) was used in the next step with no further purification.

Step 2. (3R,7aS)-6-(3-chloropropyl)-5-oxo-3-phenyl-hexahydropyrrolo[1,2-c]oxazole-6-carboxylic acid The (3R,7aS)-methyl 6-(3-chloropropyl)-5-oxo-3-phenyl-hexahydropyrrolo[1,2-c]oxazole-6-carboxylate (36.90 g) was dissolved in 300 mL of THF and the mixture cooled to 0° C. A solution of LiOH.H₂O (22.97 g, 0.548 mol, 5.0 equiv) in water (273 mL, 2.0 M) was cooled to 5° C. and added to the THF solution. The mixture was stirred at 10° C. and the progress of the hydrolysis monitored by LC/MS. After 3 h the methyl ester was completely consumed. EtOAc (100 mL) was added and concentrated HCL added till the pH<2. The mixture was transferred to a separatory funnel and the layers separated. The aqueous layer was extracted with 100 mL EtOAc, the combined organic layers washed with brine, dried over Na₂SO₄, filtered and evaporated. The (3R,7aS)-6-(3-chloropropyl)-5-oxo-3-phenyl-hexahydropyrrolo[1,2-c]oxazole-6-carboxylic acid was isolated as a tan solid (32.65 g, 92% yield) after removal of residual solvent in vacuo.

Step 3. (3R,6R,7aS)-6-(3-Chloropropyl)-3-phenyl-dihydropyrrolo[1,2-c]oxazol-5(1H,3H,6H)-one The (3R,7aS)-6-(3-chloropropyl)-5-oxo-3-phenyl-hexahydropyrrolo[1,2-c]oxazole-6-carboxylic acid (32.65 g, 0.101 mol) was slurried in 300 mL of anhydrous toluene. The temperature of the mixture was raised to 120° C. over a ~1 h period, and maintained at 120° C. for 2 h. After this time LC/MS analysis showed formation of the desired amide. The mixture was cooled to ambient temperature and transferred to a separatory funnel. The mixture was washed with 100 mL of half-saturated NaHCO₃ solution and brine. During this process some insoluble material formed at the interface. This material was discarded. The toluene solution was stirred with 5 g of activated carbon (Norit, neutral) for 1 h, then filtered through a pad of Celite and evaporated. The amber syrup was placed on the vacuum line overnight. This afforded 26.7 g (94% yield) of (3R,6R,7aS)-6-(3-chloropropyl)-3-phenyl-dihydropyrrolo[1,2-c]oxazol-5(1H,3H,6H)-one.

Step 4. (3R,5S)-3-(3-Chloropropyl)-5-(hydroxymethyl)pyrrolidin-2-one

The (3R,6R,7aS)-6-(3-chloropropyl)-3-phenyl-dihydropyrrolo[1,2-c]oxazol-5(1H,3H,6H)-one (13.6 g, 47.9 mmol, 1.0 equiv) was dissolved in a mixture of THF (100 mL): formic acid (85%, 62.5 mL):H₂O (31 mL) and the solution heated to 40° C. for 3.5 h. After this time the animal was consumed and the desired alcohol was contaminated with Step 1. (3R,7aS)-Methyl 6-(3-chloropropyl)-5-oxo-3-phenyl-hexahydropyrrolo[1,2-c]oxazole-6-carboxylate The aminal (3R,7aS)-3-phenyl-dihydropyrrolo[1,2-c]oxazol-5(1H,3H,6H)-one (35.77 g, 0.176 mol, 1.0 equiv, crude, [J. Org. Chem. 1986, 51, 3140]) was dissolved in 100 mL of THF and the mixture cooled to −10° C. (ice/acetone bath) in a 1-L 3-neck flask equipped with thermocouple, overhead stirrer, reflux condenser and nitrogen inlet. A solution of NaNTMS₂ (2.0 M, 193.6 mL, 0.387 mol, 2.2 equiv) was added via dropping funnel over a 1 h period while maintaining the internal temperature between −5 and 0° C. The dark orange-brown reaction mixture stirred for 30 min. A solution of methyl chloroformate (17.5 g, 14.3 mL, 0.185 mol, 1.05 equiv) in 9 mL of THF was added via syringe pump over a 1 h period. After addition was completed the mixture was stirred at 0° C. for 1 h, them sampled by LC/MS. This showed varying amounts of the formate ester. The solution was evaporated using a rotory evaporator, maintaining the bath temperature below 25° C. A solution of 1.9 M LiOH was added to the residue till a pH>12 was achieved and the mixture stirred for 20 min. After this time no formate ester was observed. EtOAc (250 mL was added and the mixture transferred to a separatory funnel. The layers were separated and the aqueous layer was extracted with 4×50 mL of EtOAc. The combined extracts were dried over $Na_2SO_4$, filtered and evaporated. Hexanes (~200 mL) were added to the residue and the biphasic mixture heated to ~40° C. The hexanes were decanted off and the procedure repeated twice. The resulting syrup was placed on a vacuum line where it solidified to yield (3R,5S)-3-(3-chloropropyl)-5-(hydroxymethyl)pyrrolidin-2-one as an off-white solid (7.51 g 82% yield). An additional 0.80 g of material may be obtained by saturating the above aqueous solution with NaCl and extracting with 4×50 mL of $CH_2Cl_2$.

Step 5. ((2S,4R)-4-(3-Chloropropyl)-5-oxopyrrolidin-2-yl)methyl 4-nitrobenzenesulfonate The (3R,5S)-3-(3-chloropropyl)-5-(hydroxymethyl)pyrrolidin-2-one (8.31 g, 43.4 mmol, 1.0 equiv), p-nitrobenzenesulfonylchloride (10.57 g, 47.7 mmol, 1.1 equiv) and DMAP (0.53 g, 4.4 mmol, 0.1 equiv) were added to a 500 mL round-bottom flask and dissolved in THF (100 mL) under nitrogen. Triethylamine (8.77 g, 12.1 mL, 86.7 mmol, 2.0 equiv) was added via syringe and the resulting solution stirred for 17 h at ambient temperature. After this time complete formation of the desired nosylate was observed by LC/MS analysis. The mixture was diluted with 50 mL of EtOAc and the amines quenched by addition of 100 mL of 1.0 M HCl. The layers were separated and the organic layer washed with brine, dried over $Na_2SO_4$, filtered and evaporated. The pale yellow solid was washed with ether and residual solvent removed in vacuo. This afforded 14.02 g (86% yield) of ((2S,4R)-4-(3-chloropropyl)-5-oxopyrrolidin-2-yl)methyl 4-nitrobenzenesulfonate.

Step 6. (3R,5S)-5-(Azidomethyl)-3-(3-chloropropyl)pyrrolidin-2-one

The ((2S,4R)-4-(3-chloropropyl)-5-oxopyrrolidin-2-yl)methyl 4-nitrobenzenesulfonate (18.05 g, 45.2 mmol) and $NaN_3$ (3.23 g, 49.7 mmol, 1.1 equiv) were stirred in 100 mL of DMF for 19 h. After this time a white solid had formed and LC/MS analysis showed formation of the desired azide. The DMF was removed in vacuo and the residue partitioned between $EtOAc/H_2O$ (100+100 mL). The mixture was transferred to a separatory funnel and the layers separated. The aqueous layer was extracted with 100 mL additional EtOAc and the combined organic extracts washed with brine, dried over $Na_2SO_4$, filtered and evaporated. The (3R,5S)-5-(azidomethyl)-3-(3-chloropropyl)pyrrolidin-2-one was isolated as a pale yellow syrup (9.08 g, 94% yield).

Step 7. (3R,5S)-tert-Butyl 5-(azidomethyl)-3-(3-chloropropyl)-2-oxopyrrolidine-1-carboxylate The (3R,5S)-5-(azidomethyl)-3-(3-chloropropyl)pyrrolidin-2-one (9.08 g, 41.9 mmol, 1.0 equiv), Boc-anhydride (11.43 g, 52.4 mmol, 1.25 equiv) and DMAP (1.28 g, 10.4 mmol, 0.25 equiv) were dissolved in acetonitrile (100 mL) and the mixture stirred for 3 h at ambient temperature. After this time the desired carbamate was formed. Solution was evaporated and the product purified by flash chromatography on silica, eluting with 0-27% EtOAc in hexanes. This provided 10.1 g (67% yield) of (3R,5S)-tert-butyl 5-(azidomethyl)-3-(3-chloropropyl)-2-oxopyrrolidine-1-carboxylate as a colorless syrup.

Step 8. tert-Butyl (2S,4R)-1-azido-7-chloro-4-(hydroxymethyl)heptan-2-ylcarbamate The (3R,5S)-tert-butyl 5-(azidomethyl)-3-(3-chloropropyl)-2-oxopyrrolidine-1-carboxylate (10.11 g, 31.9 mmol, 10. equiv) was dissolved in 200 mL of MeOH. Solid $NaBH_4$ was added in ~1 g portions at a rate to maintain the reaction temperature at ~27° C. Subsequent portions of $NaBH_4$ were added only after the previous charge had completely dissolved. After the addition of ~3 g of $NaBH_4$ (~80 mmol, 2.5 equiv) over a 3 h period, LC/MS analysis showed >95% conversion to the desired alcohol. The residual hydride reagent was quenched by cooling the mixture to 0° C. and carefully adding 1.0 M HCl until $H_2$ evolution ceased. The methanol was removed in vacuo and the mixture diluted with ~200 mL of EtOAc. The mixture was transferred to a separatory funnel and the layers separated. The aqueous layer was extracted with additional EtOAc and the combined organic layers washed with brine, dried over $Na_2SO_4$, filtered through a pad of silica and evaporated. This yielded ~10 g of tert-butyl (2S,4R)-1-azido-7-chloro-4-(hydroxymethyl)heptan-2-ylcarbamate which possessed sufficient purity to employ in the subsequent step with no further purification.

Step 9. tert-Butyl (S)-1-azido-3-((R)-tetrahydro-2H-pyran-3-yl)propan-2-yl(methyl)carbamate The tert-butyl (2S,4R)-1-azido-7-chloro-4-(hydroxymethyl)heptan-2-ylcarbamate (1.59 g, 4.97 mmol, 1.0 equiv) was dissolved in 15 mL of DMF and the solution cooled to 0° C. A solution of $NaNTMS_2$ (1.0 M, 14.9 mmol, 3.0 equiv) was added via syringe at such a rate that the internal reaction temperature remains below 5° C. After stirring for 2 h LC/MS analysis showed formation of the cyclised product. Dimethylsulfate (940 mg, 0.71 mL, 7.5 mmol, 1.5 equiv) was added and the reaction mixture stirred overnight with concomitant warming to ambient temperature. LC/MS analysis showed formation of the desired methylated carbamate. The reaction was quenched by addition of 10% $K_2CO_3$ solution (~30 mL) and the mixture stirred for 0.5 h. The volatile materials were removed in vacuo and the residue partitioned between EtOAc/water. The layers were separated and the organic layer washed with brine, dried over $Na_2SO_4$, filtered and evaporated. The product was purified by flash chromatography on silica (40 g), eluting with 0-7% EtOAc in hexanes. This afforded 1.21 g (82% yield) of the desired tert-butyl (S)-1-azido-3-((R)-tetrahydro-2H-pyran-3-yl)propan-2-yl(methyl)carbamate as a colorless liquid.

Step 10. tert-Butyl (S)-1-amino-3-((R)-tetrahydro-2H-pyran-3-yl)propan-2-yl(methyl)carbamate The tert-butyl (S)-1-azido-3-((R)-tetrahydro-2H-pyran-3-yl)propan-2-yl(methyl)carbamate (2.1 g, 7.04 mmol, 1.0 equiv) and Pd/C (10%, 200 mg) were added to a flask. THF (30 mL) was added and the flask fitted with a gas inlet connected to a balloon of hydrogen gas. The flask was evacuated and back-filled with $H_2$ from the balloon. This was repeated twice and the reaction mixture stirred for 17 h at ambient temperature. Analysis by LC/MS showed complete conversion to the desired amine. The catalyst was removed by filtration through a pad of Celite and the mixture evaporated.

This provided 1.82 g (94%) of tert-butyl (S)-1-amino-3-((R)-tetrahydro-2H-pyran-3-yl)propan-2-yl(methyl)carbamate.

Alternative Procedure III:

Alternatively, tert-butyl (S)-1-amino-3-((R)-tetrahydro-2H-pyran-3-yl)propan-2-yl(methyl)carbamate may be prepared by the following procedures:

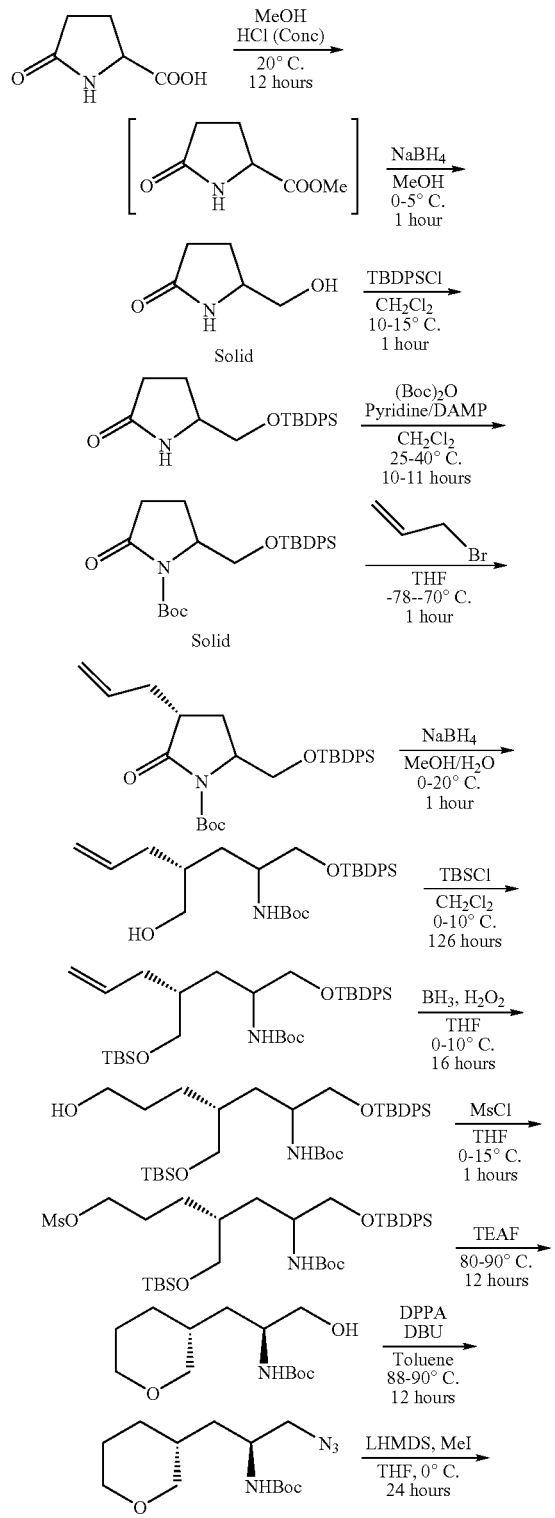

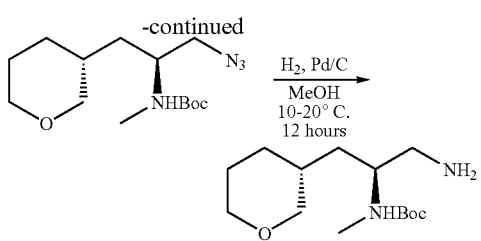

Alternative Procedure IV:

Alternatively, tert-butyl (S)-1-amino-3-((R)-tetrahydro-2H-pyran-3-yl)propan-2-yl(methyl)carbamate may also be prepared by the following process where chiral hydrogenation catalysts may be used in a series of hydrogenation steps to provide enantiomerically enriched intermediates:

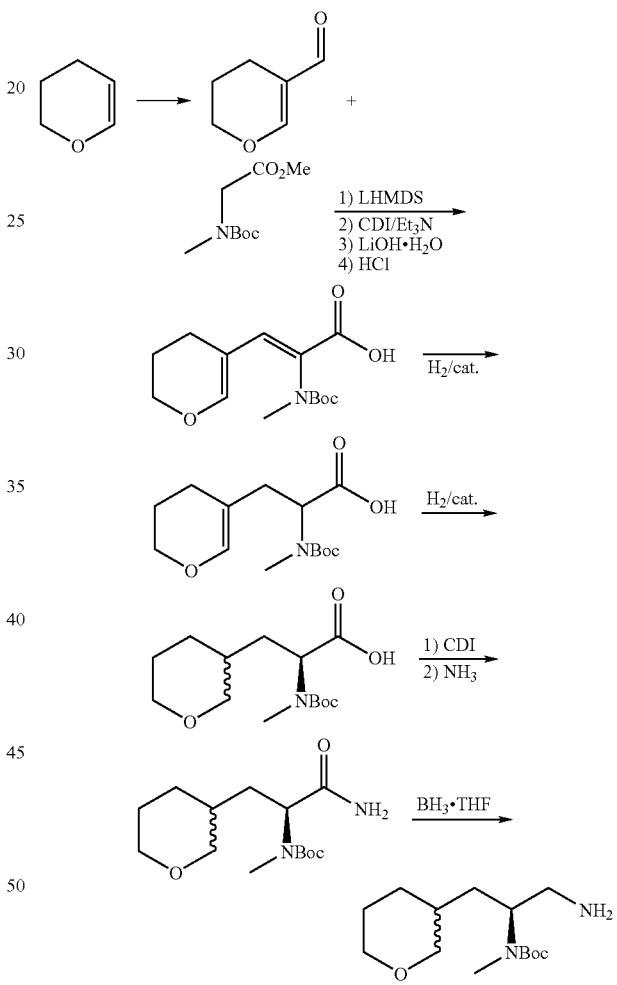

For example, hydrogenation of the dihydropyran-ene-amine to form the dihydropyran-amine may be accomplished in methanol, at 25° C., using about 88-110 psi hydrogen pressure, using 1-2 mol % of a catalyst generated from [Rh(nbd)$_2$]BF$_4$ and SL-M004-1 (SL-M004-1: (αR,αR)-2,2'-bis(α-N,N-dimethyl-aminophenylmethyl)-(S,S)-1,1'-bis[di(3,5-dimethyl-4-methoxyphenyl)phosphino]ferrocene, available from Solvias, Inc. Fort Lee, N.J.). Hydrogenation of the dihydropyran-amine to form the tetrahydropyran-amine may be accomplished at 50° C., using about 80 bar hydrogen pressure and 4 mol % catalyst loading of a catalyst generated from [Rh(COD)$_2$]O$_3$SCF$_3$ and SL-A109-2 (solvent: THF) or [Rh(nbd)$_2$]BF$_4$ and SL-A109-2 (solvent: methanol) (SL- A109-2: (S)-(6,6'-dimethoxybiphenyl-2,2'-diyl)-bis[bis(3,5-di-tert-butyl-4-methoxyphenyl)phosphine], available from Solvias, Inc. Fort Lee, N.J.).

EXAMPLE 11

(S)-2-(3-Chloropropyl)pent-4-en-1-ol

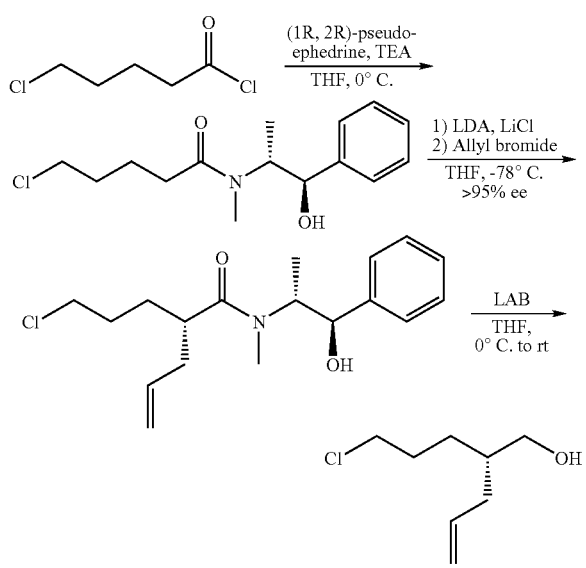

Step 1. 5-Chloro-N-((1R,2R)-1-hydroxy-1-phenyl-propan-2-yl)-N-methylpentanamide

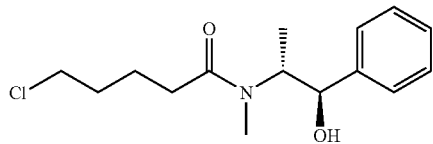

5-Chloro-N-((1R,2R)-1-hydroxy-1-phenylpropan-2-yl)-N-methylpentanamide was prepared from 5-chloropentanoyl chloride (7.8 mL, 60.4 mmol) and (1R,2R)-pseudoephedrine (9.9 g, 60.4 mmol) according to the method described in Example 10a, Step 1.

Step 2. (S)-2-(3-Chloropropyl)-N-((1R,2R)-1-hydroxy-1-phenylpropan-2-yl)-N-methylpent-4-enamide

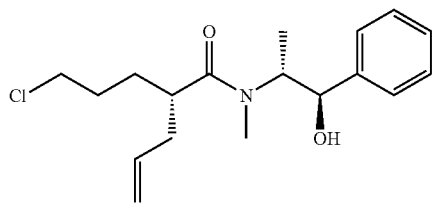

(S)-2-(3-Chloropropyl)-N-((1R,2R)-1-hydroxy-1-phenyl-propan-2-yl)-N-methylpent-4-enamide was prepared from 5-chloro-N-((1R,2R)-1-hydroxy-1-phenylpropan-2-yl)-N-methylpentanamide (17.7 g, 60.2 mmol) according to the method described in Example 10a, Step 2.

Step 3. (S)-2-(3-Chloropropyl)pent-4-en-1-ol

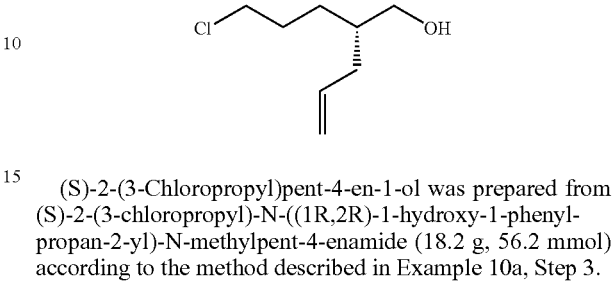

(S)-2-(3-Chloropropyl)pent-4-en-1-ol was prepared from (S)-2-(3-chloropropyl)-N-((1R,2R)-1-hydroxy-1-phenyl-propan-2-yl)-N-methylpent-4-enamide (18.2 g, 56.2 mmol) according to the method described in Example 10a, Step 3.

EXAMPLE 12 tert-Butyl (S)-1-amino-3-((R)-tetrahydro-2H-pyran-3-yl)propan-2-yl(ethyl)carbamate

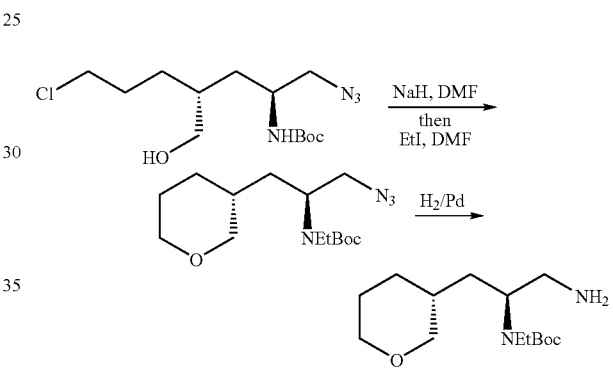

Step 1. tert-Butyl (S)-1-azido-3-((R)-tetrahydro-2H-pyran-3-yl)propan-2-yl(ethyl)carbamate To a 0° C. solution of crude tert-butyl (2S,4R)-1-azido-7-chloro-4-(hydroxymethyl)heptan-2-ylcarbamate (3.20 g, 10.0 mmol) in anhydrous DMF (50 mL) was added NaH (60% in mineral oil, 2.0 g, 50.0 mmol), 5 min later the temperature was allowed to warm to room temperature and stirred another 1.5 h. Ethyl iodide (4.68 g, 2.4 mL, 30.0 mmol) was added and stirred overnight at room temperature. The reaction was quenched with sat. aq. NH$_4$Cl at 0° C., and extracted with EA (70 mL), the separated organic phase was washed with H$_2$O (2×50 mL), brine (50 mL) successively, and dried over Na$_2$SO$_4$ and concentrated to afford an oil, which was purified on flash chromatography on silica gel and eluted with ethyl acetate/hexane (0-20%) to afford 1.8 g of tert-butyl (S)-1-azido-3-((R)-tetrahydro-2H-pyran-3-yl)propan-2-yl(ethyl)carbamate. MS ESI+ve m/z: 313 (M+H)$^+$.

Step 2. tert-Butyl (S)-1-amino-3-((R)-tetrahydro-2H-pyran-3-yl)propan-2-yl(ethyl)carbamate tert-Butyl (S)-1-amino-3-((R)-tetrahydro-2H-pyran-3-yl)propan-2-yl(ethyl)carbamate was prepared using procedures analogous to those described Example 10e, Step 10 using tert-butyl (S)-1-azido-3-((R)-tetrahydro-2H-pyran-3-yl)propan-2-yl(ethyl)carbamate.

EXAMPLE 13 methyl 2-((R)—((R)-1-((S)-2-amino-3-((R)-tetrahydro-2H-pyran-3-yl)propylcarbamoyl)piperidin-3-yl)(3-chlorophenyl)methoxy)ethylcarbamate (Compound 1)

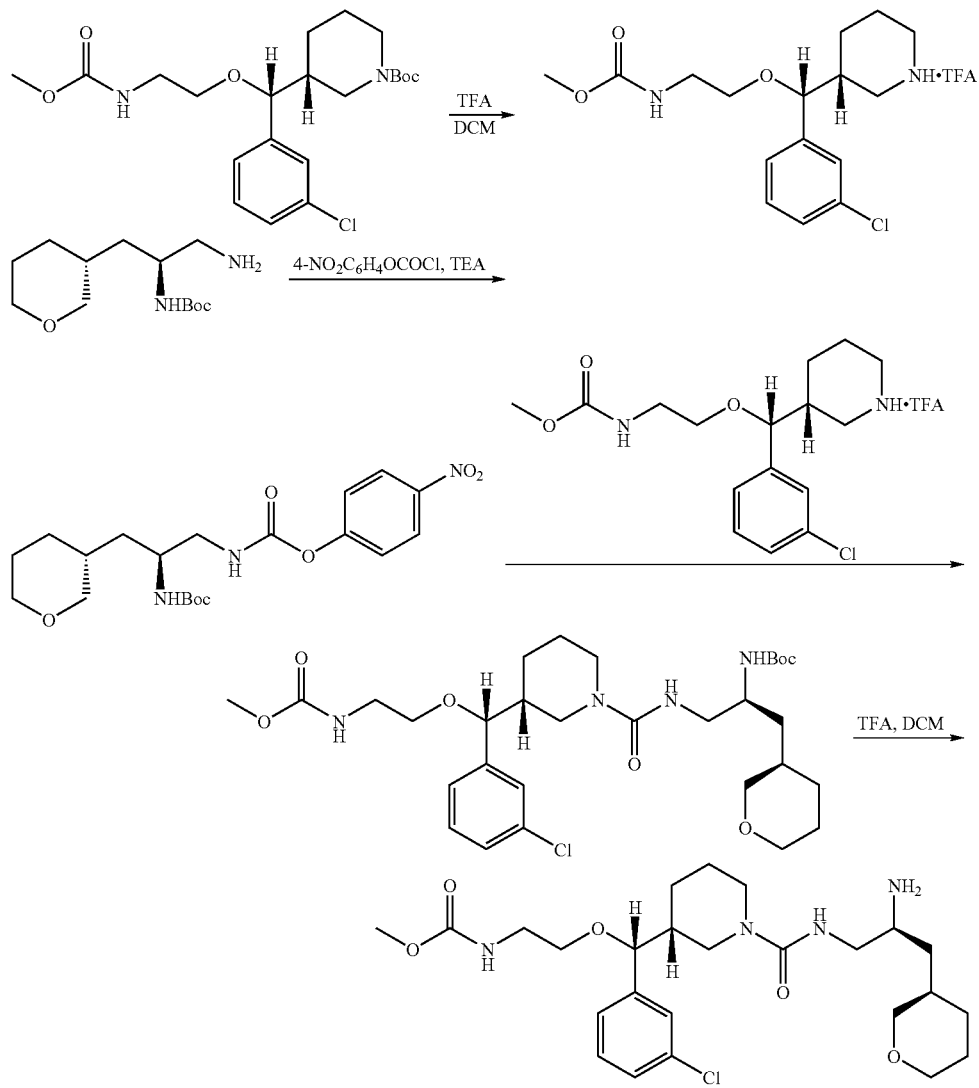

Step 1. methyl 2-((R)-(3-chlorophenyl)((R)-piperidin-3-yl)methoxy)ethylcarbamate.TFA salt The solution of (R)-tert-butyl 3-((R)-(3-chlorophenyl)(2-(methoxycarbonylamino)ethoxy)methyl)piperidine-1-carboxylate (2.247 g, 5.26 mmol) in mixed solvent of DCM/TFA (24 mL, 3:1, v/v) was stirred at rt for 30 min. The solvents was removed in vacuo to produce 2-((R)-(3-chlorophenyl)((R)-piperidin-3-yl)methoxy)ethylcarbamate TFA salt in quantitative yield. MS ESI+ve m/z 327 (M+H).

Step 2. (4-nitrophenyl) (S)-2-(N-(tert-butoxycarbonyl)amino)-3-((R)-tetrahydro-2H-pyran-3-yl)propylcarbamate To a solution of tert-butyl (S)-1-amino-3-((R)-tetrahydro-2H-pyran-3-yl)propan-2-ylcarbamate (20.8 mg, 0.081 mmol) in anhydrous DCM (9 mL) was added 4-nitrophenyl chloroformate (17.1 mg, 0.085 mmol), followed by TEA (12.2 mg, 17 µL, 0.12 mmol). The resulting solution was stirred at rt for 5 min (monitored by LC-MS) and diluted to 12 mL. An aliquot of the carbamate mixture solution (2 mL) was used for the next step without purification.

Step 3. 2-((R)—((R)-1-((S)-2-(Boc-amino)-3-((R)-tetrahydro-2H-pyran-3-yl)propylcarbamoyl)piperidin-3-yl)(3-chlorophenyl)methoxy)ethylcarbamate To (4-nitrophenyl) (S)-2-(N-(tert-butoxycarbonyl)amino)-3-((R)-tetrahydro-2H-pyran-3-yl)propylcarbamate solution (2 mL, 0.013 mmol) was added 2-((R)-(3-chlorophenyl)((R)-piperidin-3-yl)methoxy)ethylcarbamate TFA salt (7.0 mg, 0.016 mmol), followed by excess TEA (0.3 mL). The mixture was stirred for 30 min, then the solvent was removed in vacuo. The resulting oil was purified on preparative HPLC to give methyl 2-((R)—((R)-1-((S)-2-(Boc-amino)-3-((R)-tetrahydro-2H-pyran-3-yl)propylcarbamoyl)piperidin-3-yl)(3-chlorophenyl)methoxy)ethylcarbamate 5 mg, yield 63%. MS ESI+ve m/z 611 (M+H).

Step 4. methyl 2-((R)—((R)-1-((S)-2-amino-3-((R)-tetrahydro-2H-pyran-3-yl)propylcarbamoyl)piperidin-3-yl)(3-chlorophenyl)methoxy)ethylcarbamate TFA salt The 2-((R)—((R)-1-((S)-2-(Boc-amino)-3-((R)-tetrahydro-2H-pyran-3-yl)propylcarbamoyl)piperidin-3-yl)(3-chlorophenyl)methoxy)ethylcarbamate (5 mg, 0.008 mmol) was dissolved in DCM/TFA (3/1 mL). The solution was stirred for 30 min and concentrated. The crude mixture was purified on preparative HPLC to afford 2-((R)—((R)-1-((S)-2-amino-3-((R)-tetrahydro-2H-pyran-3-yl)propylcarbamoyl)piperidin-3-yl)(3-chlorophenyl)methoxy)ethylcarbamate TFA salt 2.8 mg, yield 54%. $^1$H NMR (CD$_3$OD) δ 7.36-7.32 (m, 3H), 7.23 (d, J=7.6 Hz, 1H), 4.20 (br d, J=13.6 Hz, 1H), 4.04 (d, J=8.8 Hz, 1H), 3.89-3.78 (m, 3H), 3.64 (s, 3H), 3.48-3.42 (m, 2H), 3.37 (m, 1H), 3.28-3.24 (m, 5H), 3.15 (dd, J=10.8, 9.2 Hz, 1H), 2.92 (m, 2H), 1.97 (m, 1H), 1.78 (m, 2H), 1.68-1.54 (m, 4H), 1.45-1.07 (m, 5H). MS ESI+ve m/z 511 (M+H).

The following compounds were prepared following procedures analogous to those described above and isolated as their TFA salts:

1) methyl 2-((R)—((R)-1-((S)-2-amino-3-((R)-tetrahydro-2H-pyran-3-yl)propylcarbamoyl)piperidin-3-yl)(3-fluorophenyl)methoxy)ethylcarbamate (compound 2) using trifluoroacetic acid salt of methyl 2-((R)-(3-fluorophenyl)((R)-piperidin-3-yl)methoxy)ethylcarbamate in Step 2.
2) methyl 2-((R)—((R)-1-((s)-2-amino-3-((R)-tetrahydro-2H-pyran-3-yl)propylcarbamoyl)piperidin-3-yl)(3-chloro-5-fluorophenyl)methoxy)ethylcarbamate (compound 3) using trifluoroacetic acid salt of methyl 2-((R)-(3-chloro-5-fluorophenyl)((R)-piperidin-3-yl)methoxy)ethylcarbamate in Step 2.
3) methyl 2-((R)—((R)-1-((S)-2-amino-3-((R)-tetrahydro-2H-pyran-3-yl)propylcarbamoyl)piperidin-3-yl)(3,5-difluorophenyl)methoxy)ethylcarbamate (compound 4) using trifluoroacetic acid salt of methyl 2-((R)-(3,5-difluorophenyl)((R)-piperidin-3-yl)methoxy)ethylcarbamate in Step 2.
4) methyl 2-((R)—((R)-1-((S)-2-amino-3-((R)-tetrahydro-2H-pyran-3-yl)propylcarbamoyl)piperidin-3-yl)(5-chloro-2-methylphenyl)methoxy)ethylcarbamate (compound 5) using trifluoroacetic acid salt of methyl 2-((R)-(5-chloro-2-methylphenyl)((R)-piperidin-3-yl)methoxy)ethylcarbamate in Step 2.
5) methyl 2-((R)—((R)-1-((S)-2-amino-3-((R)-tetrahydro-2H-pyran-3-yl)propylcarbamoyl)piperidin-3-yl)(5-fluoro-2-methylphenyl)methoxy)ethylcarbamate (compound 6) using trifluoroacetic acid salt of methyl 2-((R)-(5-fluoro-2-methylphenyl)((R)-piperidin-3-yl)methoxy)ethylcarbamate in Step 2.
6) methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate (compound 7) using tert-butyl (S)-1-amino-3-((R)-tetrahydro-2H-pyran-3-yl)propan-2-yl(methyl)carbamate in Step 1.
7) methyl 2-((R)-(5-chloro-2-methylphenyl)((R)-1-((S)-2-(methylamino)-3-((R)-tetrahydro-2H-pyran-3-yl)propylcarbamoyl)piperidin-3-yl)methoxy)ethylcarbamate (compound 8) using tert-butyl (S)-1-amino-3-((R)-tetrahydro-2H-pyran-3-yl)propan-2-yl(methyl)carbamate in Step 1 and trifluoroacetic acid salt of methyl 2-((R)-(5-chloro-2-methylphenyl)((R)-piperidin-3-yl)methoxy)ethylcarbamate in Step 2.
8) methyl 2-((R)-(3-chloro-5-fluorophenyl)((R)-1-((S)-2-(methylamino)-3-((R)-tetrahydro-2H-pyran-3-yl)propylcarbamoyl)piperidin-3-yl)methoxy)ethylcarbamate (compound 9)
9) methyl 2-((R)-(3,5-difluorophenyl)((R)-1-((S)-2-(methylamino)-3-((R)-tetrahydro-2H-pyran-3-yl)propylcarbamoyl)piperidin-3-yl)methoxy)ethylcarbamate (compound 10)
10) methyl 2-((R)-(3-chlorophenyl)((R)-1-((S)-2-(ethylamino)-3-((R)-tetrahydro-2H-pyran-3-yl)propylcarbamoyl)piperidin-3-yl)methoxy)ethylcarbamate (compound 13)
11) methyl 2-((R)-(5-chloro-2-methylphenyl)((R)-1-((S)-2-(ethylamino)-3-((R)-tetrahydro-2H-pyran-3-yl)propylcarbamoyl)piperidin-3-yl)methoxy)ethylcarbamate (compound 12)

Alternatively, methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate (compound 7) may also be prepared by the following process (using procedures analogous to those described in Example 14) and isolated as its TFA salt:

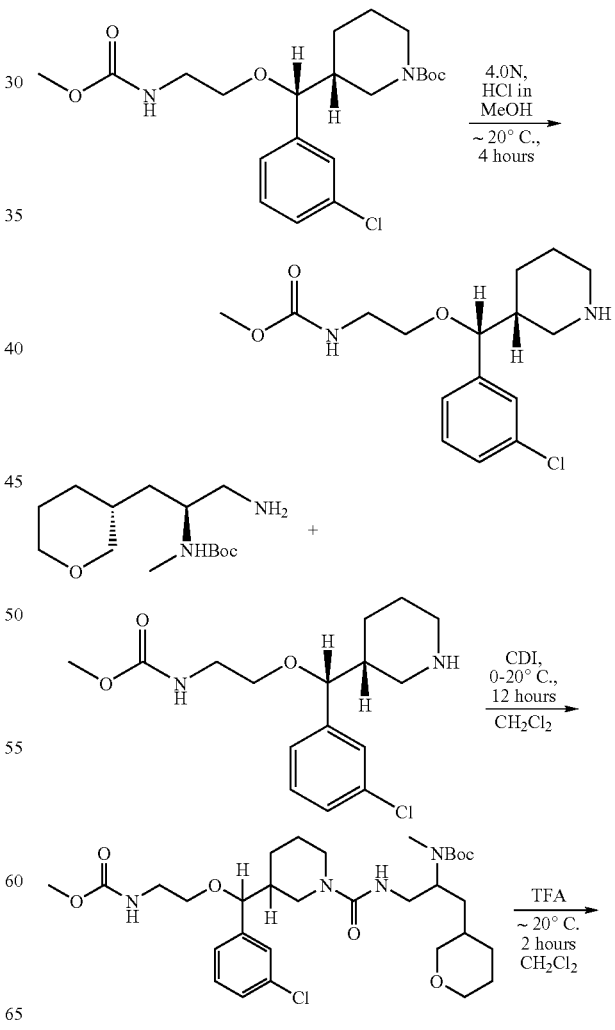

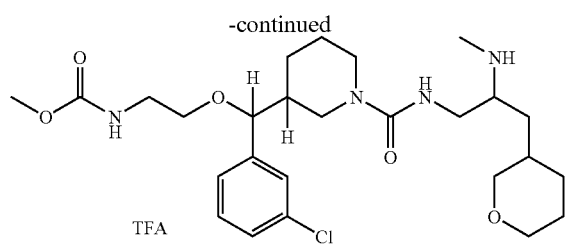

EXAMPLE 14

Methyl 2-((R)-(5-chloro-2-methylphenyl)((R)-1-((S)-2-(methylamino)-3-((R)-tetrahydro-2H-pyran-3-yl)propylcarbamoyl)piperidin-3-yl)methoxy)ethylcarbamate (Compound 11)

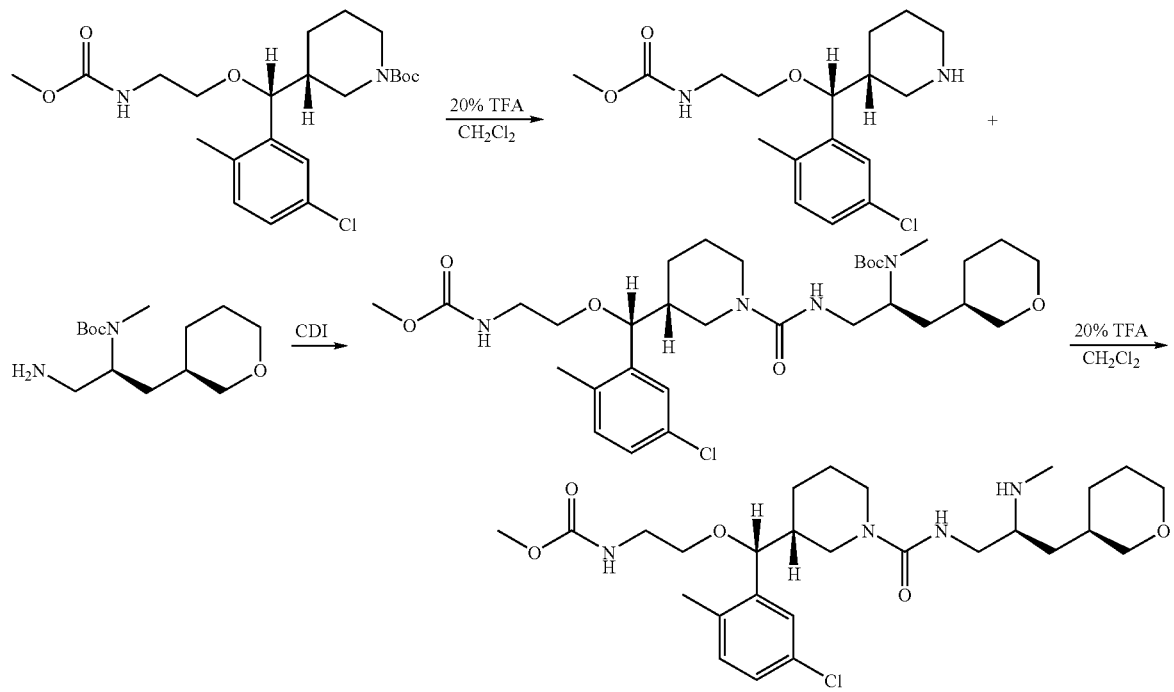

Step 1. Methyl 2-((R)-(5-chloro-2-methylphenyl)((R)-piperidin-3-yl)methoxy)ethylcarbamate (R)-tert-Butyl 3-((R)-(5-chloro-2-methylphenyl)(2-(methoxycarbonylamino)ethoxy)methyl)piperidine-1-carboxylate (1.0 g, 2.27 mmol) was dissolved in a solution of 20% (V/V) TFA/$CH_2Cl_2$ (20 mL). The reaction mixture was stirred at room temperature for 2 h, TLC showed the starting material disappeared, a solution of saturated sodium bicarbonate was added dropwise to adjust pH=7-8. The resulting mixture was extracted with $CH_2Cl_2$ (3×30 mL), washed with brine, dried over $Na_2SO_4$, concentrated in vacuo to afford methyl 2-((R)-(5-chloro-2-methylphenyl)((R)-piperidin-3-yl)methoxy)ethylcarbamate (780 mg, 100%).

Step 2. Methyl 2-((R)-(5-chloro-2-methylphenyl)((R)-1-((S)-2-(Boc-methylamino)-3-((R)-tetrahydro-2H-pyran-3-yl)propylcarbamoyl)piperidin-3-yl)methoxy)ethylcarbamate A 50 mL flask was charged with methyl tert-butyl (S)-1-amino-3-((R)-tetrahydro-2H-pyran-3-yl)propan-2-yl(methyl)carbamate (60 mg, 0.22 mmol) dissolved in dry $CH_2Cl_2$. To the solution was added CDI (36 mg, 0.22 mmol) and DIEA (142 mg, 1.1 mmol) at 0° C. and stirred for 1 h. Methyl 2-((R)-(5-chloro-2-methylphenyl)((R)-piperidin-3-yl)methoxy)ethylcarbamate trifluoroacetic acid salt (75 mg, 0.22 mmol) was added and stirred overnight. The mixture was concentrated to give the crude product. The residue was purified by chromatography to give the product (60 mg, 43%).

Step 3. Methyl 2-((R)-(5-chloro-2-methylphenyl)((R)-1-((S)-2-(methylamino)-3-((R)-tetrahydro-2H-pyran-3-yl)propylcarbamoyl)piperidin-3-yl)methoxy)ethylcarbamate A 25 mL flask was charged with methyl 2-((R)-(5-chloro-2-methylphenyl)((R)-1-((S)-2-(Boc-methylamino)-3-((R)-tetrahydro-2H-pyran-3-yl)propylcarbamoyl)piperidin-3-yl)methoxy)ethylcarbamate (60 mg, 0.094 mmol). 20% TFA/$CH_2Cl_2$ solution (8 mL) was added and stirred for 0.5 h at 0° C. The mixture was concentrated to give the residue, which was purified by preparative HPLC to give the desired product methyl 2-((R)-(5-chloro-2-methylphenyl)((R)-1-((S)-2-(methylamino)-3-((R)-tetrahydro-2H-pyran-3-yl)propylcarbamoyl)piperidin-3-yl)methoxy)ethylcarbamate (4.35 mg, 9%) as its TFA salt. $^1$H-NMR (MeOD): 1.25 (m, 2H), 1.35-1.50 (m, 4H), 1.60-1.80 (m, 3H), 1.95 (m, 2H), 2.35 (s, 3H), 2.75 (s, 3H), 3.65 (s, 3H), 3.85 (m, 4H), 4.45 (d, 1H), 7.15 (m, 2H), 7.30 (s, 1H).

The following are examples of aspartic protease inhibitors of the invention. When the stereochemistry at a chiral center is not defined in the compound name, this indicates that the sample prepared contained a mixture of isomers at this center.

| Cpd. No. | Cpd Name | LC-MS[a] (3 min) $t_R$ (min) | Mass Observed | Selected $^1$H NMR[b] |
|---|---|---|---|---|
| 1 | methyl 2-((R)-((R)-1-((S)-2-amino-3-((R)-tetrahydro-2H-pyran-3-yl)propylcarbamoyl)piperidin-3-yl)(3-chlorophenyl)methoxy)ethylcarbamate | 1.29 | 511 (M+) | 7.36-7.32 (m, 3H), 7.23 (d, J = 7.6 Hz, 1H), 4.20 (br d, J = 13.6 Hz, 1H), 4.04 (d, J = 8.8 Hz, 1H), 3.89-3.78 (m, 3H), 3.64 (s, 3H), 3.48-3.42 (m, 2H), 3.37 (m, 1H), 3.28-3.24 (m, 5H), 3.15 (dd, J = 10.8, 9.2 Hz, 1H), 2.92 (m, 2H), 1.97 (m, 1H), 1.78 (m, 2H), 1.68-1.54 (m, 4H), 1.45-1.07 (m, 5H) |
| 2 | methyl 2-((R)-((R)-1-((S)-2-amino-3-((R)-tetrahydro-2H-pyran-3-yl)propylcarbamoyl)piperidin-3-yl)(3-fluorophenyl)methoxy)ethylcarbamate | 1.22 | 495 (M + 1) | 7.39 (m, 1H), 7.12 (d, J = 7.6 Hz, 1H), 7.09-7.04 (m, 2H), 7.23 (d, J = 7.6 Hz, 1H), 4.21 (br d, J = 14.0 Hz, 1H), 4.07 (d, J = 8.8 Hz, 1H), 3.90-3.79 (m, 3H), 3.65 (s, 3H), 3.49-3.43 (m, 2H), 3.39-3.37 (m, 2H), 3.28-3.25 (m, 4H), 3.16 (dd, J = 10.8, 10.0 Hz, 1H), 2.94 (m, 2H), 1.98 (m, 1H), 1.79 (m, 2H), 1.68-1.53 (m, 4H), 1.46-1.07 (m, 5H) |
| 3 | methyl 2-((R)-((R)-1-((S)-2-amino-3-((R)-tetrahydro-2H-pyran-3-yl)propylcarbamoyl)piperidin-3-yl)(3-chloro-5-fluorophenyl)methoxy)ethylcarbamate | 1.32 | 529 (M+) | 7.19 (s, 1H), 7.16 (m, 1H), 7.23 (d, J = 8.8 Hz, 1H), 4.19 (br d, J = 14.4 Hz, 1H), 4.07 (d, J = 8.8 Hz, 1H), 3.89-3.79 (m, 3H), 3.64 (s, 3H), 3.48-3.42 (m, 2H), 3.40-3.34 (m, 2H), 3.30-3.24 (m, 4H), 3.19 (dd, J = 11.2, 9.2 Hz, 1H), 2.91 (m, 2H), 1.97 (m, 1H), 1.75 (m, 2H), 1.70-1.52 (m, 4H), 1.45-1.17 (m, 5H) |
| 4 | methyl 2-((R)-((R)-1-((S)-2-amino-3-((R)-tetrahydro-2H-pyran-3-yl)propylcarbamoyl)piperidin-3-yl)(3,5-difluorophenyl)methoxy)ethylcarbamate | 1.25 | 513 (M + 1) | 6.96-6.91 (m, 3H), 4.19 (br d, J = 13.6 Hz, 1H), 4.09 (d, J = 8.8 Hz, 1H), 3.89-3.79 (m, 3H), 3.65 (s, 3H), 3.49-3.43 (m, 2H), 3.39-3.37 (m, 2H), 3.30-3.25 (m, 4H), 3.16 (dd, J = 10.8, 10.0 Hz, 1H), 2.92 (m, 2H), 1.97 (m, 1H), 1.77 (m, 2H), 1.68-1.53 (m, 4H), 1.45-1.09 (m, 5H) |
| 5 | methyl 2-((R)-((R)-1-((S)-2-amino-3-((R)-tetrahydro-2H-pyran-3-yl)propylcarbamoyl)piperidin-3-yl)(5-chloro-2-methylphenyl)methoxy)ethylcarbamate | 1.34 | 525 (M+) | 7.32 (s, 1H), 7.21-7.15 (m, 2H), 4.34 (d, J = 8.8 Hz, 1H), 4.29 (br d, J = 14.4 Hz, 1H), 3.87 (m, 3H), 3.64 (s, 3H), 3.48-3.42 (m, 2H), 3.38-3.34 (m, 2H), 3.30-3.24 (m, 4H), 3.19 (dd, J = 10.8, 9.6 Hz, 1H), 2.87 (m, 2H), 2.34 (s, 3H), 1.98 (m, 1H), 1.79 (m, 2H), 1.71-1.53 (m, 4H), 1.45-1.24 (m, 5H) |
| 6 | methyl 2-((R)-((R)-1-((S)-2-amino-3-((R)-tetrahydro-2H-pyran-3-yl)propylcarbamoyl)piperidin-3-yl)(5-fluoro-2-methylphenyl)methoxy)ethylcarbamate | 1.28 | 509 (M + 1) | 7.20 (dd, J = 6.8, 2.4 Hz, 1H), 7.14 (m, 1H), 6.97 (dd, J = 10.0, 8.4 Hz, 1H), 4.41 (d, J = 8.8 Hz, 1H), 4.16 (br d, J = 12.4 Hz, 1H), 3.87 (m, 2H), 3.77 (br d, J = 12.8 Hz, 1H), 3.45 (m, 2H), 3.35 (m, 1H), 3.48-3.42 (m, 2H), 3.38-3.34 (m, 2H), 3.29-3.26 (m, 4H), 3.16 (dd, J = 11.2, 9.6 Hz, 1H), 3.00 (m, 2H), 2.34 (s, 3H), 1.97 (m, 1H), 1.86 (m, 1H), 1.71 (m, 1H), 1.66 (m, 3H), 1.56 (m, 1H), 1.45-1.21 (m, 5H) |

| | | | | |
|---|---|---|---|---|
| 7 | methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate | 1.3 | 525 (M+) | 7.37-7.29 (m, 3H), 7.21 (d, J = 6.8 Hz, 1H), 4.20 (br d, J = 12.4 Hz, 1H), 4.02 (d, J = 9.2 Hz, 1H), 3.87-3.78 (m, 3H), 3.62 (s, 3H), 3.57 (d, J = 15.2 Hz, 1H), 3.44 (dd, J = 11.2, 3.6 Hz, 1H), 3.28-3.22 (m, 6H), 3.15 (td, J = 10.8, 9.6 Hz, 1H), 2.89 (m, 2H), 2.75 (s, 3H), 1.97 (m, 1H), 1.77 (m, 2H), 1.65-1.17 (m, 9H) |
| 8 | methyl 2-((R)-(5-chloro-2-methylphenyl)((R)-1-((S)-2-(methylamino)-3-((R)-tetrahydro-2H-pyran-3-yl)propylcarbamoyl)piperidin-3-yl)methoxy)ethylcarbamate | 1.34 | 539 (M+) | 7.30 (d, J = 2.4 Hz, 1H), 7.19-7.13 (m, 2H), 4.33-4.27 (m, 2H), 3.87-3.84 (m, 3H), 3.62 (s, 3H), 3.57 (d, J = 13.2 Hz, 1H), 3.44 (td, J = 10.8, 3.2 Hz, 1H), 3.29-3.21 (m, 6H), 3.15 (dd, J = 11.2, 9.6 Hz, 1H), 2.85 (m, 2H), 2.74 (s, 3H), 2.32 (s, 3H), 1.98 (m, 1H), 1.76 (m, 2H), 1.65-1.21 (m, 9H) |
| 9 | methyl 2-((R)-(3-chloro-5-fluorophenyl)((R)-1-((S)-2-(methylamino)-3-((R)-tetrahydro-2H-pyran-3-yl)propylcarbamoyl)piperidin-3-yl)methoxy)ethylcarbamate | 1.35 | 543 (M + H) | 7.17-7.14 (m, 2H), 7.03 (d, J = 8.8 Hz, 1H), 4.19 (br d, J = 12.0 Hz, 1H), 4.05 (d, J = 8.4 Hz, 1H), 3.87-3.78 (m, 3H), 3.62 (s, 3H), 3.57 (d, J = 14.4 Hz, 1H), 3.44 (td, J = 10.8, 3.6 Hz, 1H), 3.32-3.26 (m, 6H), 3.15 (dd, J = 11.2, 9.6 Hz, 1H), 2.88 (m, 2H), 2.74 (s, 3H), 1.97 (m, 1H), 1.78-1.19 (m, 11H) |
| 10 | methyl 2-((R)-(3,5-difluorophenyl)((R)-1-((S)-2-(methylamino)-3-((R)-tetrahydro-2H-pyran-3-yl)propylcarbamoyl)piperidin-3-yl)methoxy)ethylcarbamate | 1.26 | 527 (M + H) | 6.93-6.86 (m, 3H), 4.19 (br d, J = 13.2 Hz, 1H), 4.05 (d, J = 8.4 Hz, 1H), 3.85 (br d, J = 11.6 Hz, 2H), 3.79 (br d, J = 14.0 Hz, 1H), 3.62 (s, 3H), 3.56 (d, J = 13.2 Hz, 1H), 3.43 (td, J = 11.2, 3.2 Hz, 1H), 3.34-3.23 (m, 6H), 3.15 (dd, J = 11.2, 9.6 Hz, 1H), 2.88 (m, 2H), 2.74 (s, 3H), 1.97 (m, 1H), 1.78-1.17 (m, 11H) |
| 11 | methyl 2-((S)-(5-chloro-2-methylphenyl)((R)-1-((S)-2-(methylamino)-3-((R)-tetrahydro-2H-pyran-3-yl)propylcarbamoyl)piperidin-3-yl)methoxy)ethylcarbamate | 1.795 | 539.1, 561.0 | 1.93 (m, 2H), 2.32 (s, 3H), 2.72 (s, 3H), 2.85 (m, 2H), 3.66 (s, 3H), 3.85 (m, 4H), 4.43 (d, 1H), 7.16 (m, 2H), 7.32 (s, 1H)c |
| 12 | methyl 2-((R)-(5-chloro-2-methylphenyl)((R)-1-((S)-2-(ethylamino)-3-((R)-tetrahydro-2H-pyran-3-yl)propylcarbamoyl)piperidin-3-yl)methoxy)ethylcarbamate | 1.4 | 552 (M + H) | 7.30 (d, J = 2.0 Hz, 1H), 7.19-7.14 (m, 2H), 4.33-4.28 (m, 2H), 3.88-384 (m, 3H), 3.62 (s, 3H), 3.58 (d, J = 13.2 Hz, 1H), 3.44 (td, J = 10.8, 3.2 Hz, 1H), 3.35-3.10 (m, 9H), 2.86 (m, 2H), 2.32 (s, 3H), 1.97 (m, 1H), 1.79-1.22 (m, 8H), 1.32 (t, J = 7.2 Hz, 3H). |

-continued

| | | | | |
|---|---|---|---|---|
| 13 | methyl 2-((R)-(3-chlorophenyl)((R)-1-((S)-2-(ethylamino)-3-((R)-tetrahydro-2H-pyran-3-yl)propylcarbamoyl)piperidin-3-yl)methoxy)ethylcarbamate | 1.36 | 539 (M + H) | 7.37-7.30 (m, 3H), 7.22 (d, J = 7.2 Hz, 1H), 4.21 (br d, J = 12.4 Hz, 1H), 4.02 (d, J = 9.2 Hz, 1H), 3.87-3.79 (m, 3H), 3.62 (s, 3H), 3.58 (d, J = 14.4 Hz, 1H), 3.44 (td, J = 10.8, 3.2 Hz, 1H), 3.34-3.11 (m, 9H), 2.90 (m, 2H), 1.98 (m, 1H), 1.78-1.15 (m, 8H), 1.33 (t, J = 7.2 Hz, 3H). |

[a]LC-MS (3 min) method
Column: Chromolith SpeedRod, RP-18e, 50 × 4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

[b]d$_4$-MeOH was used as $^1$H NMR solvent.
[c]MeOD was used as $^1$H NMR solvent.

EXAMPLE 15

2:1 Methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)-ethylcarbamate pamoate salt Step 1.

To a solution of methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)-ethylcarbamate (8.27 g, 15.7 mmol), in IPA (50 mL), pamoic acid (3.12 g, 7.85 mmol) was added. The resulting mixture was heated at 40° C. overnight, cooled to room temperature and stirred for 10 hours, which gave a yellow suspension. The solid was filtered, washed with IPA (100 mL), and dried under vacuum to give crude 2:1 methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate pamoate salt (10.9 g, 96%).

Step 2.

The above pamoate salt (7.44 g) was refluxed in ethanol (74 mL) until dissolved. The resulting solution was hot filtered and cooled slowly to room temperature, and stirred overnight. Solid was filtered and washed with ethanol (25 mL) to give 0.5 eq pamoate salt as a pale yellow crystal (5.52 g, 74%); m.p.: 155.5-156.5° C.

Step 3.

The recrystallized pamoate salt crystal (7.85 g) was refluxed in ethanol (70 mL) until dissolved, hot filtered, cooled to room temperature and stirred overnight. The solid was filtered and washed with ethanol (20 mL) to give a pale yellow fine crystal (6.99 g, 89%).

EXAMPLE 16

2:1 Methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)-ethylcarbamate pamoate salt The recrystallized pamoate salt crystal (0.19 g), obtained from Example 15, Step 3, was heated in methanol (5 mL) at 60° C. until totally dissolved. The solution was then cooled to room temperature and seeded with 2:1 methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)-ethylcarbamate pamoate salt crystals (~5 mg). The resulting mixture was stirred at room temperature over 48 hrs. The solid was filtered and dried under vacuum to give a pale yellow fine crystal (53.0 mg, 28%).

X-Ray Powder Diffraction

X-ray powder diffraction patterns of 2:1 methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)-ethylcarbamate pamoate salt, which was obtained by the procedure described in Example 15, were determined using the following method:

The sample is scanned using the following parameters:
Scan range: 240 degrees two-theta
Generator power: 40 kV, 40 mA
Radiation Source Cu Kα
Scan type: Continuous
Time per step: 10 seconds
Step size: 0.017 degrees two-theta per step
Sample Rotation: 1 s revolution time
Incident Beam optics: 0.04 radian soller slits, 0.25 degree divergent slit, 10 mm beam mask, 0.5 degrees anti-scatter slit
Diffracted Beam optics: fixed slits (X'celerator module), 0.04 radian soller slits
Detector Type Philips X'Celerator RTMS (Real Time Multi Strip)

X-ray powder diffraction of one batch of 2:1 methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)-ethylcarbamate pamoate salt is shown in FIG. 1.

EXAMPLE 17

In Vitro Activity Studies

The disclosed aspartic protease inhibitors have enzyme-inhibiting properties. In particular, they inhibit the action of the natural enzyme renin. The latter passes from the kidneys into the blood where it effects the cleavage of angiotensinogen, releasing the decapeptide angiotensin I which is then cleaved in the blood, lungs, the kidneys and other organs by angiotensin converting enzyme to form the octapeptide angiotensin II. The octapeptide increases blood pressure both directly by binding to its receptor, causing arterial vasoconstriction, and indirectly by liberating from the adrenal glands the sodium-ion-retaining hormone aldosterone, accompanied by an increase in extracellular fluid volume. That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of the hypotensive effect of renin inhibitors.

The action of renin inhibitors in vitro can be demonstrated experimentally by means of a test which measures the increase in fluorescence of an internally quenched peptide substrate. The sequence of this peptide corresponds to the sequence of human angiotensinogen. The following test protocol was used. All reactions were carried out in a flat bottom white opaque microtiter plate. A 4 µL aliquot of 400 µM renin substrate (DABCYL-γ-Abu-Ile-His-Pro-Phe-His-Leu-Val-Ile-His-Thr-EDANS) in 192 µL assay buffer (50 mM BES, 150 mM NaCl, 0.25 mg/mL bovine serum albumin, pH7.0) was added to 4 µL of test compound in DMSO at various concentrations ranging from 10 µM to 1 nM final concentrations. Next, 100 µL of trypsin-activated recombinant human renin (final enzyme concentration of 0.2-2 nM) in assay buffer was added, and the solution was mixed by pipetting. The increase in fluorescence at 495 mm (excitation at 340 nm) was measured for 60-360 minutes at rt using a Perkin-Elmer Fusion microplate reader. The slope of a linear portion of the plot of fluorescence-increase as a function of time was then determined, and the rate is used for calculating percent inhibition in relation to uninhibited control. The percent inhibition values were then plotted as a function of inhibitor concentration, and the $IC_{50}$ was determined from a fit of this data to a four parameter equation. The $IC_{50}$ was defined as the concentration of a particular inhibitor that reduces the formation of product by 50% relative to a control sample containing no inhibitor. In the in vitro systems, the disclosed aspartic protease inhibitors exhibit inhibiting activities at minimum concentrations of from approximately $5 \times 10^{-5}$ M to approximately $10^{-12}$ M. Specific aspartic protease inhibitors exhibit inhibiting activities at minimum concentrations of from approximately $10^{-7}$ M to approximately $10^{-12}$ M. (Wang G. T. et al., *Anal. Biochem.* 1993, 210, 351; Nakamura, N. et al. *J. Biochem.* (Toyo) 1991, 109, 741; Murakami, K. et al. *Anal Biochem.* 1981, 110, 232).

The action of renin inhibitors in vitro in human plasma can also be demonstrated experimentally by the decrease in plasma renin activity (PRA) levels observed in the presence of the compounds. Incubations mixtures contained in the final volume of 250 µL 95.5 mM N,N-bis(2-hydroxyethyl)-2-aminoethanesulfonic acid, pH 7.0, 8 mM EDTA, 0.1 mM neomycin sulfate, 1 mg/mL sodium azide, 1 mM phenylmethanesulfonyl fluoride, 2% DMSO and 87.3% of pooled mixed-gender human plasma stabilized with EDTA. For plasma batches with low PRA (less than 1 ng/ml/hr)~2 µM of recombinant human renin was added to achieve PRA of 3-4 ng/ml/hr. The cleavage of endogenous angiotensinogen in plasma was carried out at 37° C. for 90 min and the product angiotensin I was measured by competitive radioimmunoassay using DiaSorin PRA kit. Uninhibited incubations containing 2% DMSO and fully inhibited controls with 2 µM of isovaleryl-Phe-Nle-Sta-Ala-Sta-OH were then used for deriving percent of inhibition for each concentration of inhibitors and fitting dose-response data into a four parametric model from which $IC_{50}$ values, defined as concentrations of inhibitors at which 50% inhibition occurs, are determined.

The in vitro enzyme activity studies were carried out for compounds 1-12 and the data is shown in Table 1.

TABLE 1

In vitro $IC_{50}$ and PRA data for aspartic protease inhibitors

| Cpd No. | $IC_{50}$ | PRA |
|---|---|---|
| 1 | *** | *** |
| 2 | *** | ** |
| 3 | *** | *** |
| 4 | *** | *** |
| 5 | **** | **** |
| 6 | *** | * |
| 7 | **** | *** |
| 8 | **** | *** |
| 9 | **** | *** |
| 10 | *** | *** |
| 11 | *** | *** |
| 12 | *** | nt |

*represents less than 50 nM;
**represents less than 20 nM;
***represents less than 10 nM;
****represents less than 1 nM;
nt: not tested.

EXAMPLE 18

In Vivo Activity Studies

The cardiac and systemic hemodynamic efficacy of renin inhibitors can be evaluated in vivo in sodium-depleted, normotensive cynomolgus monkeys. Arterial blood pressure is monitored by telemetry in freely moving, conscious animals.

Cynomolgus Monkey (prophetic example): Six male naïve cynomolgus monkeys weighing between 2.5 and 3.5 kg are to be used in the studies. At least 4 weeks before the experiment, the monkeys are anesthetized with ketamine hydrochloride (15 mg/kg, i.m.) and xylazine hydrochloride (0.7 mg/kg, i.m.), and are implanted into the abdominal cavity with a transmitter (Model #TL11M2-D70-PCT, Data Sciences, St. Paul, Minn.). The pressure catheter is inserted into the lower abdominal aorta via the femoral artery. The bipotential leads are placed in Lead II configuration. The animals are housed under constant temperature (19-25° C.), humidity (>40%) and lighting conditions (12 h light and dark cycle), are fed once daily, and are allowed free access to water. The animals are sodium depleted by placing them on a low sodium diet (0.026%, Expanded Primate Diet 829552 MP-VENaCl (P), Special Diet Services, Ltd., UK) 7 days before the experiment and furosemide (3 mg/kg, intramuscularly i.m., Aventis Pharmaceuticals) is administered at −40 h and −16 h prior to administration of test compound.

For oral dosing, the renin inhibitors are formulated in 0.5% methylcellulose at dose levels of 10 and 30 mg/kg (5 mL/kg) by infant feeding tubes. For intravenous delivery, a silastic catheter is implanted into posterior vena cava via a femoral vein. The catheter is attached to the delivery pump via a tether system and a swivel joint. Test compound (dose levels of 0.1 to 10 mg/kg, formulated at 5% dextrose) is administered by continuous infusion (1.67 mL/kg/h) or by bolus injection (3.33 mL/kg in 2 min).

Arterial blood pressures (systolic, diastolic and mean) and body temperature are recorded continuously at 500 Hz and 50 Hz, respectively, using the Dataquest™ A.R.T. (Advanced Research Technology) software. Heart rate is derived from the phasic blood pressure tracing. During the recording period, the monkeys are kept in a separate room without human presence to avoid pressure changes secondary to stress. All data are expressed as mean±SEM. Effects of the renin inhibitors on blood pressure are assessed by ANOVA, taking into account the factors dose and time compared with the vehicle group.

Double Transgenic Rats: The efficacy of the renin inhibitors can also be evaluated in vivo in double transgenic rats engineered to express human renin and human angiotensinogen (Bohlender J, Fukamizu A, Lippoldt A, Nomura T, Dietz R, Menard J, Murakami K, Luft F C, Ganten D. High human renin hypertension in transgenic rats. *Hypertension* 1997, 29, 428-434). In vivo activity for compound 7 was conducted according to the following procedures.

Experiments were conducted in 6-week-old double transgenic rats (dTGRs). The model has been described in detail earlier. Briefly, the human renin construct used to generate transgenic animals made up the entire genomic human renin gene (10 exons and 9 introns), with 3.0 kB of the 5'-promoter region and 1.2 kB of 3' additional sequences. The human angiotensinogen construct made up the entire human angiotensinogen gene (5 exons and 4 introns), with 1.3 kB of 5'-flanking and 2.4 kB of 3'-flanking sequences. The rats were purchased from RCC Ltd (Füllinsdorf, Switzerland). Radio telemetry transmitters were surgically implanted at 4 weeks of age. The telemetry system provided 24 h recordings of systolic, mean, diastolic arterial pressure (SAP, MAP, DAP, respectively) and heart rate (HR). Beginning on day 42, animals were transferred to telemetry cages. A 24 h telemetry reading was obtained. Rats were then dosed orally on the following 4 consecutive days (days 43-46). The rats were monitored continuously and allowed free access to standard 0.3%-sodium rat chow and drinking water.

Figure 2:
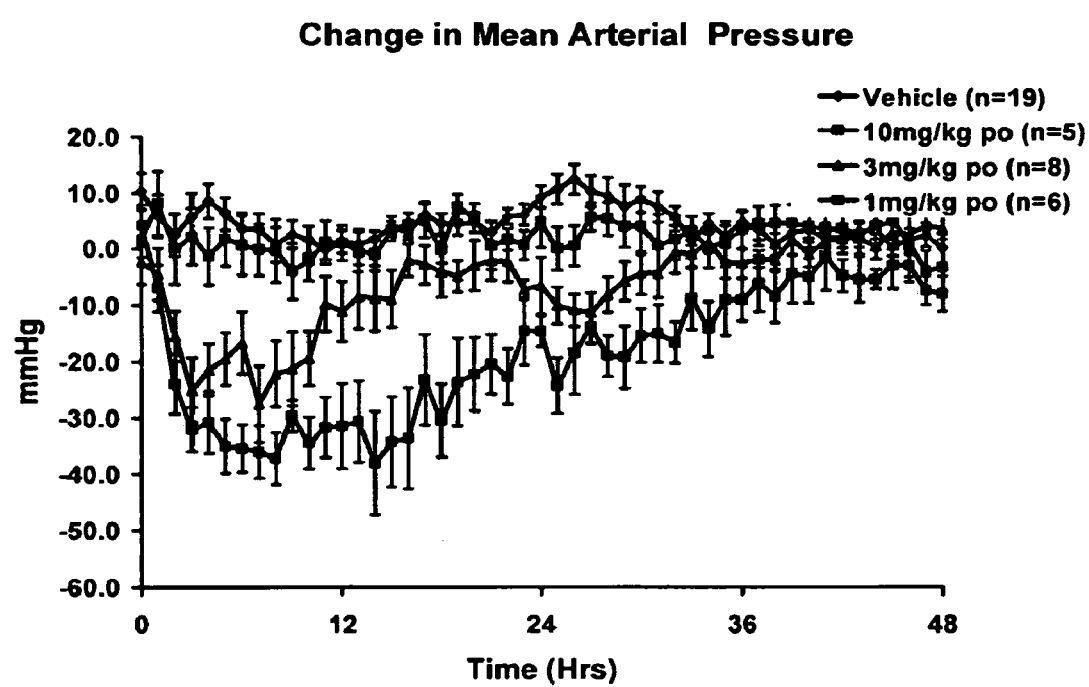
FIG. 2 is a plot showing changes in mean arterial blood pressures of transgenic rats treated with 1 mg/kg, 3 mg/kg or 10 mg/kg of compound 7.

The in vivo transgenic rat activity for compound 7 is shown in the FIG. 2. As shown in the FIG. 2, compound 7 exhibited significant effect in lowering blood pressures of transgenic rats at a dosage of 3-10 mg/kg.

While this invention has been particularly shown and described with references to specific embodiments thereof, it will be understood by those skilled in the art that various changes in form and details may be made therein without departing from the scope of the invention encompassed by the appended claims.

What is claimed is:

1. A compound represented by the following structural formula:

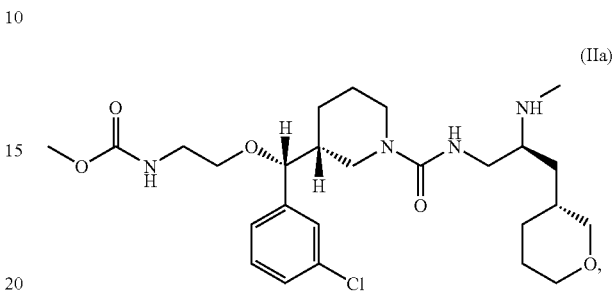

(IIa)

or a pharmaceutically acceptable salt thereof.

2. A pharmaceutical composition comprising a pharmaceutically acceptable carrier or diluent and the compound of claim 1.

3. The pharmaceutical composition of claim 2, further comprising a α-blocker, β-blocker, calcium channel blocker, diuretic, natriuretic, saluretic, centrally acting antihypertensive, angiotensin converting enzyme inhibitor, dual angiotensin converting enzyme and neutral endopeptidase inhibitor, an angiotensin-receptor blocker, dual angiotensin-receptor blocker and endothelin receptor antagonist, aldosterone synthase inhibitor, aldosterone-receptor antagonist, or endothelin receptor antagonist.

* * * * *